(12) United States Patent
Thevenet et al.

(10) Patent No.: US 9,649,261 B2
(45) Date of Patent: *May 16, 2017

(54) METHOD OF APPLYING MAKEUP TO A SURFACE AND A KIT FOR IMPLEMENTING SUCH A METHOD

(71) Applicant: L'OREAL, Paris (FR)

(72) Inventors: Ludovic Thevenet, Bourg la Reine (FR); Xavier Blin, Paris (FR)

(73) Assignee: L'OREAL, Paris (FR)

( * ) Notice: Subject to any disclaimer, the term of this patent is extended or adjusted under 35 U.S.C. 154(b) by 907 days.

This patent is subject to a terminal disclaimer.

(21) Appl. No.: 13/777,573

(22) Filed: Feb. 26, 2013

(65) Prior Publication Data

US 2013/0160785 A1    Jun. 27, 2013

Related U.S. Application Data

(63) Continuation-in-part of application No. 11/242,901, filed on Oct. 5, 2005, now abandoned, and a continuation-in-part of application No. 11/242,900, filed on Oct. 5, 2005, now abandoned, and a continuation-in-part of application No. 11/663,977, filed as application No. PCT/FR2005/050563 on Jul. 8, 2005, now abandoned, application No. 13/777,573, which is a continuation-in-part of application No. 11/663,978, filed as application No. PCT/FR2005/050559 on Aug. 16, 2007, now abandoned, and a continuation-in-part of application No. 11/663,776, filed as application No. PCT/FR2005/050564 on Jul. 8, 2005, now abandoned, and a continuation-in-part of application No. 11/664,003, filed as application No. PCT/FR2005/050560 on Jul. 8, 2005, now abandoned.

(60) Provisional application No. 60/619,928, filed on Oct. 20, 2004, provisional application No. 60/619,927, filed on Oct. 20, 2004.

(30) Foreign Application Priority Data

Oct. 5, 2004   (FR) .................................. 04 10501
Oct. 5, 2004   (FR) .................................. 04 10509

(51) Int. Cl.
| | |
|---|---|
| *A61K 8/02* | (2006.01) |
| *A45D 33/00* | (2006.01) |
| *A45D 34/00* | (2006.01) |
| *A61Q 1/02* | (2006.01) |
| *A61Q 3/02* | (2006.01) |
| *A61K 8/19* | (2006.01) |
| *A45D 34/04* | (2006.01) |
| *A45D 29/00* | (2006.01) |
| *A61Q 1/06* | (2006.01) |

(52) U.S. Cl.
CPC ............ *A61K 8/0241* (2013.01); *A45D 33/00* (2013.01); *A45D 34/00* (2013.01); *A45D 34/04* (2013.01); *A45D 34/045* (2013.01); *A61K 8/19* (2013.01); *A61Q 1/02* (2013.01); *A61Q 3/02* (2013.01); *A45D 29/004* (2013.01); *A45D 2034/007* (2013.01); *A45D 2200/25* (2013.01); *A61K 2800/47* (2013.01); *A61K 2800/88* (2013.01); *A61Q 1/06* (2013.01)

(58) Field of Classification Search
CPC ...... A45D 34/05; A45D 29/004; A45D 29/22; A61K 8/0241; A61K 8/19; A61K 2800/47; A61Q 1/02; A61Q 3/01
See application file for complete search history.

(56) References Cited

U.S. PATENT DOCUMENTS

| | | | |
|---|---|---|---|
| 3,030,967 A | 4/1962 | Peyron | |
| 3,461,885 A | 8/1969 | Coveney | |
| 3,516,422 A | 6/1970 | Bechtold et al. | |
| 3,623,732 A | 11/1971 | Peeples | |
| 3,791,386 A * | 2/1974 | McDonald | A61M 16/0472 128/207.29 |

(Continued)

FOREIGN PATENT DOCUMENTS

| | | |
|---|---|---|
| DE | 196 45 648 | 7/1997 |
| DE | 102 19 196 A1 | 11/2003 |

(Continued)

OTHER PUBLICATIONS

Merriam-Webster's Collegiate Dictionary, $11^{th}$ ed., 2004, entry for "manual," p. 757.*
Furst, E.M. et al., "Permanently Linked Monodisperse Paramagnetic Chains," Langmuir 14(26): 7334-36, Nov. 26, 1998.
Hansen, C.M., "Three Dimensional Solubility Parameter—Key to Paint Component Affinities: I. Solvents, Plasticizers, Polymers, and Resins," J. Paint Tech. 39(505): 104-117 (1967).
Fermigier, et al., "Suspensions de particules magnetiques," Bulletin of the SFP (105): pp. 3-5, Jul. 1996.
Goubault, C., "Flexible Magnetic Filaments as Micromechanical Sensors, "Physical Review Letters 91(26): 260802-1-260802-4 (2003).

(Continued)

*Primary Examiner* — David J Blanchard
*Assistant Examiner* — Ivan Greene
(74) *Attorney, Agent, or Firm* — Oliff PLC

(57) ABSTRACT

A method of applying makeup to a surface, such as the skin, the nails, hair, or the lips, is disclosed. The method includes manually depositing, using a non-magnetic cosmetic applicator, at least a first cosmetic composition in the fluid state on the surface, the first composition containing magnetic particles that are movable under the effect of a magnetic field; and manually exposing at least part of the first composition to a magnetic device producing a magnetic field, the magnetic device located above the first composition so as to orientate and/or displace at least a fraction of the magnetic particles so as to form at least one pattern according to magnetic field lines of the magnetic field without making contact with the first composition.

24 Claims, 4 Drawing Sheets

(56) References Cited

U.S. PATENT DOCUMENTS

| | | | |
|---|---|---|---|
| 3,791,864 A * | 2/1974 | Steingroever | B05D 3/20 |
| | | | 427/550 |
| 3,836,537 A | 9/1974 | Boerwinkle et al. | |
| 3,910,862 A | 10/1975 | Barabas et al. | |
| 3,926,659 A | 12/1975 | Bernhard et al. | |
| 3,937,811 A | 2/1976 | Papantoniou et al. | |
| 4,031,307 A | 6/1977 | DeMartino et al. | |
| 4,055,377 A * | 10/1977 | Erickson | G02B 5/128 |
| | | | 359/518 |
| 4,131,576 A | 12/1978 | Iovine et al. | |
| 4,223,009 A | 9/1980 | Chakrabarti | |
| 4,318,844 A | 3/1982 | Kohler et al. | |
| 4,425,326 A | 1/1984 | Guillon et al. | |
| 4,470,715 A | 9/1984 | Reuchlin et al. | |
| 4,614,366 A * | 9/1986 | North | G06K 19/06028 |
| | | | 235/375 |
| 4,693,935 A | 9/1987 | Mazurek | |
| 4,728,571 A | 3/1988 | Clemens et al. | |
| 4,972,037 A | 11/1990 | Garbe et al. | |
| 4,981,902 A | 1/1991 | Mitra et al. | |
| 4,981,903 A | 1/1991 | Garbe et al. | |
| 5,000,688 A | 3/1991 | Clamp | |
| 5,030,669 A | 7/1991 | Hendrickson et al. | |
| 5,040,914 A | 8/1991 | Fitjer | |
| 5,061,481 A | 10/1991 | Suzuki et al. | |
| 5,066,485 A | 11/1991 | Brieva et al. | |
| 5,122,418 A | 6/1992 | Nakane et al. | |
| 5,127,952 A | 7/1992 | Persello et al. | |
| 5,133,805 A | 7/1992 | Kurata et al. | |
| 5,162,410 A | 11/1992 | Sweet | |
| 5,188,815 A | 2/1993 | Coates et al. | |
| 5,188,899 A | 2/1993 | Matsumoto et al. | |
| 5,199,808 A | 4/1993 | Gueret | |
| 5,206,011 A | 4/1993 | Pappas et al. | |
| 5,209,924 A | 5/1993 | Garbe et al. | |
| 5,219,560 A | 6/1993 | Suzuki et al. | |
| 5,291,345 A | 3/1994 | Umeda et al. | |
| 5,307,847 A * | 5/1994 | Pavenick | A45D 34/045 |
| | | | 141/20.5 |
| 5,316,026 A | 5/1994 | Jenkins | |
| 5,330,747 A | 7/1994 | Krzysik | |
| 5,356,617 A | 10/1994 | Schlossman | |
| 5,362,485 A | 11/1994 | Hayama et al. | |
| 5,380,359 A | 1/1995 | Honda et al. | |
| 5,393,526 A | 2/1995 | Castro | |
| 5,424,006 A | 6/1995 | Murayama et al. | |
| 5,451,610 A | 9/1995 | Krzysik | |
| 5,468,477 A | 11/1995 | Kumar et al. | |
| 5,472,798 A | 12/1995 | Kumazawa et al. | |
| 5,486,354 A | 1/1996 | Defossez et al. | |
| 5,512,273 A | 4/1996 | Martin | |
| 5,562,706 A | 10/1996 | Lauterbach et al. | |
| 5,625,005 A | 4/1997 | Mallya et al. | |
| 5,641,835 A | 6/1997 | Smith et al. | |
| 5,643,672 A | 7/1997 | Marchi et al. | |
| 5,658,574 A | 8/1997 | Bahary et al. | |
| 5,683,706 A | 11/1997 | LaFleur et al. | |
| 5,705,093 A | 1/1998 | Coates et al. | |
| 5,725,483 A | 3/1998 | Podolsky | |
| 5,725,882 A | 3/1998 | Kumar et al. | |
| 5,846,310 A | 12/1998 | Noguchi et al. | |
| 5,849,275 A | 12/1998 | Calello et al. | |
| 5,849,318 A | 12/1998 | Imai et al. | |
| 5,851,517 A | 12/1998 | Mougin et al. | |
| 5,856,653 A | 1/1999 | Boudreaux | |
| 5,873,375 A * | 2/1999 | Johnson | A45D 29/004 |
| | | | 132/200 |
| 5,874,069 A | 2/1999 | Mendolia et al. | |
| 5,913,631 A | 6/1999 | Landry | |
| 5,919,441 A | 7/1999 | Mendolia et al. | |
| 5,931,166 A | 8/1999 | Weber et al. | |
| 5,948,393 A | 9/1999 | Tomomasa et al. | |
| 5,954,871 A | 9/1999 | Nicolas-Morgantini et al. | |
| 5,981,680 A | 11/1999 | Petroff et al. | |
| 6,001,338 A | 12/1999 | Mondet | |
| 6,033,648 A | 3/2000 | Candau | |
| 6,033,650 A | 3/2000 | Calello et al. | |
| 6,033,655 A | 3/2000 | Lahanas et al. | |
| 6,051,216 A | 4/2000 | Barr et al. | |
| 6,071,632 A | 6/2000 | Hall-Goulle | |
| 6,074,654 A | 6/2000 | Drechsler et al. | |
| 6,117,435 A | 9/2000 | Painter et al. | |
| 6,117,574 A | 9/2000 | Watanabe et al. | |
| 6,136,907 A | 10/2000 | Sunamori et al. | |
| 6,177,093 B1 | 1/2001 | Lombardi et al. | |
| 6,203,781 B1 | 3/2001 | Chevalier et al. | |
| 6,203,909 B1 | 3/2001 | Chassot | |
| 6,209,548 B1 | 4/2001 | Harrison et al. | |
| 6,213,131 B1 | 4/2001 | Vien et al. | |
| 6,254,876 B1 | 7/2001 | de la Poterie et al. | |
| 6,280,655 B1 | 8/2001 | Xu et al. | |
| 6,299,979 B1 | 10/2001 | Neubauer et al. | |
| 6,358,495 B1 | 3/2002 | Nishihama et al. | |
| 6,387,498 B1 | 5/2002 | Coulter et al. | |
| 6,403,106 B1 | 6/2002 | Sebag et al. | |
| 6,428,773 B1 | 8/2002 | Oko et al. | |
| 6,432,386 B1 | 8/2002 | Rollat-Corvol et al. | |
| 6,432,423 B1 | 8/2002 | Maignan et al. | |
| 6,451,294 B1 | 9/2002 | Simon | |
| 6,477,398 B1 | 11/2002 | Mills | |
| 6,491,927 B1 | 12/2002 | Arnaud et al. | |
| 6,503,761 B1 | 1/2003 | Koenig et al. | |
| 6,515,717 B1 * | 2/2003 | Jiang | B41M 3/00 |
| | | | 347/101 |
| 6,517,628 B1 | 2/2003 | Pfaff et al. | |
| 6,517,818 B1 | 2/2003 | Golz-Berner et al. | |
| 6,545,809 B1 | 4/2003 | Phillips | |
| 6,582,684 B1 | 6/2003 | Abrahamson | |
| 6,589,331 B2 * | 7/2003 | Ostertag | A61Q 1/02 |
| | | | 106/403 |
| 6,645,286 B2 | 11/2003 | Ostertag et al. | |
| 6,669,389 B2 | 12/2003 | Gueret | |
| 6,679,825 B2 | 1/2004 | Alicea | |
| 6,686,397 B2 | 2/2004 | Jaehne et al. | |
| 6,753,002 B2 | 6/2004 | George et al. | |
| 6,846,474 B2 | 1/2005 | Nayfeh et al. | |
| 6,884,289 B2 | 4/2005 | Schoen et al. | |
| 7,056,498 B2 | 6/2006 | Chevalier et al. | |
| 7,060,371 B2 | 6/2006 | Akiyama et al. | |
| 7,168,874 B2 | 1/2007 | Gueret | |
| 7,258,900 B2 | 8/2007 | Raksha et al. | |
| 7,270,770 B2 | 9/2007 | Sage et al. | |
| 7,306,809 B2 | 12/2007 | Sojka et al. | |
| 7,329,287 B2 | 2/2008 | Simonet et al. | |
| 7,329,719 B2 | 2/2008 | Pavlin | |
| 2001/0022025 A1 | 9/2001 | Skipper | |
| 2001/0033766 A1 | 10/2001 | Gueret | |
| 2002/0012683 A1 | 1/2002 | Henrion et al. | |
| 2002/0015965 A1 | 2/2002 | Sweeting | |
| 2002/0031870 A1 | 3/2002 | Bryant | |
| 2002/0039562 A1 | 4/2002 | Kobayashi et al. | |
| 2002/0041853 A1 | 4/2002 | Ishii et al. | |
| 2002/0064509 A1 | 5/2002 | Grimm et al. | |
| 2002/0070121 A1 | 6/2002 | Nayfeh et al. | |
| 2002/0117084 A1 | 8/2002 | Hayashi et al. | |
| 2002/0134282 A1 | 9/2002 | Ostertag et al. | |
| 2002/0164192 A1 | 11/2002 | Gueret | |
| 2002/0169244 A1 | 11/2002 | Ostertag et al. | |
| 2002/0182383 A1 | 12/2002 | Phillips et al. | |
| 2002/0182409 A1 * | 12/2002 | Gueret | A46B 13/001 |
| | | | 428/364 |
| 2002/0192448 A1 | 12/2002 | Schoen et al. | |
| 2003/0007942 A1 | 1/2003 | Koenig | |
| 2003/0012752 A1 | 1/2003 | Bara | |
| 2003/0017124 A1 | 1/2003 | Agostini et al. | |
| 2003/0031870 A1 | 2/2003 | Argoitia et al. | |
| 2003/0039621 A1 | 2/2003 | Arnaud et al. | |
| 2003/0064039 A1 | 4/2003 | Kolodziej et al. | |
| 2003/0064086 A1 | 4/2003 | Carrion et al. | |
| 2003/0072602 A1 | 4/2003 | Gueret | |
| 2003/0082121 A1 * | 5/2003 | Borsakian | A61K 8/19 |
| | | | 424/61 |
| 2003/0118531 A1 | 6/2003 | Kolodziej et al. | |

(56) References Cited

U.S. PATENT DOCUMENTS

| | | |
|---|---|---|
| 2003/0130323 A1 | 7/2003 | Jaehne et al. |
| 2003/0134761 A1 | 7/2003 | Sebillotte-Arnaud et al. |
| 2003/0180232 A1 | 9/2003 | Ishii et al. |
| 2003/0180535 A1 | 9/2003 | Horino et al. |
| 2003/0228339 A1 | 12/2003 | El-Nokaly et al. |
| 2004/0001869 A1 | 1/2004 | Yago et al. |
| 2004/0009309 A1* | 1/2004 | Raksha ................ B05D 3/207 427/598 |
| 2004/0012683 A1 | 1/2004 | Yamasaki et al. |
| 2004/0105827 A1 | 6/2004 | Grimm et al. |
| 2004/0109837 A1 | 6/2004 | Mellul et al. |
| 2004/0175338 A1 | 9/2004 | Filippi et al. |
| 2004/0228818 A1 | 11/2004 | Simon et al. |
| 2004/0228890 A1 | 11/2004 | Blin et al. |
| 2004/0241118 A1 | 12/2004 | Simon et al. |
| 2005/0025728 A1 | 2/2005 | De Rigal et al. |
| 2005/0036964 A1 | 2/2005 | Camus et al. |
| 2005/0118122 A1 | 6/2005 | Simon et al. |
| 2005/0191337 A1 | 9/2005 | Gueret |
| 2005/0238979 A1 | 10/2005 | Dumousseaux |
| 2005/0249540 A1 | 11/2005 | Gueret |
| 2005/0257335 A1 | 11/2005 | Dumousseaux |
| 2005/0257715 A1 | 11/2005 | Dumousseaux |
| 2005/0260146 A1 | 11/2005 | Blin |
| 2005/0276767 A1 | 12/2005 | Blin et al. |
| 2006/0018854 A1 | 1/2006 | Dumousseaux et al. |
| 2006/0039876 A1 | 2/2006 | Dumousseaux et al. |
| 2006/0041054 A1 | 2/2006 | Dumousseaux et al. |
| 2006/0051382 A1 | 3/2006 | Vidal |
| 2006/0088484 A1 | 4/2006 | Thevenet |
| 2006/0099160 A1 | 5/2006 | Dumousseaux |
| 2006/0118663 A1 | 6/2006 | Herzing |
| 2006/0134044 A1 | 6/2006 | Blin et al. |
| 2006/0165621 A1 | 7/2006 | Dubertret et al. |
| 2006/0280705 A1 | 12/2006 | Bruechert et al. |
| 2006/0280764 A1 | 12/2006 | Watanabe et al. |
| 2007/0009454 A1 | 1/2007 | Thevenet |
| 2007/0231940 A1 | 10/2007 | Gourlaouen et al. |
| 2008/0014158 A1 | 1/2008 | Lion et al. |
| 2008/0044443 A1 | 2/2008 | Thevenet |
| 2008/0050324 A1 | 2/2008 | Thevenet |
| 2008/0105272 A1 | 5/2008 | Thevenet |
| 2008/0124288 A1 | 5/2008 | Thevenet |
| 2008/0127990 A1 | 6/2008 | Thevenet |
| 2009/0130037 A1 | 5/2009 | Thevenet et al. |

FOREIGN PATENT DOCUMENTS

| | | |
|---|---|---|
| DE | 102 19 296 | 11/2003 |
| EP | 0 096 459 A2 | 12/1983 |
| EP | 0 113 920 A2 | 7/1984 |
| EP | 0 080 976 B1 | 9/1986 |
| EP | 0 388 582 A2 | 9/1990 |
| EP | 0 412 704 A2 | 2/1991 |
| EP | 0 412 707 A1 | 2/1991 |
| EP | 0 416 747 A1 | 3/1991 |
| EP | 0 581 651 | 2/1994 |
| EP | 0 582 152 A2 | 2/1994 |
| EP | 0 587 908 | 3/1994 |
| EP | 0 686 675 A1 | 12/1995 |
| EP | 0 686 858 | 12/1995 |
| EP | 0 749 747 A1 | 12/1996 |
| EP | 0 815 836 A2 | 1/1998 |
| EP | 0921217 | 12/1998 |
| EP | 0 955 039 | 10/1999 |
| EP | 0 962 224 A2 | 12/1999 |
| EP | 1 043 018 A1 | 10/2000 |
| EP | 1 101 486 | 5/2001 |
| EP | 1 184 426 A2 | 3/2002 |
| EP | 1 217 046 A2 | 6/2002 |
| EP | 1 249 222 A1 | 10/2002 |
| EP | 1 264 562 | 12/2002 |
| EP | 1 318 184 A1 | 6/2003 |
| EP | 1 382 323 | 1/2004 |
| EP | 1 410 786 A1 | 4/2004 |
| EP | 1 411 069 A2 | 4/2004 |
| EP | 1 424 372 | 6/2004 |
| EP | 1 440 681 A1 | 7/2004 |
| EP | 1 510 502 | 3/2005 |
| EP | 1 591 035 | 11/2005 |
| FR | 2 077 143 | 10/1971 |
| FR | 2 232 303 | 1/1975 |
| FR | 2 268 512 | 11/1975 |
| FR | 2 393 573 | 1/1979 |
| FR | 2 594 130 | 8/1987 |
| FR | 2 758 697 | 7/1998 |
| FR | 2 845 277 | 4/2004 |
| FR | 2 845 899 | 4/2004 |
| FR | 2 846 277 | 4/2004 |
| FR | 2 847 812 | 6/2004 |
| FR | 2 848 821 | 6/2004 |
| FR | 2 848 826 | 6/2004 |
| FR | 2 850 271 | 7/2004 |
| FR | 2 851 463 | 8/2004 |
| FR | 2 876 011 | 4/2006 |
| GB | 1331819 | 9/1973 |
| GB | 1 510 674 | 5/1978 |
| GB | 2355987 A | 5/2001 |
| JP | 51-10959 | 4/1976 |
| JP | 51-137733 A | 11/1976 |
| JP | S-55-81809 | 6/1980 |
| JP | A-56-152411 | 11/1981 |
| JP | A-58-206610 | 12/1983 |
| JP | A-61-112008 | 5/1986 |
| JP | 63-175670 A | 7/1988 |
| JP | A-1-242513 | 9/1989 |
| JP | A-1-294611 | 11/1989 |
| JP | A-2-111340 | 4/1990 |
| JP | A-04-108710 | 8/1990 |
| JP | A-3-284613 | 12/1991 |
| JP | A-3-286463 | 12/1991 |
| JP | A-4-198117 | 7/1992 |
| JP | A-4-292664 | 10/1992 |
| JP | A-5-17710 | 1/1993 |
| JP | A-7-258460 | 10/1995 |
| JP | A-7-304633 | 11/1995 |
| JP | A-7-304997 | 11/1995 |
| JP | A-7-316015 | 12/1995 |
| JP | A-7-324015 | 12/1995 |
| JP | A-7-331109 | 12/1995 |
| JP | 8-38992 | 2/1996 |
| JP | A-8-127513 | 5/1996 |
| JP | A-9-188830 | 7/1997 |
| JP | A-10-87437 | 4/1998 |
| JP | A-10-158450 | 6/1998 |
| JP | A-10-158541 | 6/1998 |
| JP | A-2000-143490 | 11/1998 |
| JP | A-11-012493 | 1/1999 |
| JP | A-11-113631 | 4/1999 |
| JP | A-11-181329 | 7/1999 |
| JP | A-11-236312 | 8/1999 |
| JP | A-2000-168667 | 6/2000 |
| JP | A-2000-345096 | 12/2000 |
| JP | A-2001-61550 | 3/2001 |
| JP | A-2001-270805 | 10/2001 |
| JP | A-2001-299443 | 10/2001 |
| JP | A-2001-302432 | 10/2001 |
| JP | A-2002-114640 | 4/2002 |
| JP | A-2002-138010 | 5/2002 |
| JP | A-2002-188021 | 7/2002 |
| JP | A-2002-194349 | 7/2002 |
| JP | A-2002-322020 | 11/2002 |
| JP | A-2002-363440 | 12/2002 |
| JP | A-2003-000338 | 1/2003 |
| JP | A-2003-2634 | 1/2003 |
| JP | A-2003-24133 | 1/2003 |
| JP | A-2003-55575 | 2/2003 |
| JP | A-2003-125846 | 5/2003 |
| JP | A-2003-128932 | 5/2003 |
| JP | A-2003-160438 | 6/2003 |
| JP | A-203-199620 | 7/2003 |
| JP | A-2004-043367 | 2/2004 |
| JP | A-2004-043656 | 2/2004 |

(56) References Cited

FOREIGN PATENT DOCUMENTS

| | | |
|---|---|---|
| JP | A-2004-059746 | 2/2004 |
| JP | A-2004-123681 | 4/2004 |
| JP | A-2004-131484 | 4/2004 |
| JP | A-2004-512348 | 4/2004 |
| JP | A-2004-137280 | 5/2004 |
| JP | A-2004-231610 | 8/2004 |
| JP | A-2004-307424 | 11/2004 |
| JP | A-2005-68323 | 3/2005 |
| JP | A-2005-516890 | 6/2005 |
| JP | A-2005-232152 | 9/2005 |
| WO | WO 93/23009 | 11/1993 |
| WO | WO 93/23446 | 11/1993 |
| WO | WO 94/26729 | 11/1994 |
| WO | WO 95/00578 | 1/1995 |
| WO | WO 95/03776 | 2/1995 |
| WO | WO 95/06078 | 3/1995 |
| WO | WO 95/23537 | 9/1995 |
| WO | WO 96/19347 | 6/1996 |
| WO | WO 97/35541 | 10/1997 |
| WO | WO 99/32076 | 7/1999 |
| WO | WO 99/36477 | 7/1999 |
| WO | WO 99/36478 | 7/1999 |
| WO | WO 01/38222 A1 | 5/2001 |
| WO | WO 02/28356 | 4/2002 |
| WO | WO 02/053114 | 7/2002 |
| WO | WO 03/016429 A1 | 2/2003 |
| WO | WO 03/020225 A1 | 3/2003 |
| WO | WO 03020255 A1 | 3/2003 |
| WO | WO 2004/000244 | 12/2003 |
| WO | WO 2004/007096 | 1/2004 |
| WO | WO 2004/009044 | 1/2004 |
| WO | WO 2004/026972 A1 | 4/2004 |
| WO | WO 2004/028488 | 4/2004 |
| WO | WO 2004028490 A2 | 4/2004 |
| WO | WO 2006/027494 | 3/2006 |
| WO | WO 2006/037900 | 4/2006 |
| WO | WO 2006/037902 A1 | 4/2006 |
| WO | WO 2006/037903 | 4/2006 |
| WO | WO 2006/037906 | 4/2006 |
| WO | WO 2006/054002 | 5/2006 |

OTHER PUBLICATIONS

"Graft Copolymers with Short Side Chains," Polymer Letters, 1967, vol. 5, pp. 477-481.
Goubault, "Colloides magnetiques: auto-organisation et applications biologiques," Doctoral Thesis of the University of Paris VI, Mar. 23, 2004.
U.S. Appl. No. 11/663,975, filed Aug. 16, 2007, Ludovic Thevenet.
U.S. Appl. No. 11/664,003, filed Aug. 16, 2007, Ludovic Thevenet.
U.S. Appl. No. 11/663,772, filed Aug. 16, 2007, Ludovic Thevenet.
U.S. Appl. No. 11/663,776, filed Aug. 16, 2007, Ludovic Thevenet.
U.S. Appl. No. 11/663,978, filed Aug. 16, 2007, Ludovic Thevenet.
Pradyot Patnaik, Handbook of Inorganic Chemicals (2003), p. 945.
Oct. 19, 2009 Office Action issued in U.S. Appl. No. 11/663,776.
Oct. 21, 2009 Office Action issued in U.S. Appl. No. 11/664,003.
Oct. 27, 2009 Office Action issued in U.S. Appl. No. 11/663,978.
French Search Report for French Patent Application No. FR 04/50712, priority document for co-pending U.S. Appl. No. 11/100,513, Nov. 9, 2004.
French Search Report for French Patent Application No. FR 04/50713, priority document for co-pending U.S. Appl. No. 11/100,566, Nov. 23, 2004.
French Search Report for French Patent Application No. FR 04/50714, priority document for co-pending U.S. Appl. No. 11/100,509, Nov. 10, 2004.
French Search Report for French Patent Application No. FR 04/50715, priority document for co-pending U.S. Appl. No. 11/100,514, Nov. 23, 2004.
Aug. 4, 2010 Office Action issued in U.S. Appl. No. 11/663,978.
Oct. 17, 2008 Chinese Office Action issued in Chinese Patent Application No. 200610111595.3.
Jul. 23, 2010 Office Action issued in U.S. Appl. No. 11/663,975.
International Search Report for PCT Application No. PCT/IB03/04306, priority document for co-pending U.S. Appl. No. 10/529,872, dated Match 3, 2004.
International Search Report for PCT/FR2005/050557, priority document for co-pending U.S. Appl. No. 11/242,901, Feb. 10, 2006.
Dec. 28, 2006 Office Action issued in U.S. Appl. No. 11/100,509.
U.S. Appl. No. 11/242,900, filed Oct. 5, 2005, Ludovic Thevenet.
U.S. Appl. No. 11/242,901, filed Oct. 5, 2005, Ludovic Thevenet.
U.S. Appl. No. 11/482,165, filed Jul. 7, 2006, Ludovic Thevenet.
U.S. Appl. No. 11/511,324, filed Aug. 9, 2006, Marc Ramet.
U.S. Appl. No. 11/922,411, filed Jun. 17, 2008, Ludovic Thevenet.
Apr. 13, 2006 French Search Report issued in FR 0552125.
May 14, 2009 Office Action issued in U.S. Appl. No. 11/482,165.
Dec. 10, 2008 Office Action issued in U.S. Appl. No. 11/482,165.
Feb. 11, 2009 Office Action issued in U.S. Appl. No. 11/663,978.
Jun. 9, 2010 Office Action issued in U.S. Appl. No. 11/664,003.
Apr. 29, 2010 Office Action issued in U.S. Appl. No. 11/663,772.
U.S. Appl. No. 10/529,872, filed Oct. 12, 2005, Christophe Dumousseaux.
U.S. Appl. No. 11/100,509, filed Apr. 7, 2005, Christophe Dumousseaux.
U.S. Appl. No. 11/100,513, filed Apr. 7, 2005, Christophe Dumousseaux.
U.S. Appl. No. 11/100,514, filed Apr. 7, 2005, Xavier Blin.
U.S. Appl. No. 11/100,566, filed Apr. 7, 2005, Christophe Dumousseaux.
U.S. Appl. No. 11/101,398, filed Apr. 8, 2005, Christophe Dumousseaux.
U.S. Appl. No. 11/101,399, filed Apr. 8, 2005, Christophe Dumousseaux.
U.S. Appl. No. 11/101,400, filed Apr. 8, 2005, Christophe Dumousseaux.
U.S. Appl. No. 11/770,177, filed Jun. 28, 2007, Christophe Dumousseaux.
Aug. 16, 2007 of Action issued in U.S. Appl. No. 11/101,400.
Jan. 15, 2009 Office Action issued in U.S. Appl. No. 11/100,514.
Jan. 21, 2016 Office Action issued in U.S. Appl. No. 11/242,901.
Jan. 22, 2009 Office Action issued in U.S. Appl. No. 11/101,400.
Jan. 27, 2009 Office Action issued in U.S. Appl. No. 11/770,177.
Jan. 7, 2009 Office Action issued in U.S. Appl. No. 11/100,566.
Jan. 8, 2009 Office Action issued in U.S. Appl. No. 11/242,901.
Jul. 10, 2009 Office Action issued in U.S. Appl. No. 11/770,177.
Jul. 7, 2009 Office Action issued in U.S. Appl. No. 11/242,901.
Jul. 9, 2009 Office Action issued in U.S. Appl. No. 11/100,566.
Jun. 23, 2008 Office Action issued in U.S. Appl. No. 11/101,399.
Jun. 23, 2008 Office Action issued in U.S. Appl. No. 11/242,901.
Jun. 24, 2008 Office Action issued in U.S. Appl. No. 11/100,566.
Jun. 24, 2008 Office Action issued in U.S. Appl. No. 11/770,177.
Jun. 26, 2008 Office Action issued in U.S. Appl. No. 11/101,398.
Mar. 19, 2009 Office Action issued in U.S. Appl. No. 11/101,398.
Mar. 19, 2004 Office Action issued in U.S. Appl. No. 11/101,399.
Match 20, 2008 Office Action issued in U.S. Appl. No. 11/101,400.
May 21, 2009 Office Action issued in U.S. Appl. No. 11/100,513.
Nov. 9, 2009 Office Action issued in U.S. Appl. No. 11/101,400.
Oct. 1, 2009 Office Action issued in U.S. Appl. No. 11/101,398.
Oct. 26, 2009 Office Action issued in U.S. Appl. No. 11/100,513.
Sep. 24, 2009 Office Action issued in U.S. Appl. No. 11/101,399.
Titanium Dioxide—Wikipedia (http://en.wikipedia.org/wikiTitanium_dioxide.retrieved online on Aug. 10, 2010).
Apr. 27, 2010 Office Action issued in U.S. Appl. No. 11/770,177.
Apr. 28, 2010 Office Action issued in U.S. Appl. No. 11/100,566.
Aug. 26, 2009 Office Action issued in U.S. Appl. No. 11/511,324.
Craft Master, advertisement, 1975.
May 31, 2006 French Search Report issued in FR 0552609.
International Cosmetic Ingredient Dictionary Handbook, 1997 Edition, pp. 371-386.
International Cosmetic Ingredient Dictionary Handbook, 1997 Edition, pp. 524-528.
Feb. 20, 2006 International Search Report issued in PCT/FR2005/050557.
Dec. 11, 2006 European Search Report issued in EP 06 30 0902.
Mar. 17, 2010 Office Action issued in U.S. Appl. No. 11/511,324.

(56) References Cited

OTHER PUBLICATIONS

Dec. 19, 2006 International Search Report issued in PCT/IB2006/052239.
Jun. 30, 2010 Office Action issued in U.S. Appl. No. 11/663,776.
Sep. 16, 2010 Office Action issued in U.S. Appl. No. 11/511,324.
Japanese Office Action with English-language translation for Japanese Application No. 2007-534054 mailed Oct. 7, 2010.
Jan. 18, 2011 Restriction Requirement issued in U.S. Appl. No. 11/922,411.
Dec. 27, 2010 Office Action issued in U.S. Appl. No. 11/663,978.
Dec. 27, 2010 Office Action issued in U.S. Appl. No. 11/663,772.
Dec. 28, 2010 Office Action issued in U.S. Appl. No. 11/663,975.
Feb. 11, 2011 Office Action issued in U.S. Appl. No. 11/663,776.
Feb. 11, 2011 Office Action issued in U.S. Appl. No. 11/664,003.
Mar. 25, 2011 Japanese Office Action issued in Japanese Patent Application No. 2007-535205 (with translation).
Feb. 15, 2011 Japanese Office Action issued in Japanese Patent Application No. 2007-535206 (with translation).
Feb. 15, 2011 Japanese Office Action issued in Japanese Patent Application No. 2007-535204 (with translation).
Jan. 13, 2011 Japanese Office Action issued in Japanese Patent Application No. 2007-534055 (with translation).
Jan. 13, 2011 Japanese Office Action issued in Japanese Patent Application No. 2007-534056 (with translation).
May 24, 2011 Office Action issued in U.S. Appl. No. 11/922,411.
Jan. 18, 2012 Office Action issued in U.S. Appl. No. 11/922,411.
Dec. 22, 2011 Office Action issued in U.S. Appl. No. 11/511,324.
Definition of "soft iron", Collins English Dictionary, $5^{th}$ edition (2000).
Aug. 22, 2011 Office Action issued in U.S. Appl. No. 11/663,772.
Aug. 23, 2011 Office Action issued in U.S. Appl. No. 11/663,776.
Aug. 22, 2011 Office Action issued in U.S. Appl. No. 11/663,975.
Aug. 22, 2011 Office Action issued in U.S. Appl. No. 11/663,978.
Aug. 17, 2011 Office Action issued in U.S. Appl. No. 11/664,003.
Notice of the Reasons for Rejection for corresponding Japanese Patent Application No. 2007-535207, mailed Apr. 4, 2011 (with English translation).
Apr. 12, 2012 Office Action issued in U.S. Appl. No. 11/663,978.
Mar. 29, 2012 Office Action issued in U.S. Appl. No. 11/663,975.
Apr. 4, 2012 Office Action issued in U.S. Appl. No. 11/663,776.
Mar. 29, 2012 Office Action issued in U.S. Appl. No. 11/663,772.
Apr. 6, 2012 Office Action issued in U.S. Appl. No. 11/664,003.
Jan. 19, 2012 Japanese Office Action issued in Japanese Patent Application No. 2008-520040 (with translation).
Nov. 26, 2012 Office Action issued in U.S. Appl. No. 11/663,772.
Dye, Renee; "The Buzz on Buzz," Harvard Business Review, Nov.-Dec. 2000, issue, pp. 139-146.
Office Action mailed Dec. 21, 2010, in co-pending U.S. Appl. No. 11/101,400.
Office Action mailed Dec. 23, 2010, in co-pending U.S. Appl. No. 11/242,900.
Office Action mailed Aug. 3, 2010, in co-pending U.S. Appl. No. 11/101,399.
Office Action mailed Aug. 4, 2010, in co-pending U.S. Appl. No. 11/101,398.
Office Action mailed May 11, 2010, in co-pending U.S. Appl. No. 11/100,513.
Office Action mailed May 11, 2010, in co-pending U.S. Appl. No. 11/101,400.
Office Action issued Aug. 13, 2012 in U.S. Appl. No. 11/511,324.
Office Action issued Aug. 30, 2012 in U.S. Appl. No. 11/663,776.
Office Action issued Aug. 30, 2012 in U.S. Appl. No. 11/663,978.
Office Action issued Aug. 30, 2012 in U.S. Appl. No. 11/664,003.
Office Action issued Aug. 30, 2012 in U.S. Appl. No. 11/242,901.
Kurtus, Ron; "Detection of a Magnetic Field," dated May 23, 2004, as captured by internet archive (<web.archive.org>) on Jun. 4, 2004 from www.school-for-champions.com/science/magnetic_detection.htm, pp. 1-5 as provided.
Roeben, Scott; "Ferreting Out Funny Money: Fighting Counterfeiting, " as captured by internet archive (<web.archive.org>) on Feb. 3, 2004 from <dribbleglass.com/subpages/counterfeit.htm>, pp. 1-7 as provided.
Drab!, Carmen; "Nail Polish", 2008, American Chemical Society, Chemical & Engineering News, vol. 86, No. 32, p. 32 (pp. 1-2 as supplied).
Blakely, Richard J.; "Potential Theory in Gravity and Magnetic Applications," 1996, Cambridge University Press; pp. 87-90.
Merriam-Webster™ "Merriam-Webster's Collegiate Dictionary, 11th edition," 2003; Merriam-Websters Inc; entry for "cosmetic," pp. 1-20.
21-USC-Chapter-9-subchapter-11, definition of "cosmetic," p. 32.
Co-pending U.S. Appl. No. 11/770,177, filed Jun. 28, 2007.
U.S. Appl. No. 11/663,977, filed Mar. 28, 2007, Ludovic Thevenet et al.
Notice of Allowance mailed on co-pending U.S. Appl. No. 11/101,400, dated Apr. 27, 2011.
Notice of Allowance mailed on co-pending U.S. Appl. No. 11/100,513, dated Mar. 9, 2011.
Argoitia, A. et al., "Pigments Exhibiting Diffractive Effects", Society of Vacuum Coaters, $45^{th}$ Annual Technical Conference Proceedings, pp. 539-545, (2002).
French Search Report for French Patent Application No. FR 05/52124, May 24, 2006.
Office Action mailed Dec. 21, 2010, in co-pending U.S. Appl. No. 11/100,513.
Mar. 8, 2013 Japanese Office Action issued in Japanese Application No. 2008-520040.
Apr. 25, 2013 Office Action issued in U.S. Appl. No. 11/663,772.

\* cited by examiner

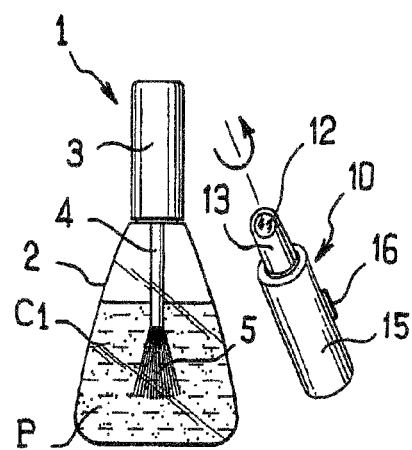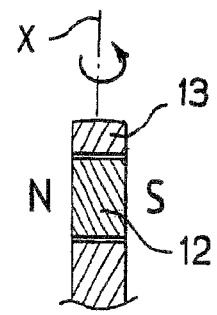
FIG.1  FIG.2
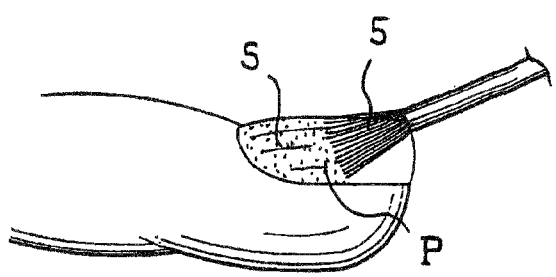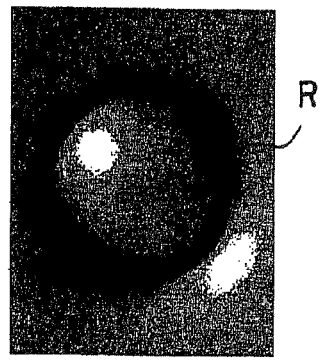
FIG.3
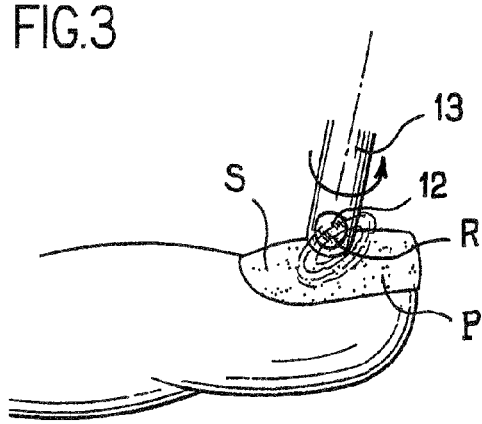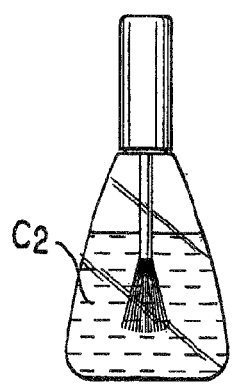
FIG.4  FIG.5  FIG.6

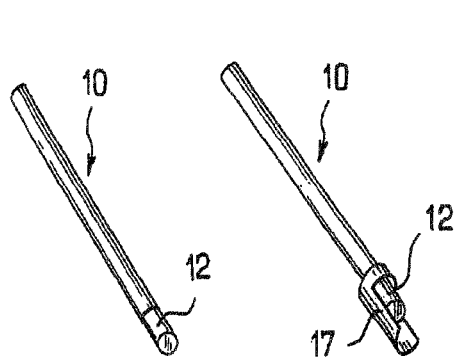
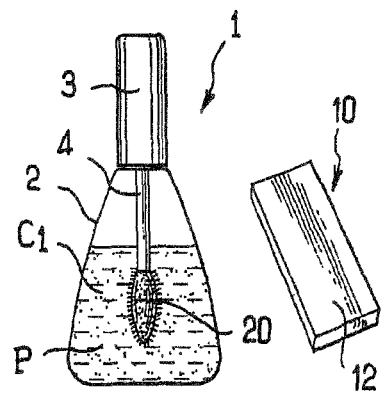
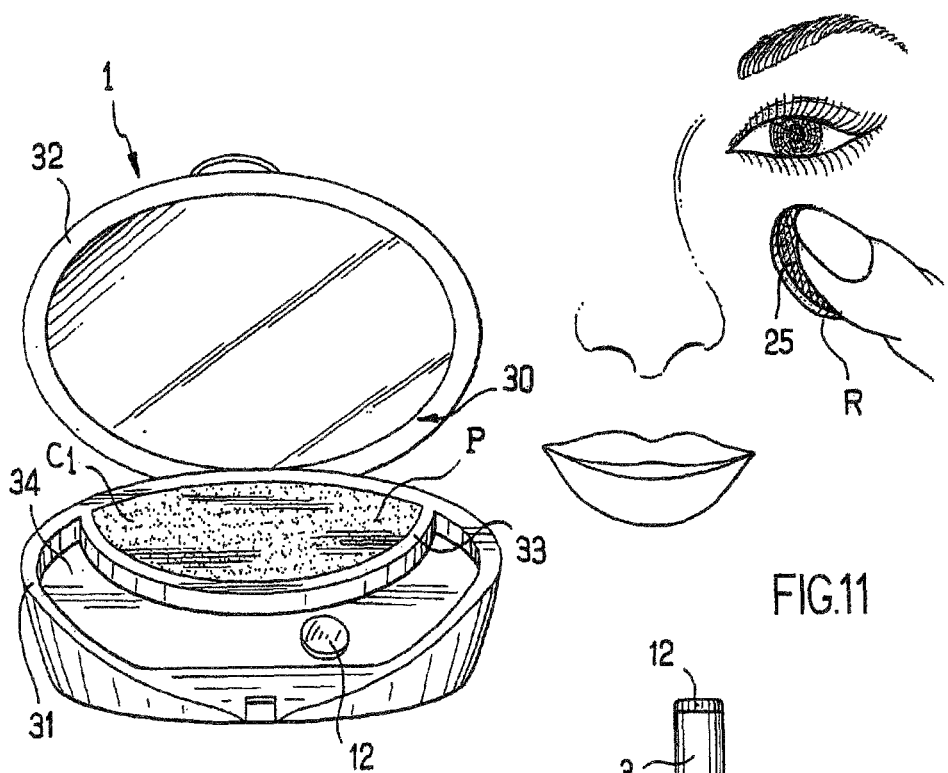
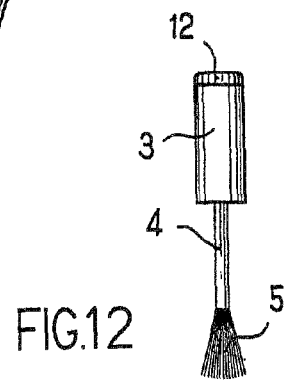
FIG.7  FIG.8  FIG.9  FIG.10  FIG.11  FIG.12

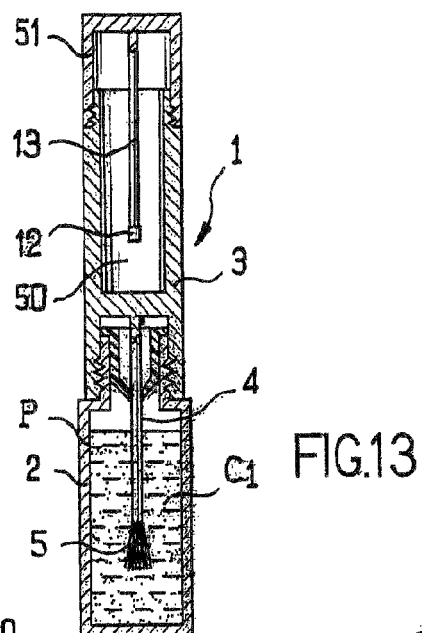
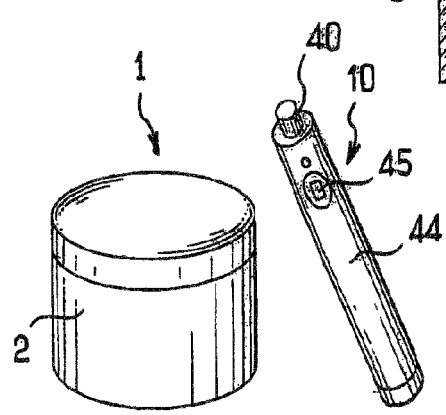
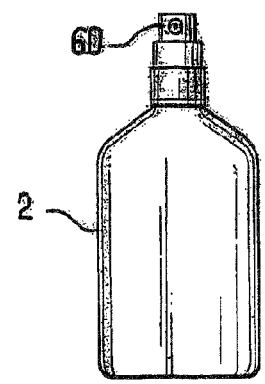
FIG.13
FIG.14
FIG.15
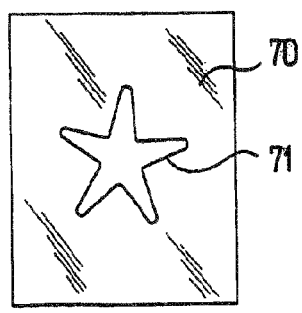
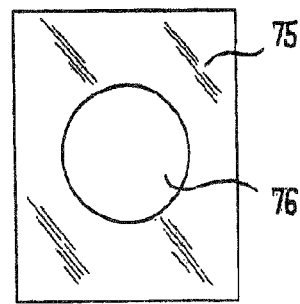
FIG.16
FIG.17

METHOD OF APPLYING MAKEUP TO A SURFACE AND A KIT FOR IMPLEMENTING SUCH A METHOD

CROSS-REFERENCE TO RELATED APPLICATIONS

The present application is a continuation-in-part of U.S. application Ser. No. 11/242,901, which is the National Stage of International Application No. PCT/FR05/50557, filed Jul. 8, 2005, which claims priority to French Application No. FR 04 10501, filed Oct. 5, 2004, including the subject matter of U.S. application Ser. Nos. 11/242,900, 11/663,977, 11/664,003, 11/663,978 and 11/663,776, which are the National Stage of International Applications No. PCT/FR05/50558, PCT/FR05/50563, PCT/FR05/50560, PCT/FR05/50559 and PCT/FR05/50564, respectively, all filed Jul. 8, 2005; claiming priority to French Applications No. FR 04 10509, FR 04 10501, FR 04 10501, FR 04 10501, and FR 04 10501, respectively, all filed Oct. 5, 2004. The contents of these applications are fully incorporated herein by reference.

BACKGROUND OF THE INVENTION

The present invention relates to a method of applying makeup to a surface, such as the skin, the nails, hair, e.g. the eyelashes, the lips, or even false nails, and it also relates to various kits for implementing such a method.

The term "cosmetic composition" as used in the context of the present invention means a composition as defined in the Jun. 14, 1993 EEC Directive 93/35 modifying EEC Directive 76/768. Foundations, lipsticks, and nail varnishes are examples of cosmetic compositions.

BRIEF SUMMARY OF THE INVENTION

A need exists to benefit from novel appearance effects in the field of makeup and the invention seeks to satisfy that need.

A particular problem posed with such compositions is long-term durability of the optical effect obtained.

In this context, the invention seeks to propose a composition for applying to keratinous substances, in particular the skin or the lips, that enables a durable result of optical effects to be obtained.

A Method of Applying Makeup

According to one of its aspects, the invention provides a method of applying makeup to a surface, such as the skin, the nails, hair, or the lips, which method comprises the following steps:
  depositing at least a first cosmetic composition in the fluid state on the surface, said first composition containing magnetic particles that are movable under the effect of a magnetic field; and
  exposing at least part of the first composition to a magnetic field, so as to orientate and/or displace at least a fraction of the magnetic particles.

Exposure to the magnetic field can modify the appearance of the first composition.

Thus, the method may include the step consisting in exposing at least part of the first composition to a magnetic field, so as to orientate and/or displace at least a fraction of the magnetic particles, and so as to modify the appearance of the first composition.

The magnetic field may be applied so as to form at least one pattern on the first composition, said pattern being linked to the shape of the field lines, for example.

The invention thus makes it possible to create novel makeup effects with a single cosmetic composition, enabling patterns in relief to be produced, for example, or imparting an impression of relief or various other possibly geometrical patterns.

The magnetic field may also be applied so as to model the clarity and/or the color of at least a region of the face or of the body to which the first composition has been applied.

For example, when the first cosmetic composition is a foundation, orienting the particles under the effect of the magnetic field makes it possible to modify the clarity of the first composition and thus to model the appearance of the face in the regions exposed to the magnetic field, in particular so as to apply makeup of cameo type, without sharp transitions between the light regions and the dark regions if so desired. By way of example, the magnetic field may be applied so as to darken the sides of the face, so as to make it appear thinner than it really is.

In an implementation of the invention, a layer of a second cosmetic composition is applied to the first with a view to obtaining a depth, gloss, smoothness, or other effect, for example. The second composition may be transparent and may optionally be colored. By way of example, the second composition may be for application to the lips or to the nails. The second composition may also be applied to the surface before the first composition, so as to create a colored base, or so as to improve the retention and/or the comfort of the first composition, for example.

Thus, according to a first of its aspects, the invention also provides a method of applying makeup to a surface, such as the skin, the nails, hair, or the lips, which method comprises the following steps:
  depositing at least first and second cosmetic compositions in the fluid state on the surface, the first composition covering or being covered by the second composition, the first composition containing magnetic particles that are movable under the effect of a magnetic field; and
  exposing at least part of the first composition to a magnetic field, so as to orientate and/or displace at least a fraction of the magnetic particles, and so as to modify the appearance of the first composition.

Exposure to the magnetic field can take place before and/or after the second composition has been applied to the surface or to the first composition.

When the second cosmetic composition is applied to the first, it makes it possible to obtain a depth, gloss, smoothness, or other effect. The second composition may be transparent. The second composition may alternatively be covered by the first, so as to create a colored background/base, for example.

By way of example, the second composition may be for application to the lips or to the nails.

According to a second of its aspects, the invention provides a method of applying makeup to a surface, such as the skin, the nails, hair, or the lips, especially the skin and lips, comprising the following steps:
  a) depositing at least a first cosmetic composition in the fluid state on the surface, said first composition comprising:
    i) at least one volatile solvent, especially a volatile oil; and
    ii) magnetic particles that are movable under the effect of a magnetic field; and
  b) exposing at least part of the first composition to, a magnetic field so as to orientate and/or displace at least a fraction of the magnetic particles.

The presence of at least one volatile solvent, especially a volatile oil, is advantageous since immediately after application it endows the magnetic particles with a certain mobility under the effect of a magnetic field, and following a certain drying period, it also immobilizes those particles in the orientation imposed upon them.

Advantageously, the composition includes at least one film-forming polymer, which can further enhance immobilization of the particles after drying.

According to a third of its aspects, the invention provides a method of applying makeup to a surface, in particular the skin, the lips, the nails, or hair, the method comprising the following steps:

depositing at least a first cosmetic composition on the surface, said first cosmetic composition comprising:
magnetic particles that are movable under the effect of a magnetic field; and
at least one coloring agent having optical properties that are sensitive to an external stimulus; and
exposing at least part of the first composition to a magnetic field so as to orientate and/or displace at least a fraction of the magnetic particles.

The invention allows novel esthetic effects to be created, for example by combining effects linked to orientation and/or a displacement of the magnetic particles and to the coloring agent that is sensitive to an external stimulus.

The coloring agent that is sensitive to an external stimulus may change form chemically in response to the external stimulus. The coloring agent may also keep the same chemical form and pass into an excited state in response to the external stimulus.

The external stimulus may be light radiation, a temperature variation, or a mechanical or chemical action.

The particles that are movable under the effect of a magnetic field, also termed magnetic particles, may be composed at least in part by the coloring agent that is sensitive to an external stimulus, or they may be different therefrom.

According to this third aspect, where a pattern is formed, said pattern may be permanently visible or may appear only under certain conditions connected with the coloring agent having optical properties that are sensitive to an external stimulus.

As an example, under certain environmental conditions, the pattern may be more visible. The coloring agent that is sensitive to an external stimulus may, for example, have a highly saturated color under certain conditions, which renders a pattern connected with a particular orientation of at least one magnetic pigment difficult to see. Under other environmental conditions, the color of the coloring agent is less saturated or even non-existent, and the pattern becomes clear or easier to see.

When the coloring agent that is sensitive to an external stimulus is a thermochromic or photochromic agent, the pattern may, for example, appear or disappear as a function of the temperature or intensity of UV radiation.

The coloring agent may also be luminescent, for example mechanoluminescent, phosphorescent, or fluorescent.

At least one coloring agent that is sensitive to an external stimulus may be fixed to a magnetic body. Said coloring agent may, for example, coat a magnetic body at least in part, it may be mixed with or form a matrix loaded with magnetic particles, or it may be grafted to a magnetic particles.

According to a fourth of its aspects, the invention provides a method of applying makeup to a surface, in particular the skin, the lips, the nails, or hair, the method comprising the following steps:

depositing at least a first cosmetic composition on the surface to be made up, said first cosmetic composition comprising:
magnetic particles that are movable under the effect of a magnetic field; and
at least one diffractive pigment; and
exposing at least part of the composition to a magnetic field, so as to modify the orientation and/or displace at least some of the magnetic particles.

The magnetic particles may be different from the diffractive pigment, or, in a variant, the diffractive pigment may constitute all or some of the magnetic particles.

According to a fifth of its aspects, the invention provides a method of applying makeup to a surface, in particular such as the skin, the lips, the nails, or hair, the method comprising:

depositing at least a first cosmetic composition on the surface, said first cosmetic composition comprising:
at least one magnetic particle that is movable under the effect of a magnetic field; and
at least one coloring agent producing a color by absorbing at least a fraction of the visible spectrum; and
exposing at least part of the first composition to a magnetic field, so as to orientate and/or displace at least a fraction of the magnetic particles, and so as to modify the appearance of the composition.

A color produced by absorbing light is sometimes also known as chemical color in contrast to colors produced by an interference phenomenon, including diffraction, also known as physical colors. The phenomenon of absorbing light energy by the coloring agent can rely on electron transitions.

When the magnetic particles contribute color, a change in their orientation under the effect of the magnetic field may lead to a change in the appearance of the composition.

When the magnetic particles are displaced, the shape of the deposit of composition may be affected, thereby enabling a portion in relief to be created, for example.

The composition need not be exposed to the magnetic field while the composition is being applied. The magnetic field may be exerted after the composition has been applied.

The magnetic field may be applied until the first composition obtains a fixed appearance, i.e. the appearance of said composition ceases to vary even if the magnetic field continues to exist. In a variant, the magnetic field may be applied for a period of time that is shorter than the period of time that causes all of the magnetic particles in the exposed region to be permanently displaced and/or oriented.

Since the clarity and/or the color of the first composition change progressively under the effect of the magnetic field, the user can stop subjecting the magnetic particles to the field when the first composition presents the desired appearance.

In an implementation of the invention, the magnetic field is exerted through a magnetic sheet. Depending on the shape of said sheet, the field lines will have different shapes, thereby making it possible to increase the number of patterns that can be produced with a single magnet, for example.

The magnetic field may be exerted successively on different regions of the surface that are coated with the first composition.

The magnetic field may be exerted on regions of the surface that are disjoint, so as to create separate patterns, for example.

A region of the surface coated with the first composition need not be exposed to the magnetic field, so as not to modify the appearance of the first composition in said region after it has been deposited.

Two regions of the surface may be exposed unequally to the magnetic field.

The first and second composition, if any, may be applied, independently from each other, in various ways, e.g. by means of a cosmetics applicator that is preferably non-magnetic for the first composition, and that is selected from brushes, flocked endpieces, and foams, woven fabrics, non-woven fabrics, or combs for example, or it may be applied without using an applicator, with the first and/or second composition, if any, being spread on with the fingers or sprayed on, for example.

In an implementation of the invention, the first and/or second composition, if any, is/are applied to the surface through a perforated mask. This makes it possible to produce a predetermined pattern corresponding to the shape of the perforation, for example. At least one region of the surface covered in the first composition may then be exposed to the magnetic field.

In a further aspect, the invention provides a cosmetic composition comprising:
    at least one volatile solvent, especially a volatile oil; and
    magnetic particles comprising metallic iron, optionally coated, especially soft iron.

Advantageously, the composition includes at least one film-forming polymer.

The presence of metallic iron ensures that the magnetic particles are highly sensitive to the magnetic field.

First Cosmetic Composition

After a given drying time, the first composition may take on a state that prevents the magnetic particles from further changing their orientation under the effect of a magnetic field. This applies to a nail varnish, for example. In some circumstances, the orientation of the magnetic particles may also be modified at any time, in particular when the first composition does not dry, or presents a very long drying time. This may apply to a foundation, for example.

As mentioned above, the first composition contains magnetic particles which may be presented in various forms.

Magnetic Particles

The term "magnetic particles", also termed as "magnetic bodies", means particles presenting magnetic susceptibility, i.e. particles that are sensitive to the action of a magnetic field, and that tend to come into alignment with the field lines, for example.

The expression "magnetic bodies" must not be understood in limiting manner and covers particles, fibers, or clumps of particles and/or fibers, of any shape, presenting non-zero magnetic susceptibility.

The first composition may contain both magnetic particles and non-magnetic particles.

The presence of magnetic particles and of non-magnetic particles in the composition makes it possible to create novel optical effects that can be modulated under the effect of a magnetic field, for example.

The applied composition may include magnetic fibers or other aspherical bodies, such as chains of particles or of fibers.

In the absence of a magnetic field, the magnetic particles used preferably do not present any remanent magnetism.

The magnetic particles may comprise any magnetic material that presents sensitivity to the lines of a magnetic field, regardless of whether the field is produced by a permanent magnet or is the result of induction, the material being selected from nickel, cobalt, iron, and alloys and oxides thereof, in particular $Fe_3O_4$, and also from gadolinium, terbium, dysprosium, erbium, and alloys and oxides thereof, for example. The magnetic material may be of the "soft" or of the "hard" type, and in particular may comprise metallic iron, in particular soft iron, which may optionally be coated.

The magnetic particles may optionally present a multilayer structure including at least one layer of a magnetic material such as iron, nickel, cobalt, and alloys and oxides thereof, in particular $Fe_3O_4$, for example.

The magnetic particles are preferably aspherical, presenting an elongate shape, for example. Thus, when the particles are subjected to the magnetic field, they tend to become oriented with their longitudinal axes in alignment with the field lines, and they are subjected to a change in orientation which results in the first composition changing in appearance.

When the magnetic particles are substantially spherical, their appearance is preferably non-uniform, so that a change in orientation results in a change in appearance.

The quantity of magnetic particles is sufficient to enable the appearance of the composition to depend on their orientation and/or on their positioning.

The concentration of magnetic particles may be in the range of about 0.05% to about 97% by weight, for example, and in particular in the range of about 0.1% to about 95% by weight, and preferably in the range of about 0.1% to about 90% by weight, e.g. about 3% by weight.

Where the first composition comprises at least one coloring agent having optical properties that are sensitive to an external stimulus, at least one diffractive pigment, or at least one coloring agent producing a color by absorbing at least a fraction of the visible spectrum, the concentration of magnetic bodies in the composition may be in the range of about 0.05% to about 50% by weight, for example, in particular in the range of about 0.1% to about 40% by weight, better in the range of 1% to about 30% by weight.

The size of the magnetic particles may be in the range 1 nanometer (nm) to 700 micrometers (μm), for example, preferably in the range 1 μm to 500 μm, and more preferably in the range 10 μm to 150 μm.

Where the first composition comprises at least one coloring agent having optical properties that are sensitive to an external stimulus, at least one diffractive pigment, or at least one coloring agent producing a color by absorbing at least a fraction of the visible spectrum, the size of the particles may be in the range of 1 nanometers (nm) to 10 millimeters (mm), for example, preferably in the range of 10 nm to 5 mm, and more preferably in the range of 100 nm to 1 mm, e.g. in the range of 0.5 micrometers (μm) to 300 μm or 1 μm to 150 μm, regardless of their form. When the bodies are particles that do not have an elongate shape, or that have an elongate shape with a relatively small form factor, the size of the particles may be less than 1 mm, for example.

The term "size" means the size given by the statistical grain size distribution at half the population, referred to as "D50".

Magnetic Pigments

The magnetic particles of the first composition may comprise magnetic pigments. The magnetic bodies are magnetic pigments, for example.

Particularly suitable pigments are nacres comprising iron oxide $Fe_3O_4$. By way of example, pigments presenting magnetic properties are those sold under the trade names COLORONA BLACKSTAR BLUE, COLORONA BLACKSTAR GREEN, COLORONA BLACKSTAR GOLD, COLORONA BLACKSTAR RED, CLOISONNE NU ANTIQUE SUPER GREEN, MICRONA MATTE BLACK (17437), MICA BLACK (17260), COLORONA PATINA SILVER (17289), and COLORONA PATINA GOLD (117288) by MERCK, or indeed FLAMENCO TWILIGHT RED, FLAMENCO TWILIGHT GREEN, FLAMENCO TWILIGHT GOLD, FLAMENCO TWILIGHT BLUE, TIMICA NU ANTIQUE SILVER 110 AB, TIMICA NU ANTIQUE GOLD 212 GB, TIMICA NU-ANTIQUE COPPER 340 AB, TIMICA NU ANTIQUE BRONZE 240 AB, CLOISONNE NU ANTIQUE GREEN 828 CB, CLOISONNE NU ANTIQUE BLUE 626 CB, GEMTONE MOONSTONE G 004, CLOISONNE NU ANTIQUE RED 424 CHROMA-LITE, BLACK (4498), CLOISONNE NU ANTIQUE ROUGE FLAMBE (code 440 XB), CLOISONNE NU ANTIQUE BRONZE (240 XB), CLOISONNE NU ANTIQUE GOLD (222 CB), and CLOISONNE NU ANTIQUE COPPER (340 XB) by ENGELHARD.

Black iron oxide particles, e.g. those sold under the trade name SICOVIT noir E172 by BASF, or soft-iron based particles proposed under the trade name STAPA® WM IRON VP 041040 by ECKART, may also be mentioned.

Magnetic pigments may also comprise metallic iron, in particular passivated soft iron, e.g. obtained from carbonyl iron by implementing the method described in U.S. Pat. No. 6,589,331, the contents of which are incorporated herein by reference. The particles may include a surface oxide layer.

Magnetic Fibers

The magnetic particles may be fibers.

The term "fibers" means generally elongate bodies presenting, for example, a form factor in the range 3.5 to 2500 or 5 to 500, e.g. 5 to 150. The form factor is defined by the ratio L/D, where L is the length of the fiber and D is the diameter of the circle in which the widest cross-section of the fiber is inscribed.

By way of example, the cross-section of the fibers may be inscribed in a circle having a diameter in the range 2 nm to 500 µm, e.g. in the range 100 nm to 100 µm, or even 1 µm to 50 µm.

By way of example, the fibers may present a length in the range 1 µm to 10 millimeters (mm), e.g. 0.1 mm to 5 mm, or even 0.3 mm to 3.5 mm.

By way of example, the fibers may present a weight in the range 0.15 denier to 30 denier (weight in grams for 9 km of thread), e.g. 0.18 denier to 18 denier.

The cross-section of the fibers may be of any shape, e.g. circular, or polygonal, in particular square, hexagonal, or octagonal.

The composition may contain solid or hollow fibers that may be independent or interlinked, e.g. braided.

The composition may contain fibers having ends that are blunted and/or rounded, e.g. by polishing.

The shape of the fibers need not be significantly modified when they are inserted into the composition, with said fibers being initially rectilinear and sufficiently rigid to keep their shape. In a variant, the fibers may present flexibility that enables them to be substantially deformed within the composition.

The fibers may contain a non-zero amount, that may be as great as 100%, of a magnetic material selected from soft magnetic materials, hard magnetic materials, in particular based on iron, zinc, nickel, cobalt, or manganese, and alloys and oxides thereof, in particular $Fe_3O_4$, rare earths, barium sulfate, iron-silicon alloys, possibly containing molybdenum, $Cu_2MnAl$, $MnBi$, or a mixture thereof, this list not being limiting.

When the composition contains fibers containing magnetic particles, said magnetic particles may be present at least at the surface of the fibers, or only at the surface of the fibers, or only inside the fibers, or they may even be dispersed within the fibers in substantially uniform manner, for example.

By way of example, each fiber may include a non-magnetic core with a plurality of magnetic particles on its surface.

Each fiber may also include a synthetic matrix containing a plurality of magnetic grains dispersed therein.

Where appropriate, a synthetic material filled with magnetic particles may itself be covered by a non-magnetic membrane. By way of example, such a membrane constitutes a barrier isolating the magnetic material(s) from the surrounding environment and/or it can provide color. Each fiber may comprise a one-piece magnetic core and be covered by a non-magnetic membrane, or it may comprise a one-piece non-magnetic core and be covered by a magnetic membrane.

The composition may contain fibers made by extruding or co-extruding one or more polymeric materials, in particular thermoplastics and/or elastomers. One of the extruded materials may contain a filler of dispersed magnetic particles.

Each fiber may comprise a synthetic material selected from polyamides; polyethylene terephthalate (PET); acetates; polyolefins, in particular polyethylene (PE) or polypropylene (PP); polyvinyl chloride (PVC); polyester block amide; plasticized Rilsan®; elastomers, in particular polyester elastomers, polyethylene (PE) elastomers, silicone elastomers, nitrile elastomers; or a mixture of these materials, this list not being limiting.

The composition may contain composite fibers each comprising a magnetic core that is covered, at least in part, by at least one non-magnetic, synthetic, or natural material. By way of example, the magnetic core may be covered by co-extruding a membrane made of a non-magnetic material around the core.

The core may alternatively be covered in some other way, e.g. by polymerization in situ.

The core may be a single piece or it may include a filler of magnetic grains dispersed in a matrix.

The composition may also contain composite fibers obtained by covering a non-magnetic, synthetic, or natural core, with a synthetic material filled with magnetic particles, the core being composed of a fiber made of wood; rayon; polyamide; plant matter; or polyolefin, in particular polyethylene, Nylon®, polyimide-amide, or aramid, this list not being limiting.

The composition may also contain magnetic composite particles, in particular a magnetic latex.

Magnetic Composite Particles

A magnetic composite particle is a composite material constituted by an organic or an inorganic matrix and by magnetic grains. At their surfaces and/or within themselves, the magnetic composite particles may thus include grains of a magnetic material. The composite particles may be constituted by a magnetic core covered by an organic or an inorganic matrix, or they may be constituted by an organic or an inorganic core covered by a magnetic matrix.

The magnetic composite particles include one of the above-mentioned magnetic materials, for example.

The size of the magnetic composite particles may be in the range 1 nm to 1 mm, for example, preferably in the range 100 nm to 500 µm, and more preferably in the range 500 nm to 100 µm. The term "size" means the size given by the statistical grain size distribution at half the population, referred to as "D50".

The thesis by C. GOUBAULT, dated Mar. 23, 2004, and incorporated herein by reference, refers, in chapter 1, to the prior art on the subject of magnetic composite particles, and draws up a list of preparation methods that are suitable for being used to prepare magnetic composite particles, namely separately synthesizing the magnetic grains and the matrix, synthesizing the magnetic grains in contact with the matrix, or synthesizing the matrix in the presence of the magnetic grains.

KISKER markets inorganic-matrix magnetic composite particles composed of silica. DYNAL, SERADYN, ESTAPOR, and ADEMTECH propose organic-matrix magnetic composite particles that are also suitable for being used in the invention.

More particularly, under the reference M1-070/60, ESTAPOR markets magnetic latex constituted by grains of ferrite that are evenly distributed in a polystyrene matrix, said latex including 65% iron oxide, the mean diameter of the polystyrene particles being 890 nm, and the dry material mass content being 10%.

Ferrofluid

The first composition may contain a ferrofluid, i.e. a stable colloidal suspension of magnetic particles, in particular of magnetic nanoparticles.

The particles, having a size of the order of several tens of nanometers, for example, are dispersed in a solvent (water, oil, organic solvent), either by means of a surfactant or a dispersant, or by electrostatic interactions.

By way of example, the ferrofluids can be prepared by grinding ferrites or other magnetic particles until nanoparticles are obtained, which particles are then dispersed in a fluid containing a surfactant which is absorbed by the particles and stabilizes them, or else they can be prepared by precipitating a metallic-ion solution in a basic medium.

Each particle of the ferrofluid presents a magnetic moment that is determined by the size of the particle, and by the nature of the magnetic material.

Under the action of a magnetic field, the magnetic moments of the particles tend to come into alignment with the field lines, with non-zero magnetization appearing in the liquid. If the field is removed, there is no hysteresis and magnetization drops to zero.

Beyond a field threshold value, it is also possible to cause macroscopic changes in the liquid, e.g. the appearance of peaks, or a change in rheological properties.

The term "ferrofluid" also encompasses an emulsion of ferrofluid droplets in a solvent. Each drop thus contains colloidal magnetic particles in stable suspension. This makes it possible to have a ferrofluid in any type of solvent. The size of the magnetic particles in suspension in the ferrofluid may be in the range 1 nm to 10 µm, for example, preferably in the range 1 nm to 1 µm, and more preferably in the range 1 nm to 100 nm. The term "size" means the size given by the statistical grain size distribution at half the population, referred to as "D50".

Mention can be made in particular of ferrofluids sold by Liquids Research LTD under the references:

WHKS1S9 (A, B, or C), which is a water-based ferrofluid containing magnetite ($Fe_3O_4$), having particles of 10 nm in diameter.

WHJS1 (A, B, or C), which is an isoparaffin-based ferrofluid, containing magnetite ($Fe_3O_4$) particles that are 10 nm in diameter.

BKS25_dextran, which is a water-based ferrofluid stabilized by dextran, containing magnetite ($Fe_3O_4$) particles that are 9 nm in diameter.

Chains of Particles and/or of Magnetic Fibers

The composition may also contain chains of particles and/or of magnetic fibers.

The composition may thus contain clumps of particles or fibers having a largest dimension, e.g. length, that may, for example, be in the range 1 nm to 10 mm, e.g. in the range 10 nm to 5 mm, or in the range 100 nm to 1 mm, or even in the range 0.5 µm to 3.5 mm, e.g. in the range 1 µm to 150 µm. The term "size" means the size given by the statistical grain size distribution at half the population, referred to as "D50".

By way of example, chains of magnetic particles may be obtained by assembling colloidal magnetic particles, as described in the publications "Permanently linked monodisperse paramagnetic chains", by E. M. Furst, C. Suzuki, M. Fermigier, A. P. Gast, Langmuir, 14, 7334-7336 (1998), "Suspensions of magnetic particles", by M. Fermigier, Y. Grasselli, Bulletin of the SFP (105) July 1996, and "Flexible magnetic filaments as micromechanical sensors", by C. Goubault, P. Jop, M. Fermigier, J. Baudry, E. Bertrand, J. Bibette, Phys. Rev. Lett., 91, 26, 260802-1 to 260802-4 (2003), the contents of which are incorporated herein by reference.

In particular, those articles describe how to proceed in order to obtain chains of magnetic-latex particles that include a polystyrene matrix containing grains of iron oxide with functions on the surface, and that are bonded together in permanent manner following a chemical reaction, in particular covalent bonds between the surfaces of adjacent particles; a method is also described of obtaining chains of ferrofluid-emulsion droplets that are bonded together by physical interactions. The length and the diameter of the permanent chains obtained in this way can be controlled. Such magnetic chains constitute anisotropic magnetic objects that can be oriented and displaced under the effect of a magnetic field.

The dimensions of the magnetic chains may satisfy the same conditions as for the magnetic fibers.

In general, the compounds of the invention advantageously may contain an oily phase and/or an aqueous phase, in particular as defined hereunder.

With regard to the oily phase, said phase may contain oils other than the hereunder-mentioned volatile oils, in particular non-volatile hydrocarbon or silicone oils in association, where necessary, with solid fatty materials such as waxes and/or paste compounds.

In an implementation of the invention, the first composition contains at least one goniochromatic coloring agent in which a color change can be observed as a function of the angle of observation. The goniochromatic coloring agent may optionally be magnetic.

When the first composition contains magnetic particles of a certain color and a non-magnetic goniochromatic coloring agent, said coloring agent may be selected so that its range of colors passes substantially through the color of the magnetic particles.

By way of example, this can make the magnetic particles more difficult to detect so long as they are not oriented under the effect of a magnetic field.

This can also allow the pattern induced by orienting the magnetic particles to appear only when the made-up surface is under certain observation and/or lighting conditions, thereby making it possible to create pattern disposition and appearance effects that are particularly attractive.

Goniochromatic Coloring Agents

The first composition may contain at least one interferential coloring agent, in particular a goniochromatic coloring agent which may present magnetic properties, where appropriate.

The term "goniochromatic coloring agent" as used in the context of the present invention means a coloring agent that makes it possible, when the composition is spread on a surface, to obtain a color path in the a*b* plane of the 1976

CIE color space which corresponds to a variation Dh of the tint angle h of at least 20° when the angle of observation is varied relative to the normal in the range 0° to 80° for light at an angle of incidence of 45°.

By way of example, the color path may be measured by means of a spectrogonioreflectometer, from INSTRUMENT SYSTEMS and referenced GON 360 GONIOMETER, after the first composition has been spread in the fluid state to a thickness of 300 µm by means of an automatic spreader on a contrast card from ERICHSEN and referenced Typ 24/5, the measurements being performed on the black background of the card.

By way of example, the goniochromatic coloring agent may be selected from multilayer interference structures and liquid crystal coloring agents.

By way of example, a multilayer structure may comprise at least two layers, each layer being produced, for example, from at least one material selected from the group constituted by the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers, and combinations thereof.

The multilayer structure may optionally be symmetrical with respect to a central layer as regards the chemical nature of the stacked layers. Depending on the thickness and nature of the various layers, different effects are obtained.

Examples of symmetrical multilayer interference structures are as follows: $Fe_2O_3/SiO_2/Fe_2O_3/SiO_2/Fe_2O_3$, a pigment having this structure being sold under the trade name SICOPEARL by BASF; $MoS_2/SiO_2$/mica-oxide/$SiO_2$/$MoS_2$; $Fe_2O_3/SiO_2$/mica-oxide/$SiO_2/Fe_2O_3$; $TiO_2/SiO_2/$ $TiO_2$ and $TiO_2/Al_2O_3/TiO_2$, pigments with these structures being sold under the trade name XIRONA by MERCK (Darmstadt).

By way of example, liquid crystal coloring agents comprise silicones, or cellulose ethers onto which mesomorphic groups have been grafted. Examples of suitable liquid crystal goniochromatic particles are those sold by CHENIX, and those sold under the trade name HELICONE® HC by WACKER.

Suitable goniochromatic coloring agents are some nacres; pigments having effects on synthetic substrates, in particular alumina, silica, borosilicate, iron oxide, or aluminum type substrates; or holographic interference flakes coming from a polyterephthalate film.

By way of example, the mass ratio of the proportion of magnetic pigments to the proportion of goniochromatic coloring agent may be in the range to ¼, e.g. in the range ½ to 2, e.g. close to 1.

The material may further contain dispersed goniochromatic fibers. Such fibers could present a length that is less than 80 µm, for example.

The first composition may also contain at least one diffractive pigment which may present magnetic properties if necessary.

Diffractive Pigments

The term "diffractive pigment" as used in the context of the present invention means a pigment that is capable of producing a variation in color depending on the angle of observation when lit by white light, because of the presence of a structure which diffracts the light. Such a pigment is also sometimes referred to as a holographic pigment.

A diffractive pigment may include a diffraction grating that is capable of diffracting an incident ray of monochromatic light in defined directions.

The diffraction grating may comprise a periodic pattern, in particular a line, with the distance between two adjacent patterns being the same as the wavelength of the incident light.

When the incident light is polychromatic, the diffraction grating separates the various spectral components of the light and produces a rainbow effect.

With regard to the structure of diffractive pigments, reference can usefully be made to the article "Pigments Exhibiting Diffractive Effects" by Alberto Argoitia and Matt Witzman, 2002, Society of Vacuum coaters, 45$^{th}$ Annual Technical Conference Proceedings 2002, the contents of which are incorporated herein by reference.

The diffractive pigment may be made with patterns having various profiles, in particular triangular, optionally symmetrical, notched, of optionally constant width, or sinusoidal.

The spatial frequency of the grating and the depth of the patterns are selected as a function of the degree of separation of the various desired orders. The frequency may be in the range 500 lines per mm to 3000 lines per mm, for example.

Each of the particles of the diffractive pigment preferably presents a flat shape, and in particular a wafer shape.

A single pigment particle may include two crossed diffraction gratings that are optionally perpendicular, and that optionally have the same ruling.

The diffractive pigment may present a multilayer structure comprising a layer of reflective material that is covered on at least one side by a layer of dielectric material. The dielectric material may make the diffractive pigment stiffer and longer lasting. For example, the dielectric material may thus be selected from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF, and combinations thereof. For example, the reflective material may be selected from metals and alloys thereof, and also from non-metallic reflective materials: Metals that may be used include Al, Ag, Cu, Au, Pt, Sn, Ti, Pd, Ni, Co, Rd, Nb, Cr, and materials, combinations, or alloys thereof. Such a reflective material may, on its own, constitute the diffractive pigment which then comprises a single layer.

In a variant, the diffractive pigment may include a multilayer structure comprising a core of dielectric material with a reflective layer covering at least one side, or indeed completely encapsulating, the core. A layer of dielectric material may also cover the reflective layer(s). The dielectric material used is thus preferably inorganic, and may, for example, be selected from metal fluorides, metal oxides, metal sulfides, metal nitrides, metal carbides, and combinations thereof. The dielectric material may be in the crystalline, semi-crystalline, or amorphous state. In this configuration, the dielectric material may, for example, be selected from the following materials: $MgF_2$, SiO, $SiO_2$, $Al_2O_3$, $TiO_2$, WO, AlN, BN, $B_4C$, WC, TiC, TiN, $N_4Si_3$, ZnS, glass particles, diamond-type carbons, and combinations thereof.

In a variant, the diffractive pigment may be composed of a preformed dielectric or ceramic material such as a naturally lamellar mineral, e.g. mica peroskovite or talc; or synthetic platelets formed from glass, alumina, $SiO_2$, carbon, an iron oxide/mica, mica covered in BN, BC, graphite, or bismuth oxychloride, and combinations thereof.

Instead of a layer of dielectric material, other materials that improve the mechanical properties may be suitable. Such materials may include silicone, metal silicides, semiconductor materials formed from elements of groups III, IV, and V, metals having a body centered cubic crystal structure, metal-ceramic compositions or materials, semiconductor glasses, and various combinations thereof.

In particular, the diffractive pigment used may be selected from those described in US patent application No. 2003/0031870 published on Feb. 13, 2003.

A diffractive pigment may, for example, have the following structure: $MgF_2/Al/MgF_2$, a diffractive pigment having this structure being sold by FLEX PRODUCTS under the trade names SPECTRAFLAIR 1400 Pigment Silver or SPECTRAFLAIR 1400 Pigment Silver FG. The proportion by weight of $MgF_2$ may be in the range 80% to 95% of the total weight of the pigment.

Other diffractive pigments are sold under the trade names Metalure® Prismatic by ECKART®.

Other possible structures are Fe/Al/Fe or Al/Fe/Al, which present non-zero magnetic susceptibility.

By way of example, the quantity of diffractive pigment may be in the range 0.1% to 5% by weight relative to the total weight of the first composition.

By way of example, the size of the diffractive pigment may be in the range 5 µm to 200 µm, and preferably in the range 5 µm to 100 µm, e.g. in the range 5 µm to 30 µm.

The thickness of the diffractive-pigment particles may be less than or equal to 3 µm, or preferably 2 µm, e.g. about 1 µm.

Reflective Particles

By way of example, the first composition may contain reflective particles, in particular optionally-magnetic flakes, in particular having metallic luster, amongst others.

The term "reflective particles" as used in the context of the present invention means particles the size and structure of which, in particular the thickness of the layer or layers constituting them and their physical and chemical natures, and their surface state, allow them to reflect incident light. If appropriate, said reflection may have sufficient intensity to create highlight points on the surface of the composition or of the mixture, when the composition or the mixture is applied to the surface to be made up, which highlight points are visible to the naked eye, i.e. they are points of greater brightness that contrast with their environment and appear to shine.

The reflective particles may be selected in a manner such that they do not significantly alter the coloring effect generated by the coloring agents associated therewith, and more particularly to optimize that effect in terms of color yield. More particularly, they may have a yellow, pink, red, bronze, orangey, brown, and/or copper glint.

The reflective particles may optionally reflect the visible spectrum in substantially uniform manner, for example as occurs with particles coated with a metal such as silver or aluminum, which may, for example, thus lead to a metallic luster having a tone that is non-neutral, yellow, pink, red, bronze, orangey, brown, and/or coppery, depending on the nature of the metallic surface compound, for example.

The reflective particles may be present in the first composition in an amount in the range 0.5% to 60% by weight relative to the total weight of the first composition, specifically 1% to 30% by weight, and in particular 3% to 10% by weight.

Said particles may be in various forms, in particular they may be in the form of flakes, or they may be globular, in particular spherical, possibly elongate, with a high form factor, where appropriate, and they may optionally present magnetic susceptibility, linked to the presence of a magnetic material.

When the reflective particles are magnetic, they preferably present a flat shape such that a change in their orientation within the composition leads to a change in appearance.

Regardless of their form, the reflective particles may optionally have a multilayer structure; with a multilayer structure, for example, they may have at least one layer of uniform thickness, in particular of a reflective material, advantageously a metallic compound.

When the reflective particles do not have a multilayer structure, they may, for example, be composed of at least one metallic compound, e.g. metal oxides, in particular oxides of titanium or iron obtained by synthesis.

When the reflective particles have a multilayer structure they may, for example, comprise a natural or synthetic substrate, in particular a synthetic substrate which is at least partially coated with at least one layer of a reflective material, in particular at least one layer of at least one metallic compound such as a metal or an alloy. The layer of the metallic compound is advantageously an outer layer of the structure.

The substrate may be a single material or multiple materials, and it may be organic and/or inorganic.

More particularly, the substrate may be selected from glasses, ceramics, graphite, metal oxides, aluminas, silicas, silicates, in particular aluminosilicates and borosilicates, synthetic mica, and mixtures thereof, this list not being limiting.

The reflective material may comprise a layer of metal or of a metallic material.

Reflective particles have been described in particular in Japanese patent documents JP-A-09188830, JP-A-10158450, JP-A-10158541, JP-A-07258460 and JP-A-05017710.

Further examples of reflective particles comprising a mineral substrate coated with a metal layer that may be mentioned are particles comprising a substrate of borosilicate coated with silver, also termed "white nacres".

Glass substrate particles coated with silver in the form of flakes are sold under the trade name MICROGLASS METASHINE REFSX 2025 PS by TOYAL. Glass substrate particles coated with nickel/chromium/molybdenum alloy are sold under the trade name CRYSTAL STAR GF 550, GF 2525 by the same company.

Reflective particles of any form may also be selected from particles of synthetic substrate at least partially coated with at least one layer of at least one metallic material, in particular a metal oxide selected, for example, from oxides of titanium, in particular $TiO_2$, of iron, in particular $Fe_2O_3$, of tin, or of chromium, barium sulfate, and the following materials: $MgF_2$, $CrF_3$, $ZnS$, $ZnSe$, $SiO_2$, $Al_2O_3$, $MgO$, $Y_2O_3$, $SeO_3$, $SiO$, $HfO_2$, $ZrO_2$, $CeO_2$, $Nb_2O_5$, $Ta_2O_5$, $MoS_2$, and their mixtures or alloys.

Examples of such particles that may be mentioned are particles comprising a substrate of synthetic mica coated with titanium dioxide, or glass particles coated either with brown iron oxide, titanium oxide, tin oxide, or one of their mixtures such as those sold under the trade name REFLECKS® by ENGELHARD.

As other examples of reflective particles presenting, at their surface, a metallic compound or including at least one coated metallic compound, mention may be made of particles proposed under the trade names METASHINE® ME 2040 PS, METASHINE® MC5090 PS or METASHINE® MC280GP (2523) by NIPPON SHEET GLASS, SPHERICAL SILVER POWDER® DC 100, SILVER FLAKE® JV 6 or GOLD POWDER® A1570 by ENGELHARD, STARLIGHT REFLECTIONS FXM® by ENERGY STRATEGY ASSOCIATES INC, BRIGHT SILVER® 1 E 0.008X0.008 by MEADOWBROOK INVENTIONS, ULTRAMIN® (ALUMINIUM POUDRE FINE LIVING), and COS- METIC METALLIC POWDER VISIONNAIRE BRIGHT SILVER SEA®, COSMETIC METALLIC. POWDER VISIONAIRE NATURAL GOLD® (60314) or COSMETIC METALLIC POWDER VISIONAIRE HONEY® (60316) by ECKART.

The first composition of the invention may contain at least one optionally-magnetic nacre.

Nacres

The term "nacre" means colored particles of any form, which may optionally be iridescent, as produced in the shells of certain mollusks, or which are synthesized, and which exhibit a "pearlescent" coloring effect by optical interference.

Nacres may be selected from nacre pigments such as mica titanium coated with iron oxide, mica coated with bismuth oxychloride, mica titanium coated with chromium oxide, mica titanium coated with an organic colorant, in particular of the type mentioned above, and nacre pigments based on bismuth oxychloride. They may also be particles of mica on the surface of which at least two successive layers of metal oxides and/or organic coloring substances have been superimposed.

More particularly, the nacres may have a yellow, pink, red, bronze, orangey, brown, gold, and/or coppery color or glint.

Illustrative examples of nacres suitable for being introduced into the first composition and that may be mentioned are gold color nacres, in particular those sold by ENGELHARD under the trade names Brillant gold 212G (Timica), Gold 222C (Cloisonne), Sparkle gold (Timica), Gold 4504 (Chromalite), and Monarch gold 233X (Cloisonne); bronze nacres, in particular those sold by MERCK under the trade names Bronze fine (17384) (Colorona) and Bronze (17353) (Colorona), and by ENGELHARD under the trade name Super bronze (Cloisonne); orange nacres especially those sold by ENGELHARD under the trade names Orange 363C (Cloisonne) and Orange MCR 101 (Cosmica), and by MERCK under the trade names Passion orange (Colorona) and Matte orange (17449) (Microna); brown-tinted nacres sold by ENGELHARD under the trade names Nu-antique copper 340XB (Cloisonne) and Brown CL4509 (Chromalite); nacres with a copper glint sold by ENGELHARD under the trade name Copper 340A (Timica); nacres with a red glint, especially those sold by MERCK under the trade name Sienna fine (17386) (Colorona); nacres with a yellow glint, especially those sold by ENGELHARD under the trade name Yellow (4502) (Chromalite); red-tinted nacres with gold glints, especially those sold by ENGELHARD under the trade name Sunstone G012 (Gemtone); pink nacres, especially those sold by ENGELHARD under the trade name Tan opale G005 (Gemtone); black nacres with a glint, especially those sold by ENGELHARD under the trade name Nu antique bronze 240 AB (Timica); blue nacres, especially those sold by MERCK under the trade name Matte blue (17433) (Microna); white nacres with silvery glints, especially those sold by MERCK under the trade name Xirona Silver; and orange-pink green-gold highlight nacres sold by MERCK under the trade names Indian summer (Xirona) and mixtures thereof.

By way of example, the first composition may contain at least one optionally-magnetic filler.

Fillers

The term "filler" means particles of any form which are insoluble in the composition medium regardless of the temperature at which the composition is manufactured. A filler primarily acts to modify the rheology or texture of the composition. The nature and quantity of the particles could depend on the desired mechanical properties and textures.

Examples of fillers that may be mentioned include amongst others talc, mica, silica, kaolin, and sericite, and powders of polyamide, polyolefin, e.g. polyethylene, polytetrafluoroethylene, polymethylmethacrylate, or polyurethane, powdered starch, and silicone resin beads.

Amongst other things, the fillers may be intended to create a fuzzy effect, in particular for a foundation, so as to conceal skin imperfections.

The first composition may also contain colorants, organic pigments, or lakes.

Absorbent Coloring Agent: Colorants, Organic Pigments, and Lakes

The composition comprising the magnetic bodies may contain at least one coloring agent other than a coloring agent that is sensitive to an external stimulus and producing a color by absorbing at least a fraction of the visible spectrum.

This coloring agent, producing a color by an absorption phenomenon, may be constituted by a pigment that is an optionally magnetic, organic, or inorganic, or it may be a hybrid comprising both organic material and inorganic material.

The absorbent coloring agent may optionally be a particulate compound.

Where appropriate, the particles of a single magnetic pigment constitute both the coloring agent, producing the color by an absorption phenomenon, and the magnetic bodies.

These absorbent coloring agents may be a colorant, a lake or an organic pigment, for example.

The colorants may be liposoluble or hydrosoluble.

Examples of liposoluble colorants are Sudan red, D&C Red No. 17, D&C Green No. 6, β-carotene, soybean oil, Sudan brown, D&C Yellow No. 11, D&C Violet No. 2, D&C orange No. 5, and quinoline yellow.

Examples of hydrosoluble colorants are beetroot juice and methylene blue.

By way of example, the colorants may represent 0.1% to 20% by weight of the first or second composition, or even 0.1% to 6%, when present.

The lakes or organic pigments may be selected from the following materials and mixtures thereof:
cochineal carmine;
the organic pigments of azo, anthraquinone, indigo, xanthene, pyrene, quinoline, triphenylmethane, or fluorane dyes;
organic lakes or insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Organic pigments that may be mentioned include those with the following denominations: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The organic coloring agents may comprise an organic lake supported by an organic support such as colophane or aluminum benzoate, for example.

Particular organic lakes that may be mentioned include those with the following denominations: D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, FD&C Yellow No. 6 Aluminum lake.

The chemical materials corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are incorporated herein by reference.

The coloring agent may advantageously be a composite pigment including a core that is coated at least in part by a membrane.

Composite Pigments

The composite pigment may be composed of particles comprising:
an optionally-magnetic inorganic core; and
at least one at least partial coating of at least one organic coloring substance.

At least one binder may advantageously contribute to fixing the organic coloring substance onto the inorganic core.

The particles of composite pigment may have a variety of forms. In particular, said particles may be in the form of flakes or they may be globular, in particular spherical, and may be hollow or solid. The term "in the form of flakes" means particles for which the ratio of the largest dimension to the thickness is 5 or more.

A composite pigment may, for example, have a specific surface area in the range 1 square meter per gram ($m^2/g$) to 1000 $m^2/g$, in particular in the range about 10 $m^2/g$ to about 600 $m^2/g$, and in particular in the range about 20 $m^2/g$ to about 400 $m^2/g$. The specific surface area is the value measured using the BET (Brunauer-Emmett-Teller) method.

The proportion by weight of the core may exceed 50% relative to the total weight of the composite pigment, for example lying in the range 50% to 70%, e.g. in the range 60% to 70%.

The composite pigment may be different from an interferential pigment as described in U.S. Pat. No. 6,428,773, for example. By way of example, an interferential pigment includes a plurality of layers of constant thickness of materials selected so as to be able to produce optical interferences.

The saturation C* of the composite pigment may be greater than or equal to 30, measured in accordance with the following protocol.

Protocol for Measuring the Saturation of the Composite Pigment

The values a* and b* in the CIE L*a*b* space of the composite pigment are measured as follows:

Pure composite pigment is compacted in a rectangular dish having dimensions of 2 centimeters (cm)×1.5 cm and a depth of 3 mm, by applying pressure of 100 bars.

The values a* and b* of the compacted pigment are measured with a MINOLTA 3700d spectrophotometer, in excluded specular mode, under D65 lighting, medium aperture. Saturation is given by $C^*=(a^{*2}+b^{*2})^{1/2}$.

Inorganic Core

The inorganic core of the composite pigment may have any form that is suitable for fixing particles of organic coloring substance, for example spherical, globular, granular, polyhedral, acicular, spindle-shaped, flattened in the form of a flake, a rice grain, or a scale, and a combination of these forms, this list not being limiting.

The ratio of the largest dimension of the core to its smallest dimension may be in the range 1 to 50.

The inorganic core may have a mean size in the range about 1 nm to about 100 nm, or even in the range about 5 nm to about 75 nm, for example in the range about 10 nm to about 50 nm, in particular 20 nm or 25 nm.

The term "mean size" means the size given by the statistical grain size distribution at half the population, referred to as "D50". The mean size may be a number mean size determined by image analysis (electron microscopy).

The inorganic core may present a refractive index that is greater than or equal to 2, or even greater than or equal to 2.1, e.g. greater than or equal to 2.2.

The inorganic core may be formed from an optionally magnetic material selected from a non-limiting list comprising metallic salts and metal oxides, in particular oxides of titanium, zirconium, cerium, zinc, iron, iron blue, aluminum, and chromium, aluminas, glasses, ceramics, graphite, silicas, silicates, in particular aluminosilicates and borosilicates, synthetic mica, and mixtures thereof.

Oxides of titanium, in particular $TiO_2$, of iron, especially $Fe_2O_3$, of cerium, zinc, and aluminum, silicates, in particular aluminosilicates and borosilicates, are particularly suitable.

The inorganic core may have a specific surface area, measured using the BET method, in the range about 1 $m^2/g$ to about 1000 $m^2/g$, preferably in the range about 10 $m^2/g$ to about 600 $m^2/g$, for example in the range about 20 $m^2/g$ to about 400 $m^2/g$.

The inorganic core may be colored if appropriate.

The organic coloring substance may be as defined above for the absorbent coloring agent.

By way of example, the organic coloring material may comprise at least one organic pigment, e.g. at least one organic lake.

By way of example, the organic coloring material may be selected from the insoluble particulate compounds in the physiologically acceptable medium of the composition.

By way of example, the organic coloring material may comprise pigments, e.g. organic lakes or other organic coloring materials, that may be selected from the following compounds and mixtures thereof:

cochineal carmine;

the organic pigments of azo, anthraquinone, indigo, xanthene, pyrene, quinoline, triphenylmethane, or fluorane dyes;

organic lakes or insoluble salts of sodium, potassium, calcium, barium, aluminum, zirconium, strontium, titanium, or of acid dyes such as azo, anthraquinone, indigo, xanthene, pyrene, quinoline, triphenylmethane, or fluorine dyes, which dyes may comprise at least one carboxylic or sulfonic acid group.

Organic pigments that may be mentioned include those with the following denominations: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The organic coloring substance may comprise an organic lake supported by an organic support such as colophane or aluminum benzoate, for example.

Particular organic lakes that may be mentioned include those with the following denominations: D&C Red No. 2 Aluminum lake, D&C Red No. 3 Aluminum lake, D&C Red No. 4 Aluminum lake, D&C Red No. 6 Aluminum lake, D&C Red No. 6 Barium lake, D&C Red No. 6 Barium/Strontium lake, D&C Red No. 6 Strontium lake, D&C Red No. 6 Potassium lake, D&C Red No. 7 Aluminum lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminum lake, D&C Red No. 9 Barium lake, D&C Red No. 9 Barium/Strontium lake, D&C Red No. 9 Zirconium lake, D&C Red No. 10 Sodium lake, D&C Red No. 19 Aluminum lake, D&C Red No. 19 Barium lake, D&C Red No. 19 Zirconium lake, D&C Red No. 21 Aluminum lake, D&C Red No. 21 Zirconium lake, D&C Red No. 22 Aluminum lake, D&C Red No. 27 Aluminum lake, D&C Red No. 27 Aluminum/Titanium/Zirconium lake, D&C Red No. 27 Barium lake, D&C Red No. 27 Calcium lake, D&C Red No. 27 Zirconium lake, D&C Red No. 28 Aluminum lake, D&C Red No. 30 lake, D&C Red No. 31 Calcium lake, D&C Red No. 33 Aluminum lake, D&C Red No. 34 Calcium lake, D&C Red No. 36 lake, D&C Red No. 40 Aluminum lake, D&C Blue No. 1 Aluminum lake, D&C Green No. 3 Aluminum lake, D&C Orange No. 4 Aluminum lake, D&C Orange No. 5 Aluminum lake, D&C Orange No. 5 Zirconium lake, D&C Orange No. 10 Aluminum lake, D&C Orange No. 17 Barium lake, D&C Yellow No. 5 Aluminum lake, D&C Yellow No. 5 Zirconium lake, D&C Yellow No. 6 Aluminum lake, D&C Yellow No. 7 Zirconium lake, D&C Yellow No. 10 Aluminum lake, FD&C Blue No. 1 Aluminum lake, FD&C Red No. 4 Aluminum lake, FD&C Red No. 40 Aluminum lake, FD&C Yellow No. 5 Aluminum lake, FD&C Yellow No. 6 Aluminum lake.

The chemical compounds corresponding to each of the organic coloring substances listed above are mentioned in the work entitled "International Cosmetic Ingredient Dictionary and Handbook", 1997 edition, pages 371 to 386 and 524 to 528, published by "The Cosmetic, Toiletry, and Fragrance Association", the contents of which are incorporated herein by reference.

The proportion by weight of organic coloring material may lie in the range about 10 parts to about 500 parts by weight per 100 parts of inorganic core, or even in the range about 20 parts to about 250 parts by weight, e.g. in the range about 40 parts to about 125 parts by weight per 100 parts of inorganic core.

The total content of organic coloring material of the composition, coming from the composite pigment and from other possible pigments, may be less than 10%, for example, relative to the total weight of the composition.

The proportion of organic coloring material may exceed 30% relative to the total weight of the composite pigment, for example lying in the range 30% to 50%, e.g. in the range 30% to 40%.

Binder

The composite-pigment binder may be of any type provided that it allows the organic coloring substance to adhere to the surface of the inorganic core.

In particular, the binder may be selected from the following non-limiting list: silicone materials, polymeric, oligomeric or similar materials, in particular from organosilanes, fluoroalkylated organosilanes and polysiloxanes, for example polymethylhydrogen siloxane, as well as a variety of coupling agents such as coupling agents based on silanes, titanates, aluminates, zirconates, and mixtures thereof.

The silicone compound may be selected from the following non limiting list:

organosilanes (1) obtained from alkoxysilanes;

polysiloxanes (2) which may optionally be modified, selected from the following non limiting list:

modified polysiloxanes (2A) comprising at least one radical selected in particular from polyethers, polyesters and epoxy compounds (henceforth termed "modified polysiloxanes");

polysiloxanes (2B) carrying, on one silicon atom located at the end of the polymer, at least one group selected from the following non-limiting list: carboxylic acids, alcohols, and hydroxyl groups; and fluoroalkylated organosilane compounds (3) obtained from fluoroalkylsilanes.

The organosilane compounds (1) may be obtained from alkoxysilane compounds represented by formula (I):

$$R^1{}_aSiX_{4-a} \qquad (I)$$

in which:

$R^1$ represents $C_5H_5$—, $(CH_3)_2CH$—$CH_2$— or a $C_bH_{2b+1}$— type radical (in which b lies in the range 1 to 18);

X represents $CH_3O$— or $C_2H_5O$—; and a lies in the range 0 to 3.

Specific examples of alkoxysilane compounds may include alkoxysilanes selected from: methyltriethoxysilane, dimethyldiethoxysilane, phenyltriethoxysilane, diphenyldiethoxysilane, methyltrimethoxysilane, dimethyldimethoxysilane, phenyltrimethoxysilane, diphenyldimethoxysilane, isobutyltrimethoxysilane, decyltrimethoxysilane, and the like, in particular from methyltriethoxysilane, phenyltriethoxysilane, methyltrimethoxysilane, dimethyldimethoxysilane, isobutyltrimethoxysilane, more preferably from methyltriethoxysilane, methyltrimethoxysilane, and phenyltriethoxysilane.

The polysiloxanes (2) may in particular have formula (II):

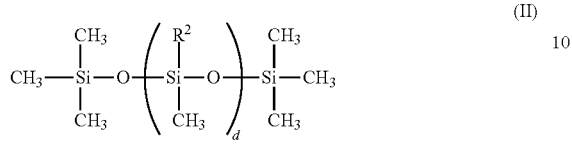

in which $R^2$ represents H— or $CH_3$— and d lies in the range 15 to 450.

Polysiloxanes for which $R^2$ represents H are preferred.

The modified polysiloxanes (2A) may in particular have the following formula (III):

($a^1$) modified polysiloxanes carrying polyethers, represented by formula (III):

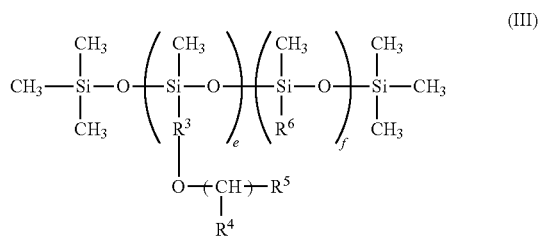

in which $R^3$ represents —$(CH_2)_h$—; $R^4$ represents —$(CH_2)_i$—$CH_3$; $R^5$ represents —OH, —COOH, —CH=$CH_2$, —C($CH_3$)=$CH_2$ or —$(CH_2)_j$—$CH_3$; $R^6$ represents —$(CH_2)_k$—$CH_3$; g and h lie independently in the range 1 to 15; j and k lie independently in the range 0 to 15; e lies in the range 1 to 50, and f lies in the range 1 to 300;

($a^2$) modified polysiloxanes carrying polyesters, represented by formula (IV):

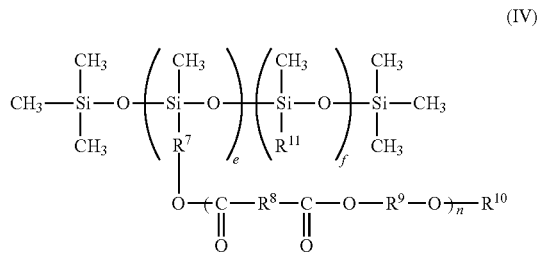

in which $R^7$, $R^8$, and $R^9$ independently represent —$(CH_2)_q$—; $R^{10}$ represents —OH, —COOH, —CH=$CH_2$, —C($CH_3$)=$CH_2$ or —$(CH_2)_r$—$CH_3$; $R^{11}$ represents —$(CH_2)_s$—$CH_3$; n and q lie independently in the range 1 to 15, r and s lie independently in the range 0 to 15; e lies in the range 1 to 50, and f lies in the range 1 to 300, ($a^3$) modified polysiloxanes carrying epoxy radicals represented by formula (V):

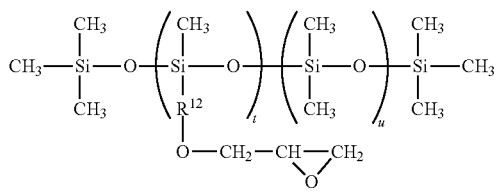

in which $R^{12}$ represents —$(CH_2)_v$—; v lies in the range 1 to 15; t lies in the range 1 to 50, and u lies in the range 1 to 300; or mixtures thereof.

Preferred modified polysiloxanes (2A) are modified polysiloxanes carrying polyethers with formula (III).

Polysiloxanes modified at the terminal portion (2B) may have formula (VI):

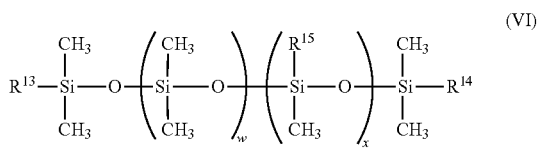

in which $R^{13}$ and $R^{14}$ may represent —OH, $R^{16}$—OH, or $R^{17}$—COOH, independently of each other; $R^{15}$ represents —$CH_3$ or —$C_6H_5$; $R^{16}$ and $R^{17}$ represent —$(CH_2)_y$—; lies in the range 1 to 15; w lies in the range 1 to 200; and x lies in the range 0 to 100.

Preferred polysiloxanes modified on at least one end include those carrying at least a radical ($R^{16}$ and/or $R^{17}$) carrying a carboxylic acid group on at least one terminal silicon atom.

Fluoroalkylated organosilane compounds (3) may be obtained from fluoroalkylsilanes represented by formula (VII):

$$CF_3(CF_2)_zCH_2CH_2(R^{18})_aSiX_{4-a} \qquad (VII)$$

in which:
$R^{18}$ represents $CH_3$—, $C_2H_5$—, $CH_3O$— or $C_2H_5O$—;
X represents $CH_3O$— or $C_2H_5O$—;
z lies in the range 0 to 15 and a lies in the range 0 to 3.

In particular, the fluoroalkylsilanes may be selected from the following non limiting list: trifluoropropyltrimethoxysilane, tridecafluorooctyltrimethoxysilane, heptadecafluorodecyltrimethoxysilane, heptadecafluorodecylmethyldimethoxysilane, trifluoropropyltriethoxysilane, tridecafluorooctyltriethoxysilane, heptadecafluorodecyltriethoxysilane, heptadecafluorodecylmethyldiethoxysilane and the like, in particular trifluoropropyltrimethoxysilane, tridecafluorooctyltrimethoxysilane and heptadecafluorodecyltrimethoxysilane, and more preferably trifluoropropyl trimethoxysilane and tridecafluorooctyltrimethoxysilane.

The silane-based coupling agents may be selected from the following non limiting list: vinyltrimethoxysilane, vinyltriethoxysilane, γ-aminopropyl-triethoxysilane, γ-glycidoxypropyltrimethoxysilane, γ-mercaptopropyltrimethoxysilane, γ-methacryloxypropyltrimethoxysilane, N-β(aminoethyl)-γ-aminopropyltrimethoxysilane, γ-glycidoxypropylmethyldimethoxysilane, γ-chloropropyltrimethoxysilane, and the like.

The titanate-based coupling agents may be selected from the following list: isopropylstearoyl titanate, isopropyltris(dioctylpyrophosphate) titanate, isopropyltri(N-aminoethylaminoethyl) titanate, tetraoctylbis(ditridecylphosphate) titanate, tetra(2,2-diaryloxymethyl-1-butyl)bis(ditridecyl) phosphate titanate, bis(dioctylpyrophosphate)oxyacetate titanate, bis(dioctylpyrophosphate)ethylene titanate, and the like.

The aluminate-based coupling agents may be selected from acetoalkoxyaluminum diisopropylate, aluminum diisopropoxymonoethylacetoacetate, aluminum triethylacetoacetate, aluminum triacetylacetonate, and the like.

The zirconate-based coupling agents may be selected from the following list: zirconium tetrakisacetylacetonate, zirconium dibutoxybisacetylacetonate, zirconium tetrakisethylacetoacetate, zirconium tributoxymonoethylacetoacetate, zirconium tributoxyacetylacetonate, and the like.

The compounds acting as a binder may have a molar mass in the range 300 to 100 000.

To obtain a layer which uniformly coats the inorganic cores, the binder is preferably in the liquid state or is soluble in water or other solvents.

The quantity of binder may lie in the range 0.01% to 15%, in particular from 0.02% to 12.5%, and more particularly from 0.03% to 10% by weight (calculated with respect to C or Si) relative to the weight of particles comprising the core and the binder. Further details regarding the calculation of the relative quantity of binder can be found in patent application EP 1 184 426 A2. The relative proportion of binder may be less than or equal to 5%, e.g. less than or equal to 3%, relative to the total weight of the composite pigment.

Preparation of Composite Pigment

The composite pigment may be prepared using any appropriate method, e.g. a mechanical/chemical method or a method of precipitation in solution, with the organic coloring material being dissolved, then precipitated onto the surface of the core.

A binder may optionally be used.

A method comprising mechanically mixing an organic pigment and the inorganic core is preferred.

A binder may be added or mixed to the inorganic core before the organic coloring material is introduced.

The composite pigment may, for example, be produced using one of the processes described in European patent applications EP 1 184 426 and EP 1 217 046, the contents of which are hereby incorporated by reference, and advantageously by the process described in EP 1 184 426.

In one implementation, the particles intended to constitute the inorganic core are first mixed with the binder.

So that the binder can adhere uniformly to the surface of the inorganic core, it is preferable to pass said particles initially through a mill to disaggregate them.

The mixing and agitation conditions are selected so that the core is uniformly coated with binder. Such conditions may be controlled so that the linear load is in the range 19.6 N/cm (newtons/centimeter) to 19160 N/cm, in particular in the range 98 N/cm to 14170 N/cm and preferably in the range 147 N/cm to 980 N/cm; the treatment time is in the range 5 minutes to 24 hours, preferably in the range 10 minutes to 20 hours; the rotation rate may be in the range 2 rpm (revolutions per minute) to 1000 rpm, in particular in the range 5 rpm to 1000 rpm, and more preferably in the range 10 rpm to 800 rpm.

After coating the inorganic core with binder, the organic coloring substance is added and mixed with agitation so that it adheres to the layer of binder.

Examples of addition methods are continuous addition in large quantities, or in small quantities.

Mixing and agitation, whether of the inorganic cores with the binder or of the organic coloring substance with the inorganic cores coated with binder, may be carried out using an apparatus which can apply a sharp shearing and/or compressive force to the mixture of powders. Examples of apparatus of that type are roller mixers, blade mixers, and the like. Roller mixers are particularly suitable. A list of suitable apparatus is given in EP 1 184 426 A2.

A further method for manufacturing a composite pigment has been described in Japanese patent JP 3286463, which discloses a solution precipitation process.

The organic coloring substance is dissolved in ethanol and the inorganic cores are then dispersed in said ethanolic solution.

An aqueous alkaline solution of sodium or potassium carbonate is then slowly added to these mixtures and finally, an ethanolic calcium chloride solution is slowly added, with constant agitation.

The coloring agent may contain a photochrome coloring substance or a photochrome agent.

Coloring Agents that are Sensitive to an External Stimulus

The composition containing the magnetic bodies may include at least one photochromic agent.

Photochromic Agents

In general, a photochromic coloring agent is a coloring agent having the property of changing tint when it is lit by ultraviolet light, and of returning to its initial color when it is no longer lit by said light, or even of passing from a non-colored state to a colored state and vice-versa. In other words, such an agent presents different tints depending on whether it is lit by artificial light, or by light containing a certain amount of UV radiation such as sunlight.

The photochromic agent may have a difference ΔE of at least 5. ΔE is the observed difference in hue in the photochromic substance, i.e. in the presence of UV radiation and in the absence of UV radiation.

Reference may usefully be made to the examples of photochromic agents described in EP 1 410 786, or to the examples of photochromic agents described in US 2004/0228818, the contents of which are hereby incorporated by reference, especially those with a ΔE of more than 5, as measured in the test presented in that document.

Examples of photochromic agents that may be mentioned are naphtopyrane derivatives of the 2H-naphto-[2,1-b]-pyrane type with formula (I) or of the 3H-naphto-[2,1-b]-pyrane type with formula (II):

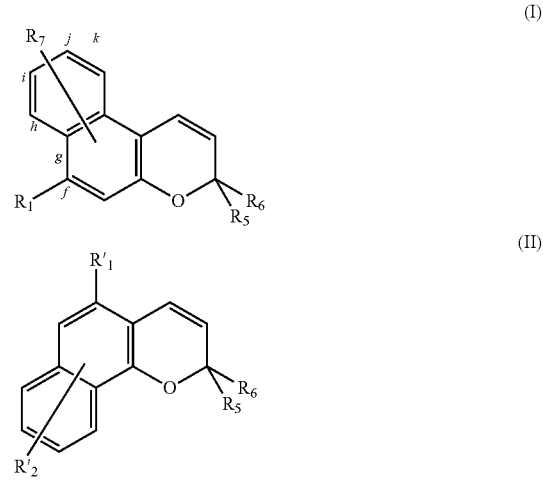

in which:

$R_1$ represents:

(i) a hydrogen atom;
(ii) a linear, branched or cyclic, saturated or unsaturated hydrocarbon group containing 1 to 30 carbon atoms, optionally comprising 1 to 5 heteroatoms selected from N, O, S, Si and P and/or optionally halogenated or perhalogenated;
(iii) a hydrocarbon cycle formed with one of the "f" or "gh" bonds and the radical $R_7$; or
(iv) a group selected from —COOR$_4$, —C(O)NR$_2$R$_3$, —NR$_2$R$_3$, —OR$_4$ and —SR$_4$, in which:

$R_2$ and $R_3$ either independently of each other represent a linear, branched or cyclic, saturated or unsaturated hydrocarbon group containing 1 to 20 carbon atoms, optionally comprising 1 to 5 heteroatoms selected from N, O, S, Si and P; or taken together with the nitrogen atom to which they are bonded, they form a saturated or unsaturated hydrocarbon heterocycle comprising 3 to 10 carbon atoms and optionally 1 to 5 other heteroatoms selected from N, O, S, Si and 2, said cycle optionally being substituted with at least one linear, branched or cyclic, saturated or unsaturated hydrocarbon radical containing 1 to 20 carbon atoms optionally comprising 1 to 5 heteroatoms selected from N, O, S, Si and P;

$R_4$ represents a linear, branched or cyclic, saturated or unsaturated hydrocarbon group containing 1 to 20 carbon atoms, optionally halogenated or perhalogenated, and/or optionally comprising 1 to 5 heteroatoms selected from N, O, S, Si and P;

$R_5$ and $R_6$ independently represent a group selected from:
(i) saturated cyclic aminoaryl groups with formula (IIA) or (IIB):

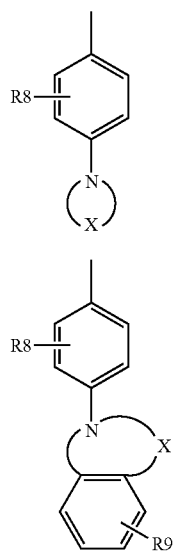

(IIA)

(IIB)

in which the cycle comprising N and X is a saturated cycle containing a total of 3 to 30 atoms including nitrogen, the remainder being carbon atoms and/or heteroatoms selected from O, S, Si, P and/or groups selected from —NH and —NR where R represents a linear, branched or cyclic, saturated or unsaturated hydrocarbon radical containing 1 to 20 carbon atoms optionally comprising 1 to 5 heteroatoms selected from N, O, S, Si and P;

(ii) indolinoaryl groups with formula (III):

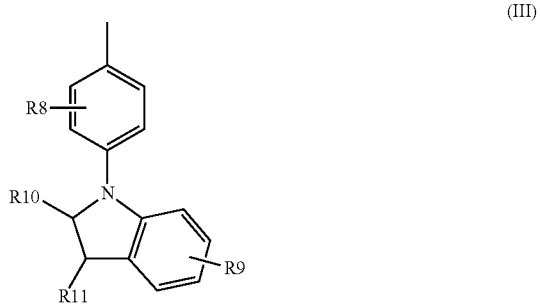

(III)

in which $R_{10}$ and $R_{11}$ independently represent a group selected from (i) linear, branched or cyclic, saturated or unsaturated hydrocarbons groups containing 1 to 30 carbon atoms optionally comprising 1 to 5 heteroatoms selected from N, O, S, Si and P and/or optionally halogenated or perhalogenated; (ii) halogen atoms; (iii) —CN (nitrile), —COOH (carboxylate), —NO$_2$ (nitro) groups; (iv) a hydrogen atom; (v) a group selected from —C(O)NR$_2$R$_3$, —NR$_2$R$_3$, —OR$_4$ or —SR$_4$ where $R_2$, $R_3$ and $R_4$ have the meanings given above; (vi) radicals $R_{10}$ and $R_{11}$ may together form a saturated or unsaturated hydrocarbon cycle containing a total of 5 to 8 atoms (including the atoms of the indoline cycle), said atoms being selected from C, O, S and/or NR where R represents H or a linear, branched or cyclic, saturated or unsaturated hydrocarbon radical containing 1 to 20 carbon atoms optionally comprising 1 to 5 heteroatoms selected from N, O, S, Si and P;

(iii) groups with formula (IV):

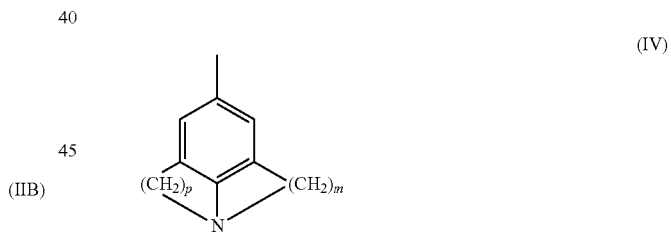

(IV)

in which m and p are independently whole numbers from 2 to 5;

(iv) unsaturated cyclic aminoaryl groups with formulae (VA), (VB) or (VC):

(VA)

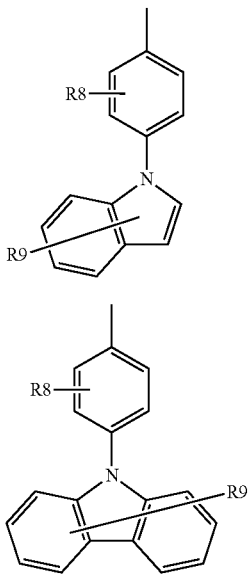

in which $R_8$ and $R_9$ independently represent a group selected from (i) linear, branched or cyclic, saturated or unsaturated hydrocarbon groups containing 1 to 30 carbon atoms optionally comprising 1 to 5 heteroatoms selected from N, O, S, Si and P and/or optionally halogenated or perhalogenated; (ii) halogen atoms; (iii) —CN (nitrile), —COOH (carboxylate), —NO$_2$ (nitro) groups; (iv) a hydrogen atom; (v) a group selected from —C(O)NR$_2$R$_3$, —NR$_2$R$_3$, —OR$_4$ or —SR$_4$ where $R_2$, $R_3$ and $R_4$ have the meanings given above;

(v) a linear, branched or cyclic, saturated or unsaturated hydrocarbon group containing 1 to 30 carbon atoms optionally comprising 1 to 5 heteroatoms selected from N, O, S, Si and P; and especially a group selected from —C$_6$H$_4$—CONR$_2$R$_3$, —C$_6$H$_4$—NR$_2$R$_3$ and —C$_6$H$_4$—OR$_4$ where $R_2$, $R_3$ and $R_4$ have the meanings given above;

$R_7$ represents a group selected from:
(i) linear, branched or cyclic, saturated or unsaturated hydrocarbon groups containing 1 to 30 carbon atoms optionally comprising 1 to 5 heteroatoms selected from N, O, S, Si and P and/or optionally halogenated or perhalogenated;
(ii) halogen atoms;
(iii) —CN (nitrile), —COOH (carboxylate), —NO$_2$ (nitro); —N═N— (azo); ═NH (imino); —CONH$_2$ (amide) groups;
(iv) a hydrogen atom;
(v) a group selected from —C(O)NR$_2$R$_3$, —NR$_2$R$_3$, —OR$_4$ or —SR$_4$ where $R_2$, $R_3$ and $R_4$ have the meanings given above;
(vi) the radical $R_7$ may also form, with one of bonds "i", "j", "k", or "g,h" taken with the radical $R_1$, or "f" taken with the radical $R_1$, a saturated hydrocarbon cycle containing a total of 3 to 8 carbon atoms, optionally comprising 1 to 5 heteroatoms selected from N, O, S, Si and P;

$R'_1$ represents a group selected from:
(i) a hydrogen atom;
(ii) a linear, branched or cyclic, saturated or unsaturated hydrocarbon group containing 1 to 30 carbon atoms optionally comprising 1 to 5 heteroatoms selected from N, O, S, Si and P and/or optionally halogenated or perhalogenated;
(iii) a group selected from —C(O)NR$_2$R$_3$, —NR$_2$R$_3$, —OR$_4$ and —SR$_4$, where $R_2$, $R_3$ and $R_4$ have the meanings given above;

$R'_2$ represents a group selected from:
(i) linear, branched or cyclic, saturated or unsaturated hydrocarbon groups containing 1 to 30 carbon atoms optionally comprising 1 to 5 heteroatoms selected from N, O, S, Si and P and/or optionally halogenated or perhalogenated;
(ii) halogen atoms;
(iii) —CN (nitrile), —COON (carboxylate), —NO$_2$ (nitro); —N═N— (azo); ═NH (imino); —CONH$_2$ (amide) groups;
(iv) a hydrogen atom;
(v) a group selected from —C(O)NR$_2$R$_3$, —NR$_2$R$_3$, —OR$_4$ or —SR$_4$ where $R_2$, $R_3$ and $R_4$ have the meanings given above.

Further examples of photochromic agents that may be mentioned are diarylethene, with formula

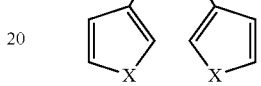

and its derivatives;
le dihydroazulene/vinylheptafulvene, with formula

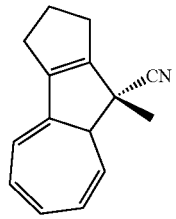 [SMILES: C[C@]1(C#N)C2=C(CCC2)C2=CC=CC=CC21]

and its derivatives;
spironaphthoxazine, with formula

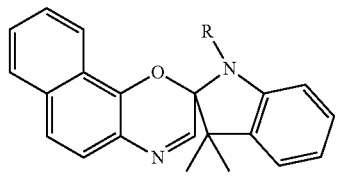

and its derivatives.

The photochromic agent may be an organic or inorganic compound. An organic photochromic agent may produce a more rapid and intense color change.

Examples of photochromic agents that may be mentioned are Photosol® from PPG, which changes color reversibly when activated by UV radiation with a wavelength in the range 300 nm to 360 nm, Reversacol® from J. ROBINSON and Photogenica® from CATALYST & CHEMICALS.

The photochromic agent may be attached to magnetic bodies, for example by coating magnetic cores with a substance containing said photochromic agent, thereby producing bodies containing magnetic grains and a synthetic matrix comprising the photochromic agent, or by forming chains of particles containing magnetic bodies and a photochromic agent. As an example, PHOTOGENICA pigments from CATALYST & CHEMICALS may be combined with those known under the reference STAPA WM IRON VP 041040 from ECKART.

Thermochromic Agents

A thermochromic agent is a pigment or colorant which can change color as a function of temperature.

As an example, the thermochromic agent may have a color that is lost when the temperature exceeds a certain value, for example about 15° C. or about 30° C., depending on the nature of the thermochromic agent.

The thermochromic agent may comprise capsules of a polymer containing a solvent, said solvent, if it has dissolved them, allowing the compounds to come into contact and modify the light absorption properties.

The color change may be reversible.

The thermochromic agent is, for example, attached to the magnetic bodies, in like manner to the photochromic agent, as discussed above.

As an example, it is possible to use the thermochromic agent sold with reference Kromafast® Yellow5GX 02 by KROMACHEM LTD, or Chromazone® as a powder or a dispersion, namely Thermobatch® or Thermostar®, from CHROMAZONE.

Piezochromic and Tribochromic Agents

A piezochromic agent can change color in the presence of a mechanical force.

An example of a piezochromic agent that may be mentioned is diphenylflavylene.

A tribochromic agent can change color in the presence of a mechanical force in a manner that lasts longer than with piezochromic agents.

Reference should be made in this regard to the patent publication WO-A-94/26729, the content of which is incorporated by reference.

Solvatochromic Agents

A solvatochromic agent can change color in the presence of at least one solvent.

DCRed27 dye is an example. In its anhydrous formulation, that compound is free of color. Adding water reveals a pink color.

Luminescent Agents

The composition may comprise at least one luminescent agent which is capable of assuming an excited state in the presence of an external stimulus; loss of that excited state is accompanied by emission of light in the visible region. Fluorescent, mechanoluminescent and phosphorescent agents are included in this category of luminescent agents.

Mechanoluminescent Agents

These agents are capable of emitting light when they are subject to mechanical stress such as a compression, shear or friction.

The mechanoluminescent agent is preferably in the form of particles which are insoluble in the cosmetic medium. The mean particle size is between 0.01 µm and 50 µm, preferably between 0.1 µm and 10 µm, for example.

Examples of mechanoluminescent materials that may be mentioned are:

a) complexes and chelates of lanthanides, such as those described in U.S. Pat. No. 6,071,632, US 2002/0015965 and WO 09/016,429 the contents of which are incorporated by reference. The rare earths are preferably selected from europium, terbium, samarium and dysprosium. In said materials, diketones are used as the ligand for the trivalent lanthanide salts. Said materials are in an organic medium.

b) Aluminates, silicates and aluminosilicates doped with rare earth ions such as those described in U.S. Pat. No. 6,280,655, EP 1 318 184, JP 2002/194349, JP 2004/59746, the contents of which are incorporated by reference, especially $(Sr,Mg,Ba,Zn,Ca)Al_2O_4$, $(SrLa,SrY)Al_3O_7$ $(Sr_2,SrMg,SrCa,SrBa)Al_6O_{11}$, $Sr_2(Mg,Al)$ $(Al,Si)$ $SiO_7$, $Sr(Zn,Mn,Fe,Mg)$ $Si_2O_6$. The elements in parentheses are completely or partially interchangeable. Ions of rare earths such as cerium, europium, samarium, neodymium, gadolinium, dysprosium and terbium may be used, alone or as a mixture. Europium and dysprosium are preferred.

c) Zinc sulfide, manganese sulfide, copper sulfide, cadmium sulfide or zinc oxide, optionally doped with transition metal ions or rare earth ions, as described in U.S. Pat. No. 6,117,574 and JP 2004/43656 the contents of which are incorporated by reference. Preferred transition metal ions are copper and manganese. Preferred rare earth ions are europium or cerium. Of said materials, ZnS:Mn is preferred.

The materials listed under b) and c) may be synthesized by solid phase reaction using a dry mixture followed by heat treatment and high temperature sintering, or by a sol-gel process followed by drying, heating and sintering. The sintering temperature is more than 1000° C., for example.

The materials listed under b) are preferred. Of these, $SrAl_2O_4$ and $SrMgAl_{10}O_{17}$ doped with rare earth metals are preferred.

Mechanoluminescent pigments $SrAl_2O_4$ doped with rare earth metal ions are sold with reference TAIKO-M1-1 by TAIKO Refractories Co., Ltd. The particles of this pigment have a diameter in the range 5 µm to 10 µm and a green luminescence under a small mechanical stress.

Fluorescent (ou Photoluminescent) Agents

This may be a compound which absorbs light in the ultraviolet and re-emits it in the visible region.

The fluorescent agent may, for example, comprise silicon nanoparticles such as those obtained using the processes described in WO-A-01/38222 and US 2002/0070121.

The fluorescent agent may comprise at least one rare earth.

The following publications: EP-A-0 962 224, U.S. Pat. No. 6,753,002, JP-A-2 805 373, FR-A-2 847 812 and FR-A-2 850 271 describe other photoluminescent agents.

Phosphorescent Agents

These are compounds which emit light in darkness.

Examples of phosphorescent compounds that may be mentioned are the LumiNova® pigment from Nemoto and Co Ltd, described in U.S. Pat. No. 5,424,006, herewith incorporated by reference.

Phosphorus sulphide (ZnS:Cu) is another example of a phosphorescent compound.

The phosphorescent compound may be incorporated into an inert matrix, or it may be coated to isolate it from the ambient medium.

Other Coloring Agents

The first composition may include at least one coloring agent producing light by absorbing at least a fraction of the visible spectrum.

Such a coloring agent, producing a color by an absorption phenomenon, may be constituted by a pigment that is an optionally magnetic, organic, or inorganic, or it may be a hybrid comprising both organic material and inorganic material.

The coloring agent may optionally be a particulate compound.

Where appropriate, the particles of a single magnetic pigment constitute both the coloring agent, producing the color by an absorption phenomenon, and the magnetic particles.

When the coloring agent includes a colorant, said colorant may be selected from amongst liposoluble and hydrosoluble colorants such as those listed further above.

The coloring agents may also be a lake or an organic pigment selected from lakes and organic pigments such as those listed further above.

Other Components

Typically, the cosmetic composition includes a physiologically acceptable medium. The term "physiologically acceptable medium" means a non-toxic medium that can be applied to the skin, to the nails, to hair, or to the lips of human beings. The physiologically acceptable medium is generally adapted to the nature of the surface onto which the composition is to be applied, and to the form in which the composition is packaged.

The first composition may include ingredients other than those described above, in particular at least one solvent, one oily phase, one film-forming polymer, and/or one dermatologically or cosmetically active ingredient, in particular as a function of its dosage or "galenical" form.

Solvents

The first composition may include at least one aqueous or organic solvent.

The first composition may advantageously include a volatile solvent, in particular a volatile organic solvent.

When the first composition contains one or more organic solvents, the solvents may be present in an amount in the range 0.1% to 99%, relative to the total weight of the composition under consideration.

Volatile Solvents

The term "volatile solvent" as used in the context of the present invention means a solvent that is liquid at ambient temperature, having a non-zero vapor pressure at ambient temperature and atmospheric pressure, in particular a vapor pressure in the range 0.13 pascals (Pa) to 40000 Pa ($10^{-3}$ millimeters of mercury (mm Hg) to 300 mm Hg), and preferably in the range 1.3 Pa to 13000 Pa (0.01 mm Hg to 100 mm Hg), and preferably in the range 1.3 Pa to 1300 Pa (0.01 mm Hg to 10 mm Hg).

In general, the quantity of solvent(s), in particular organic solvent(s), depends on the nature of the surface to which the composition is intended to be applied.

The solvent may be selected from water, organic solvents, and oils.

The first composition may include at least one volatile solvent constituted by a volatile oil.

The oil may be a siliconized oil or a hydrocarbonated oil, or may include a mixture of such oils.

The term "siliconized oil" as used in the context of the present invention means an oil including at least one silicon atom, and in particular at least one Si—O group.

The term "hydrocarbonated oil" means an oil containing mainly hydrogen and carbon atoms and possibly oxygen, nitrogen, sulfur, and/or phosphorus atoms.

The volatile hydrocarbonated oils may be selected from hydrocarbonated oils having 8 to 16 carbon atoms, and in particular $C_8$-$C_{16}$ branched alkanes (also termed isoparaffins) such as isododecane (also termed 2,2,4,4,6-pentamethylheptane), isodecane, isohexadecane, and oils sold under the trade names Isopars® or Permethyls®, for example.

Volatile oils that may also be used are volatile silicones, such as volatile linear or cyclic silicone oils, for example, in particular oils having a viscosity ≤8 centistokes (cSt) ($8*10^{-6}$ square meters per second ($m^2$/s)), and having in particular 2 to 10 silicon atoms, and in particular 2 to 7 silicon atoms, the silicones possibly including alkyl or alkoxy groups having 1 to 10 carbon atoms. In the invention, suitable volatile silicone oils that may be mentioned are in particular dimethicones having a viscosity of 5 cSt to 6 cSt, octa-methylcyclotetrasiloxane, decamethylcyclopentasiloxane, dodecamethylcyclohexasiloxane, heptamethylhexyltrisiloxane, heptamethyloctyltrisiloxane, hexamethyldi-siloxane, octamethyltrisiloxane, decamethyltetrasiloxane, dodecamethylpentasiloxane, and mixtures thereof.

Mention may also be made of volatile alkyltrisiloxane linear oils of general formula (I):

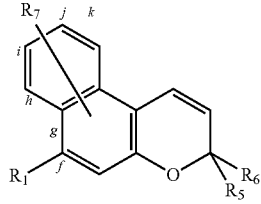

(I)

in which R represents an alkyl group comprising 2 to 4 carbon atoms and having one or more hydrogen atoms that can be substituted by a fluoride or chloride atom.

Amongst the oils of general formula (I), mention can be made of:
3-butyl 1,1,1,3,5,5,5-heptamethyltrisiloxane;
3-propyl 1,1,1,3,5,5,5-heptamethyltrisiloxane; and
3-ethyl 1,1,1,3,5,5,5-heptamethyltrisiloxane;
corresponding to oils of formula (I) for which R is respectively a butyl group, a propyl group, or an ethyl group.

It is also possible to use fluorinated volatile oils such as nonafluoromethoxybutane or perfluoromethylcyclo-pentane, and mixtures thereof.

The composition may contain 0.01% to 95% by weight of volatile oil relative to the total weight of the composition, and preferably 1% to 75% by weight.

The first composition may comprise at least one organic solvent selected from the following list:
ketones that are liquid at ambient temperature, such as methylethylketone, methylisobutylketone, diisobutylketone, isophorone, cyclohexanone, or acetone;
alcohols that are liquid at ambient temperature, such as ethanol, isopropanol, diacetone alcohol, 2-butoxyethanol, or cyclohexanol;
glycols that are liquid at ambient temperature, such as ethylene glycol, propylene glycol, pentylene glycol, or glycerol;
propylene glycol ethers that are liquid at ambient temperature, such as propylene glycol monomethyl ether, the acetate of propylene glycol monomethyl ether, or dipropylene glycol mono n-butyl ether;
short-chain esters (containing a total of 3 to 8 carbon atoms), such as ethyl acetate, methyl acetate, propyl acetate, n-butyl acetate, or isopentyl acetate; and
alkanes that are liquid at ambient temperature, such as decane, heptane, dodecane, or cyclohexane.

The first composition may also comprise water or a mixture of water and hydrophilic organic solvents which are routinely used in cosmetics, such as alcohols, in particular linear or branched lower monoalcohols containing 2 to 5 carbon atoms, such as ethanol, isopropanol or n-propanol, polyols such as glycerine, diglycerine, propylene glycol, sorbitol, penthylene glycol, or polyethylene glycols. The first composition may also contain hydrophilic C2 ethers and C2-C4 aldehydes. The water or mixture of water and hydrophilic organic solvents may be present in the first and/or second composition in an amount in the range 0% to 90%, in particular 0.1% to 90% by weight, and preferably 0% to 60% by weight, more particularly 0.1% to 60% by weight relative to the total weight of the composition.

Oily Phase

When it is to be applied to the lips or the eyelashes, the first composition may, for example, include an oily phase and in particular at least one fat that is liquid at ambient temperature (25° C.) and under atmospheric pressure (760 mm of Hg) and/or a fat that is solid at ambient temperature, such as waxes, pasty fats, gums, and mixtures thereof. The oily phase may also contain lipophilic organic solvents.

By way of example, the first composition may have a continuous oily phase which may contain less than 5% water, in particular less than 1% water relative to its total weight, and in particular it may be in the anhydrous form.

Fats that are liquid at ambient temperature, usually termed "oils", that may be mentioned are: hydrocarbon-containing vegetable oils such as liquid fatty acid triglycerides containing 4 to 10 carbon atoms, for example heptanoic or octanoic acid triglycerides, or sunflower, corn, soybean, grapeseed, sesame seed, apricot kernel, macadamia nut, castor, or avocado stone oil, caprylic/capric acid triglycerides, jojoba oil, shea nut butter oil, lanolin, acetylated lanolin; linear or branched hydrocarbons of mineral or synthetic origin, such as paraffin oils and their derivatives, Vaseline, polydecenes, hydrogenated polyisobutene such as Parleam; synthesized esters and ethers, in particular fatty acids such as Purcellin oil, isopropyl myristate, 2-ethylhexyl palmitate, 2-octyldodecyl stearate, 2-octyldodecyl erucate, isostearyl isostearate; hydroxylated esters such as isostearyl lactate, octylhydroxystearate, octyldodecyl hydroxystearate, diisostearylmalate, triisocetyl citrate, fatty alcohol heptanoates, octanoates, or decanoates; isononyl isonanoate, isopropyl lanolate, tridecyl trimellilate, diisostearyl malate; polyol esters such as propylene glycol dioctanoate, neopentylglycol diheptanoate, diethyleneglycol diisononanoate; and pentaerythritol esters; fatty alcohols containing 12 to 26 carbon atoms, such as octyldodecanol, 2-butyloctanol, 2-hexyldecanol, 2-undecylpentadecanol, or oleic alcohol; partially hydrocarbonated and/or siliconized fluorinated oils; silicone oils such as volatile or non-volatile, linear or cyclic polymethylsiloxanes (PDMS) which may be liquid or pasty at ambient temperature, such as cyclo-methicones or dimethicones, optionally comprising a phenyl group, such as phenyl trimethicones, phenyltri-methylsiloxydiphenyl siloxanes, diphenylmethyldimethyl-trisiloxanes, diphenyl dimethicones, phenyl dimethicones, polymethylphenylsiloxanes; and mixtures thereof. The oils may be present in an amount in the range 0.01% to 90%, and preferably 0.1% to 85% by weight relative to the total weight of the composition.

The presence of an oily phase may impart a gloss effect, and may present a refractive index in the range 1.47 to 1.51, for example, and preferably in the range 1.48 to 1.50. The refractive index is measured at ambient temperature (25° C.) by means of a refractometer.

The first composition may comprise a pasty fat, a wax, or a gum.

The composition may include at least one structuring agent for the liquid oily phase (formed by the above-described volatile or non-volatile organic solvents and/or oils) selected from waxes, semi-crystalline polymers, lipophilic gelling agents, and mixtures thereof.

Pasty fats are generally hydrocarbon-containing compounds with a melting point in the range 25° C. to 60° C., preferably in the range 30° C. to 45° C., and/or with hardness in the range 0.001 megapascals (MPa) to 0.5 MPa, preferably in the range 0.005 MPa to 0.4 MPa, such as lanolins and derivatives thereof.

Waxes may be solid at ambient temperature (25° C.) with a reversible solid/liquid change of state, with a melting point of more than 30° C. and up to 200° C., a hardness of more than 0.5 MPa, and with an anisotropic crystalline organization in the solid state. In particular, the waxes may have a melting point of more than 25° C., and preferably more than 45° C. The waxes may be hydrocarbon-containing, fluorinated and/or siliconized and may be of animal, mineral, vegetable and/or synthetic origin. Suitable waxes that may be mentioned are beeswax, carnauba wax or candellila wax, paraffin, micro-crystalline waxes, ceresin, or ozokerite; synthetic waxes such as polyethylene or Fischer-Tropsch waxes or silicone waxes such as alkyl or alkoxy-dimethicone containing 16 to 45 carbon atoms. The composition may contain 0 to 50% by weight of waxes relative to the total weight of the composition, or even 1% to 30% by weight.

Suitable gums are generally high molecular weight polydimethylsiloxanes (PDMS) or cellulose gums or polysaccharides.

In accordance with an aspect of the invention, the composition applied contains at least one film-forming polymer.

Film-Forming Polymer

By way of example, the first composition may also include a film-forming polymer, in particular for a mascara, a nail varnish or a foundation. The term "film-forming polymer" means a polymer that can form, by itself or in the presence of an additional film-forming agent, a continuous film, preferably a cohesive film, and better still a film having cohesion and mechanical properties such that said film may be isolated from said surface, that adheres to a surface, in particular to keratinous materials.

Suitable film-forming polymers for use in the first composition in accordance with the invention that may be mentioned include synthetic polymers, of the radical or polycondensate type, natural polymers such as nitrocellulose or cellulose esters, and mixtures thereof.

Radical type film-forming polymers may in particular be vinyl polymers or copolymers, in particular acrylic polymers.

Vinyl film-forming polymers may result from polymerizing monomers with an ethylenically unsaturated bond containing at least one acid group and/or esters of said acid monomers and/or amides of said acid monomers, such as α,β-ethylenically unsaturated carboxylic acids, for example acrylic acid, methacrylic acid, crotonic acid, maleic acid, or itaconic acid.

Vinyl film-forming polymers may also result from homopolymerizing or copolymerizing monomers selected from vinyl esters such as vinyl acetate, vinyl neodecanoate, vinyl pivalate, vinyl benzoate, and vinyl t-butyl benzoate, and styrene monomers such as styrene and alpha-methyl styrene.

Examples of film-forming polycondensates that may be mentioned include polyurethanes, polyesters, polyester amides, polyamides, and polyureas, this list not being limiting.

Polymers of natural origin, which may optionally be modified, may be selected from shellac resin, gum sandarac, dammar resin, gum elemi, copal resin, cellulose polymers such as nitrocellulose, ethylcellulose, or nitrocellulose esters selected, for example, from cellulose acetate, cellulose acetobutyrate, and cellulose acetopropionate, and mixtures thereof.

The film-forming polymer may be present in the form of solid particles in an aqueous or oily dispersion, generally known as latexes or psuedolatexes. The film-forming polymer may comprise one or more stable dispersions of generally spherical polymer particles of one or more polymers in a physiologically acceptable liquid oily phase. Said dispersions are generally termed polymer NADs (non-aqueous dispersions), in contrast to latexes which are aqueous polymer dispersions. Said dispersions may be in the form of nanoparticles of polymers in stable dispersion in said oily phase. The nanoparticle size is preferably in the range 5 nm to 600 nm. Techniques for preparing said dispersions are well known to the person skilled in the art.

Aqueous film-forming polymer dispersions which may be used are acrylic dispersions sold under the trade names NEOCRYL XK-90®, NEOCRYL A-1070®, NEOCRYL A-1090®, NEOCRYL BT-62® NEOCRYL A-1079®, NEOCRYL A-523® by AVECIA-NEORESINS, and DOW LATEX 432® by DOW CHEMICAL; DAITOSOL 5000 AD® by DAITO KASEI KOGYO; or aqueous polyurethane dispersions sold under the trade names NEOREZ R-981® and NEOREZ R-974® by AVECIA-NEORESINS; AVALURE UR-405®, AVALURE tJR-410®, AVALURE UR-425®, AVALURE UR-450®, SANCURE 875®, SANCURE 861®, SANCURE 878®, and SANCURE 2060® by GOODRICH; IMPRANIL 85® by BAYER; AQUAMERE H-1511' by HYDROMER; and sulfopolyesters sold under the trade mark Eastman AQ by Eastman Chemical Products.

In an embodiment of the invention, the composition includes at least one film-forming polymer that is a film-forming linear sequenced ethylene polymer. The polymer preferably comprises at least a first sequence and at least a second sequence having different glass transition temperatures (Tg), said first and second sequences being connected together by an intermediate sequence comprising at least one monomer that constitutes the first sequence and at least one monomer that constitutes the second sequence.

The first and second sequences of the sequenced polymer are advantageously incompatible with each other.

By way of example, such polymers are described in documents EP 1 411 069 or WO04/028488 which are incorporated herein by reference.

The first composition of the invention may also comprise an auxiliary film-forming agent which encourages the formation of a film with the film-forming polymer.

As film-forming polymers, mention may be made in particular of acrylic polymers, polyurethanes, polyesters, polyamides, polyureas, and cellulose/cellulosic polymers, such as nitrocellulose.

Said film-forming polymers may be separated into four categories depending on their solubility as regards an aqueous phase or a liquid oily phase.

In one example, the film-forming polymer is at least one polymer selected from the group comprising:

film-forming polymers that are soluble in the liquid oily phase of the composition, in particular liposoluble polymers;

film-forming polymers that are dispersible in the liquid oily phase of the composition, in particular polymers in the form of non-aqueous dispersions of polymer particles, in particular dispersions in silicone or hydrocarbon oils;

aqueous dispersions of particles of film-forming polymers, usually termed "latexes"; in this case, in addition to the liquid oily phase, the composition must include an aqueous phase;

hydrosoluble film-forming polymers; in this case also, the composition must include an aqueous phase in addition to the liquid oily phase.

In a further implementation of the invention, the film-forming polymer contains silicone and may be selected from polymers with a non-silicone organic backbone grafted with monomers containing a polysiloxane.

In a further implementation of the invention, the film-forming polymer contains silicone and is selected from silicone polymers grafted with non-silicone organic monomers. Said polymers may be liposoluble, lipodispersible, hydrosoluble, or dispersible in an aqueous medium, as appropriate.

For obvious reasons, the quantities of film-forming agent in the compositions of the invention can vary significantly, especially as a function of the nature of the film-forming agent under consideration and also of the desired qualities of the composition into which it is incorporated.

Thus, the cosmetic compositions of the invention may contain an amount of film-forming polymer(s) which can be from 0.01% to 65% by weight, especially 0.1% to 60% by weight, in particular 1% to 45% by weight relative to the total composition weight.

The composition may comprise, as a polymer, a dispersion of particles of a graft ethylenic polymer in a liquid oily phase.

The term "ethylenic" polymer means a polymer obtained by polymerizing monomers comprising an ethylenically unsaturated bond.

The dispersion of graft ethylenic polymer is exempt of stabilizing polymer which is distinct from said graft polymer, such as those described in EP-A-0 749 747 and described below, and the surfaces of the particles of graft ethylenic polymer are thus not stabilized by said additional stabilizing polymers. The graft polymer is thus dispersed in the liquid oily phase in the absence of additional stabilizer at the particle surface.

The term "graft" polymer means a polymer having a backbone comprising at least one pendant side chain or chain located at a chain end, preferably a pendant chain.

Advantageously, the graft ethylenic polymer comprises an ethylenic backbone that is insoluble in the liquid oily phase, and side chains which are covalently bonded to said backbone and are soluble in the liquid oily phase.

In particular, the graft ethylenic polymer is a non cross-linked polymer. In particular, the polymer is obtained by polymerizing monomers comprising a single polymerizable group.

The graft ethylenic polymer is a graft acrylic polymer, for example.

The graft ethylenic polymer is capable of being obtained by radical polymerization, in an organic polymerization medium, of:

at least one ethylenic monomer, in particular at least one acrylic monomer and optionally at least one additional non-acrylic vinyl monomer, to form said insoluble backbone; and at least one macromonomer comprising a terminal polymerizable group to form side chains, said macromonomer having a mass average molecular weight of 200 or more and the amount of polymerized macromonomer representing 0.05% to 20% by weight of polymer.

The liquid oily phase may contain the organic medium for polymerizing the graft ethylenic polymer.

The liquid organic dispersion medium, corresponding to the medium in which the graft polymer is supplied, may be identical to the polymerization medium.

However, the polymerization medium may be wholly or partially substituted by another liquid organic medium. After polymerization, said other liquid organic medium may be added, to the polymerization medium. The medium is then completely or partially evaporated off.

The liquid oily phase may contain liquid organic compounds other than those present in the dispersion medium.

Said other compounds are selected so that the graft polymer remains in the dispersed state in the liquid oily phase.

The liquid organic dispersion medium may be present in the liquid oily phase of the composition of the invention because the graft polymer dispersion obtained is introduced into the composition.

The liquid oily phase preferably mainly comprises one or more liquid organic compounds (or oils) as defined below.

In particular, the liquid oily phase may be a non-aqueous liquid organic phase which is not miscible with water at ambient temperature (25° C.).

The term "liquid organic compound" means a non-aqueous compound which is in the liquid state at ambient temperature (25° C.) and which thus flows under its own weight.

Examples of liquid organic compounds or oils which may be present in the liquid organic dispersion medium that may be mentioned are:

liquid organic compounds, in particular non-silicone or silicone, having an overall solubility parameter in the Hansen solubility space of 18 $(MPa)^{1/2}$ or less, preferably 17 $(MPa)^{1/2}$ or less;

mono-alcohols having an overall solubility in the Hansen solubility space of 20 $(MPa)^{1/2}$ or less; and mixtures thereof.

The overall solubility parameter $\delta$ in the Hansen solubility space is defined in the article "Solubility parameter values" by Eric A Grulke in the "Polymer Handbook", $3^{rd}$ edition, Chapter VII, p 519-559 by the relationship:

$$\delta = (\delta_D^2 + \delta_P^2 + \delta_H^2)^{1/2}$$

in which:

$\delta d_D$ characterizes the LONDON dispersion forces from the formation of dipoles induced during molecular impacts;

$\delta_P$ characterizes the DEBYE interaction forces between permanent dipoles; and $\delta_H$ characterizes the specific interaction forces (hydrogen bonds, acid/base, donor/acceptor, etc).

The definition of solvents in the Hansen solubility space is described in the article by C M Hansen, "The three-dimensional solubility parameters", J. Paint Technology, 39, 105 (1967).

Examples of organic liquid compounds, especially non-silicone or silicone, with an overall solubility parameter in the Hansen solubility space of 18 $(MPa)^{1/2}$ or less that may be mentioned are liquid fats, especially oils, which may be selected from carbon-containing, hydrocarbon-containing, fluorinated, silicone, optionally branched natural or synthetic oils, used alone or as a mixture.

Of said oils, the following may be mentioned: vegetable oils formed by esters of fatty acids and polyols, in particular triglycerides, such as sunflower seed oil, sesame seed oil or rapeseed oil, or esters derived from long chain alcohols or acids (i.e. containing 6 to 20 carbon atoms), especially esters with formula RCOOR' in which R represents the residue of a higher fatty acid containing 7 to 19 carbon atoms and R' represents a hydrocarbon chain containing 3 to 20 carbon atoms, such as palmitates, adipates, or benzoates, especially diisopropyl adipate.

Linear, branched, and/or cyclic alkanes, which may be volatile, may also be mentioned, in particular paraffin oil, Vaseline oil or hydrogenated polyisobutylene, isododecane or ISOPARS, which are volatile isoparaffins. Esters, ethers and ketones may also be mentioned.

It is also possible to mention silicone oils such as polydimethylsiloxanes and polymethylphenylsiloxanes, optionally substituted with aliphatic and/or aromatic groups, optionally fluorinated, or by functional groups such as hydroxyl groups, thiols and/or amines, and volatile silicone oils, in particular cyclic oils.

In particular, silicone oils, which may be branched, volatile, and/or non volatile, may be mentioned.

In particular, the following non-silicone liquid organic compounds with an overall solubility in the Hansen solubility space of 18 $(MPa)^{1/2}$ or less may be mentioned:

linear, branched or cyclic esters containing at least 6 carbon atoms, especially 6 to 30 carbon atoms;

ethers containing at least 6 carbon atoms, especially 6 to 30 carbon atoms; and ketones containing at least 6 carbon atoms, especially 6 to 30 carbon atoms.

The term "liquid mono-alcohols having an overall solubility parameter in the Hansen solubility space of 20 $(MPa)^{1/2}$" means liquid aliphatic fatty mono-alcohols containing 6 to 30 carbon atoms, the hydrocarbon chain having no substitution group. Mono-alcohols in accordance with the invention that may be mentioned are oleic alcohol, decanol, octyldodecanol and linoleic alcohol.

When the liquid oily phase of the composition is a non-silicone liquid oily phase, the macromonomers present in the grafted polymer are advantageously carbon-containing macromonomers as described below.

In particular, when the liquid oily phase of the composition is a non-silicone liquid oily phase, the graft polymer present in the composition is advantageously a non-silicone graft polymer.

The term "non-silicone graft polymer" means a graft polymer containing a mainly carbon-containing macromonomer and optionally containing at most 7% by weight, preferably at most 5% by weight or even no silicone macromonomer.

When the liquid oily phase of the cosmetic composition of the invention is a silicone liquid oily phase, the macromonomers present in the graft polymer are advantageously silicone macromonomers as described below.

In particular, when the liquid oily phase is a silicone liquid oily phase, the graft polymer present in the composition is advantageously a silicone graft polymer.

The term "silicone graft polymer" means a graft polymer mainly containing a silicone macromonomer and optionally containing at most 7% by weight, preferably at most 5% by weight, or even no carbon-containing macromonomer.

a) Monomers

The choice of monomers constituting the backbone of the polymer, the macromonomers, the molecular weight of the polymer, and the proportion of monomers and macromonomers may be made as a function of the liquid organic dispersion medium to advantageously obtain a dispersion of particles of graft polymers, in particular a stable dispersion; this choice can be made by the skilled person.

The term "stable dispersion" means a dispersion which is not capable of forming a solid deposit or of liquid/solid phase separation, in particular after centrifuging, for example at 4000 rpm for 15 minutes.

The graft ethylenic polymer forming the particles in dispersion thus comprises a backbone that is insoluble in said dispersion medium and a portion that is soluble in said dispersion medium.

The graft ethylenic polymer may be a random polymer.

In accordance with the invention, the term "graft ethylenic polymer" means a polymer that can be obtained by radical polymerization:
of one or more ethylenic monomer(s);
with one or more macromonomer(s) in an organic polymerization medium.

According to the invention, the term "graft acrylic polymer" means a polymer that can be obtained by radical polymerization:
of one or more acrylic monomers, and optionally one or more additional non-acrylic vinyl monomer(s);
with one or more macromonomer(s) in an organic polymerization medium.

Advantageously, the acrylic monomers represent 50% to 100% by weight, preferably 55% to 100% by weight (in particular 5% to 95% by weight), preferably 60% to 100% by weight (in particular 60% to 90% by weight) of the (acrylic monomer+any non-acrylic vinyl monomer) mixture.

In particular, the acrylic monomers are selected from monomers, the homopolymer of which is insoluble in the dispersion medium under consideration, i.e. the homopolymer is in the solid (or undissolved) form at a concentration of 5% by weight or more at ambient temperature (20° C.) in said dispersion medium.

According to the invention, the term "macromonomer having a polymerizable terminal group" means any polymer having at only one of its ends a polymerizable terminal group that can react during the polymerization reaction with the acrylic monomers and the optional additional non-acrylic vinyl monomers constituting the backbone. The macromonomer can form side chains of graft acrylic polymer. The polymerizable group of the macromonomer may advantageously be a group with an ethylenically unsaturated bond that can polymerize by radical polymerization with the monomers constituting the backbone.

The term "carbon-containing macromonomer" means a non-silicone macromonomer, especially an oligomeric macromonomer obtained by polymerizing non-silicone monomer(s) with an ethylenically unsaturated bond, and principally by polymerizing acrylic and/or non-acrylic vinyl monomers.

The term "silicone macromonomer" means an organopolysiloxane macromonomer, in particular a polydimethylsiloxane macromonomer.

In particular, the macromonomer is selected from macromonomers the homopolymer of which is soluble in the dispersion medium under consideration, i.e. completely dissolved in a concentration which is 5% by weight or more and at ambient temperature in said dispersion medium.

Thus, the graft acrylic polymer includes a backbone (or principal chain) constituted by a concatenation of acrylic patterns especially resulting from polymerization of one or more acrylic monomers and side chains (or grafts) derived from reacting the macromonomers, said side chains being covalently bonded to said principal chain.

The backbone (or principal chain) is insoluble in the dispersion medium under consideration, while the side chains (or grafts) are soluble in said dispersion medium.

The term "acrylic monomer" as used in the present application means monomers selected from (meth)acrylic acid, esters of (meth)acrylic acid (also termed (meth)acrylates), and amides of (meth)acrylic acid (also termed (meth) acrylamides).

Examples that may be mentioned of acrylic monomers that can be used to form the insoluble polymer backbone when used alone or as a mixture are as follows, along with salts thereof:

i) (meth)acrylates with formula (VIII):

in which:
$R_1$ designates a hydrogen atom or a methyl group;
$R_2$ represents a group selected from:
a linear or branched alkyl group containing 1 to 6 carbon atoms, said group possibly comprising one or more heteroatoms selected from O, N and S in its chain; and/or possibly comprising one or more substituents selected from —OH, halogen atoms (F, Cl, Br, I) and —NR'R", where R' and R", which may be identical or different, are selected from linear or branched $C_1$-$C_4$ alkyls; and/or possibly substituted with at least one polyoxyalkylene group, in particular with $C_2$-$C_4$ alkylene, in particular polyoxyethylene and/or polyoxypropylene, said polyoxyalkylene being constituted by repeating 5 to 30 oxyalkylene patterns;
a cyclic alkyl group containing 3 to 6 carbon atoms, said group possibly comprising one or more heteroatoms selected from O, N and S in its chain, and/or possibly comprising one or more substituents selected from OH and halogen atoms (F, Cl, Br, I).

Examples of $R_2$ that may be mentioned are methyl, ethyl, propyl, butyl, isobutyl, methoxyethyl, ethoxyethyl, methoxy-polyoxyethylene 350 OE, trifluoroethyl, 2-hydroxyethyl, 2-hydroxypropyl, dimethylaminoethyl, diethylaminoethyl and dimethylaminopropyl.

ii) (meth)acrylamides with formula (IX):

in which:
$R_3$ designates a hydrogen atom or a methyl group;
$R_4$ and $R_5$, which may be identical or different, represent a hydrogen atom or a linear or branched alkyl group containing 1 to 6 carbon atoms, possibly comprising one or more substituents selected from —OH, halogen atoms (F, Cl, Br, I) and —NR'R" where R' and R", which may be identical or different, are selected from linear or branched alkyls $C_1$-$C_4$; or
$R_4$ represents a hydrogen atom and $R_5$ represents a 1,1-dimethyl-3-oxobutyl group.

Examples of alkyl groups which may constitute $R_4$ and $R_5$, that may be mentioned are n-butyl, t-butyl, n-propyl, dimethylaminoethyl, diethylaminoethyl and dimethylaminopropyl:

iii) (meth)acrylic monomers comprising at least one carboxylic, phosphoric or sulfonic acid function, such as acrylic acid, methacrylic acid or acrylamidopropanesulfonic acid.

Particular acrylic monomers that may be mentioned are methyl, ethyl, propyl, butyl and isobutyl(meth)acrylates; methoxyethyl or ethoxyethyl(meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate, 2-hydroxyethyl acrylate; dimethylaminopropyl methacrylamide; salts thereof; and mixtures thereof.

In particular, the acrylic monomers are selected from methyl acrylate, methoxyethyl acrylate, methyl methacrylate, 2-hydroxyethyl methacrylate, acrylic acid, dimethylaminoethyl methacrylate, and mixtures thereof.

Additional non-acrylic vinyl monomers that may be mentioned include:
vinyl esters with the following formula:

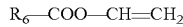

in which:

$R_6$ represents a linear or branched alkyl group containing 1 to 6 atoms, or a cyclic alkyl group containing 3 to 6 carbon atoms and/or an aromatic group, for example of the benzene, anthracene or naphthalene type;

non-acrylic vinyl monomers comprising at least one carboxylic, phosphoric or sulfonic acid function, such as crotonic acid, maleic anhydride, itaconic acid, fumaric acid, maleic acid, styrenesulfonic acid, vinylbenzoic acid or vinylphosphoric acid, and salts thereof;

non-acrylic vinyl monomers comprising at least one tertiary amine function, such as 2-vinylpyridine or 4-vinylpyridine; and
mixtures thereof.

Advantageously, acrylic monomers present in the graft polymer comprise at least one (meth)acrylic acid and at least one monomer selected from the (meth)acrylates and (meth)acrylamides described above under points i) and ii). Preferably, the acrylic monomers comprise at least one (meth)acrylic acid and at least one monomer selected from $C_1$-$C_3$ alkyl(meth)acrylates. The (meth)acrylic acid may be present in an amount of at least 5% by weight relative to the total polymer weight, especially from 5% to 80% by weight, preferably at least 10% by weight, in particular from 10% by weight to 70% by weight, preferably at least 15% by weight, in particular 15% to 60% by weight.

Salts that may be mentioned include those obtained by neutralizing acid groups using inorganic bases such as sodium hydroxide, potassium hydroxide, or ammonium hydroxide or alkanolamine type organic bases such as monoethanolamine, diethanolamine, triethanolamine or 2-methyl-2-amino-1-propanol.

Salts formed by neutralizing tertiary amine moieties, for example using a mineral or organic acid, may also be mentioned. Mineral acids that may be mentioned include sulfuric acid and hydrochloric acid, hydrobromic acid, hydroiodic acid, phosphoric acid and boric acid. Organic acids that may be mentioned include acids comprising one or more carboxylic, sulfonic or phosphonic groups. It may concern linear, branched or cyclic aliphatic acids, or aromatic acids. Said acids may also include one or more heteroatoms selected from O and N, for example in the form of hydroxyl groups. In particular, acetic acid and propionic acid, terephthalic acid and citric and tartaric acid may be mentioned.

In one implementation of the invention, the graft ethylenic polymer contains no additional non-acrylic vinyl monomers as described above. In this implementation, the insoluble backbone of the graft ethylenic polymer is formed solely of acrylic monomers as described above.

It should be understood that these non-polymerized acrylic monomers may be soluble in the dispersion medium under consideration, but the polymer formed with said monomers is insoluble in the dispersion medium.

In a particular implementation of the invention, the ethylenic graft polymer may be obtained by radical polymerization in an organic polymerization medium:

of a principal acrylic monomer selected from $C_1$-$C_3$ alkyl(meth)acrylates, used alone or as a mixture, and optionally one or more additional acrylic monomers selected from (meth)acrylic acid, methacrylic acid and alkyl(meth)acrylates with formula (X) defined below, and salts thereof, to form said insoluble backbone; and of at least one silicone macromonomer comprising a polymerizable terminal group as defined above.

The principal acrylic monomer may be methyl acrylate, methyl methacrylate, ethyl acrylate, ethyl methacrylate, n-propyl acrylate, n-propyl methacrylate, isopropyl acrylate or isopropyl methacrylate, and mixtures thereof.

More particularly, methyl acrylate, methyl methacrylate and ethyl methacrylate may be mentioned.

The additional acrylic monomers may be selected from:
(meth)acrylic acid and salts thereof;
(meth)acrylates with formula (X) and salts thereof:

in which:

$R'_1$ designates a hydrogen atom or a methyl group;
$R'_2$ represents:

a linear or branched alkyl group containing 1 a 6 carbon atoms, said group comprising one or more oxygen atoms in its chain and/or comprising one or more substituents selected from —OH, halogen atoms (F, Cl, Br, I) and —NR'R" where R' and R", which may be identical or different, are selected from linear or branched $C_1$-$C_3$ alkyls;

a cyclic alkyl group containing 3 to 6 carbon atoms, said group possibly comprising in its chain one or more oxygen atoms and/or possibly comprising one or more substituents selected from OH and halogen atoms (F, Cl, Br, I); and
mixtures thereof.

Examples of $R'_2$, that may be mentioned include methoxyethyl, ethoxyethyl, trifluoroethyl; 2-hydroxyethyl, 2-hydroxypropyl, dimethylaminoethyl, diethylaminoethyl and dimethylaminopropyl.

More particular additional acrylic monomers that may be mentioned include (meth)acrylic acid, methoxyethyl or ethoxyethyl(meth)acrylates; trifluoroethyl methacrylate; dimethylaminoethyl methacrylate, diethylaminoethyl methacrylate, 2-hydroxypropyl methacrylate, 2-hydroxyethyl methacrylate, 2-hydroxypropyl acrylate, 2-hydroxyethyl acrylate, salts and mixtures thereof.

More particularly, acrylic acid and methylacrylic acid may be mentioned.

b) Macromonomers

Macromonomers include a polymerizable terminal group at one end of the chain which can react during polymerization with acrylic monomers, and optional additional vinyl monomers, to form the side chains of the graft ethylenic polymer. Said polymerizable terminal group may in particular be a vinyl group or a (meth)acrylate (or (meth)acryloxy) group, preferably a (meth)acrylate group.

The macromonomers are preferably selected from macromonomers wherein the homopolymer has a glass transition temperature (Tg) of 25° C. or less, especially from −100° C. at 25° C., preferably from −80° C. to 0° C.

The macromonomers have a mass average molecular mass of 200 or more, preferably 300 or more, more preferably 500 or more, and still more preferably more than 600.

Preferably, the macromonomers have a mass average molecular mass (Mw) of 200 to 100000, preferably 500 to 50000, more preferably 800 to 20000, still more preferably 800 to 10000 and still more preferably 800 to 6000.

In the present application, the mass average molecular masses (Mw) and number average molecular masses (Mn) were determined by gel permeation liquid chromatography (THF solvent, calibration curve established with linear polystyrene specimens, refractometric detector).

Particular carbon-containing macromonomers that may be mentioned are:

i) linear or branched $C_8$ to $C_{22}$ alkyl(meth)acrylate homopolymers and copolymers having a polymerizable terminal group selected from vinyl or (meth)acrylate groups, in particular: macromonomers of poly(ethyl-2 hexyl acrylate) with a mono(meth)acrylate end; macromonomers of poly (dodecyl acrylate) or poly(dodecyl methacrylate) with a mono(meth)acrylate end; macromonomers of poly(stearyl acrylate) or poly(stearyl methacrylate) with a mono(meth) acrylate end.

Such macromonomers have in particular been described in patents EP-A-0 895 467 and EP-A-0 096 459 and in the article by Gillman K. F., Polymer Letters, Vol 5, page 477-481 (1967).

In particular, macromonomers based on poly(2-ethylhexyl acrylate) or poly(dodecyl acrylate) with a mono(meth) acrylate end may be mentioned.

ii) polyolefins having a terminal group with an ethylenically unsaturated bond, in particular a (meth)acrylate terminal group. Particular examples of said polyolefins that may be mentioned are the following macromonomers, it being understood that they have a (meth)acrylate terminal group: polyethylene macromonomers, polypropylene macromonomers, polyethylene/polypropylene copolymer macromonomers, polyethylene/polybutylene copolymer macromonomers, polyisobutylene macromonomers; polybutadiene macromonomers; polyisoprene macromonomers; polybutadiene macromonomers; and poly(ethylene/butylene)-polyisoprene macromonomers.

Such macromonomers have in particular been described in U.S. Pat. No. 5,625,005 which mentions ethylene/butylene macromonomers and ethylene/propylene macromonomers with a reactive (meth)acrylate terminal group.

In particular, poly(ethylene/butylenes) methacrylate may be mentioned, such as that sold under the trade name KRATON LIQUID L-1253 by KRATON POLYMERS.

Examples of silicone macromonomers that may be mentioned are polydimethylsiloxanes with a mono(meth)acrylate terminal group, in particular those with the following formula (XI):

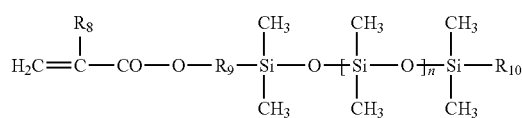

(XI)

in which:

$R_8$ designates a hydrogen atom or a methyl group;

$R_9$ designates a divalent hydrocarbon group containing 1 to 10 carbon atoms and optionally containing one or two ether bonds, —O—;

$R_{10}$ designates an alkyl group containing 1 to 10 carbon atoms, especially 2 to 8 carbon atoms; and n designates a whole number from 1 to 300, preferably 3 to 200, and preferably 5 to 100.

Examples of silicone macromonomers which may be used are monomethacryloxypropyl polydimethylsiloxanes such as those sold under the trade name PS560-K6 by UNITED CHEMICAL TECHNOLOGIES INC. (UCT) or under the trade name MCR-M17 by GELEST INC.

More particularly, the polymerized macromonomer (constituting the side chains of the graft polymer) represents 0.1% to 15% by weight of the total polymer weight, preferably 0.2% to 10% by weight, and more preferably 0.3% to 8% by weight.

Particularly advantageous graft ethylenic polymers dispersed in a non-silicone liquid oily phase which may be used are those obtained by polymerizing:

methyl acrylate and polyethylene/polybutylene macromonomer with a methacrylate terminal group (in particular KRATON L-1253), in particular in a solvent selected from isododecane, isononyl isononanoate, octyldodecanol, diisostearyl malate, and a $C_{12}$-$C_{15}$ alkyl benzoate (such as Finsolv TN);

methoxyethyl acrylate and polyethylene/polybutylene macromonomer with a methacrylate terminal group (especially KRATON L-1253), in particular in isododecane;

methyl acrylate/methyl methacrylate monomers and polyethylene/polybutylene macromonomer with a methacrylate terminal group (especially KRATON L-1253), in particular in isododecane;

methyl acrylate/acrylic acid monomers and polyethylene/polybutylene macromonomer with a methacrylate terminal group (in particular KRATON L-1253), in particular in isododecane;

methyl acrylate/dimethylaminoethyl methacrylate monomers and polyethylene/polybutylene macromonomer with a methacrylate terminal group (especially KRATON L-1253), in particular in isododecane;

methyl acrylate/2-hydroxyethyl methacrylate monomers and polyethylene/polybutylene macromonomer with a methacrylate terminal group (especially KRATON L-1253), in particular in isododecane.

In particular, the graft acrylic polymer dispersed in a silicone liquid oily phase may be selected from those obtained by polymerizing:

methyl acrylate and monomethacryloxypropylpolydimethylsiloxane macromonomer with a mass average molecular mass of 800 to 6000, in particular in decamethylcyclopentasiloxane or phenyltrimethicone;

methyl acrylate, acrylic acid and monomethacryloxypropylpolydimethylsiloxane macromonomer with a mass average molecular mass of 800 to 6000, in particular in decamethylcyclopentasiloxane or phenyltrimethicone.

In particular, the graft polymer has a mass average molecular mass (Mw) in the range 10000 to 300000, especially in the range 20000 to 200000, more preferably in the range 25000 to 150000.

Because of the above characteristics, in a given organic medium, the polymers have the ability to fold upon themselves thereby forming particles which are substantially spherical in shape, with the deployed side chains on the circumference of said particles, stabilizing the particles. Said particles resulting from the graft polymer characteristics do not agglomerate in said medium and thus self-stabilize and form a dispersion of particles of polymer which is particularly stable.

In particular, the graft ethylenic polymers of the dispersion may form nanometric particles with a mean size of 10 nm [nanometer] to 400 nm, preferably 20 nm to 200 nm.

Because of this very small size, the particles of graft polymer in dispersion are particularly stable and thus less likely to form agglomerates.

The graft polymer dispersion may thus be a stable dispersion and not form sediments when placed for a prolonged period (for example 24 hours) at ambient temperature (25° C.)

In particular, the dispersion of graft polymer particles has a dry matter content (dry extract) of polymer which may be from 40% to 70% by weight of dry matter, especially 45% to 65% by weight.

c) Production Method

The graft polymer particle dispersion may be prepared by a method comprising a radical copolymerization step, in an organic polymerization medium, of one or more acrylic monomers as defined above with one or more macromonomers as defined above.

As indicated above, the liquid organic dispersion medium may be identical to or different from the polymerization medium.

In conventional manner, copolymerization is carried out in the presence of a polymerization initiator. The polymerization initiators may be radical initiators. In general, such a polymerization initiator may be selected from organic peroxide compounds such as dilauroyl peroxide, dibenzoyl peroxide, tert-butyl 2-peroxyethylhexanoate; and from diazo compounds such as azobisisobutyronitrile or azobisdimethylvaleronitrile.

The reaction may also be initiated using photoinitiators or radiation such as UV, neutrons or a plasma.

In general, to carry out said method, at least part of the organic polymerization medium, part of the acrylic monomers and/or additional vinyl monomers which, after polymerization, constitute the insoluble backbone, all of the macromonomer (which constitutes the side chains of the polymer) and a portion of the polymerization initiator are introduced into a reactor of suitable size for the quantity of polymer to be produced. At this stage of the introduction, the reaction medium forms a relatively homogeneous medium.

The reaction medium is then stirred and heated to a temperature to obtain polymerization of the monomers and macromonomers. After a certain period, the initially homogeneous and clear medium takes on a milky appearance. A mixture constituted by the remaining portion of the monomers and the polymerization initiator is then added. After a suitable period during which the mixture is heated with stirring, the medium stabilizes into the form of a milky dispersion, the dispersion comprising polymer particles stabilized in the medium in which they were created, said stabilization being due to the presence, in the polymer, of side chains which are soluble in said dispersion medium.

The graft polymer may be present in the composition of the invention in a dry matter content (active substance) of 1% to 70% by weight relative to the total composition weight, preferably 5% to 60%, more preferably 6% to 45% and still more preferably 8% to 40% by weight.

In one implementation, the film-forming polymer is an organic film-forming polymer which is soluble in the liquid oily phase of the composition, especially in the oil or oils of the composition.

In this case, we speak of a liposoluble polymer. The liposoluble polymer may be of any chemical type and may in particular be selected from:

a) Liposoluble and amorphous homopolymers and copolymers of olefins, cycloolefins, butadiene, isoprene, styrene, ethers, esters or vinyl amides, ester or amides of (meth) acrylate acid containing a linear, branched or cyclic $C_4$-$C_{50}$ alkyl group, in particular amorphous. Preferred liposoluble homopolymers and copolymers are obtained from monomers selected from the group constituted by isooctyl(meth)acrylate, isononyl(meth)acrylate, 2-ethylhexyl(meth)acrylate, lauryl(meth)acrylate, isopentyl(meth)acrylate, n-butyl (meth)acrylate, isobutyl(meth)acrylate, methyl(meth) acrylate, tertio-butyl(meth)acrylate, tridecyl(meth)acrylate, stearyl(meth)acrylate, or mixtures thereof. Examples that may be mentioned are the alkyl acrylate/cycloalkyl acrylate copolymer sold by PHOENIX CHEM. under the trade name GIOVAREZ AC-5099 mL, and vinylpyrrolidone copolymers such as copolymers of a $C_2$ to $C_{30}$ alkene, such as $C_3$ to $C_{22}$, and associations thereof. Examples of VP copolymers which may be used in the invention that may be mentioned are VP/vinyl laurate copolymer, VP/vinyl stearate copolymer, butylated polyvinylpyrrolidone (PVP), VP/hexadecene, VP/triacontene or VP/acrylic acid/lauryl methacrylate.

Particular liposoluble copolymers that may be mentioned are:

i) silicone graft acrylic polymers having a silicone backbone, and acrylic grafts or an acrylic backbone and silicone grafts, such as the product sold under the trade name SA 70.5 by 3M and described in U.S. Pat. No. 5,725,882, U.S. Pat. No. 5,209,924, U.S. Pat. No. 4,972,037, U.S. Pat. No. 4,981,903, U.S. Pat. No. 4,981,902, U.S. Pat. No. 5,468,477, and in U.S. Pat. No. 5,219,560 and EP 0 388 582;

ii) liposoluble polymers carrying fluorinated groups belonging to one of the categories described in the text above, in particular FOMBLIN and those described U.S. Pat. No. 5,948,393 and copolymers of alkyl(meth)acrylate/ perfluoroalkyl (meth)acrylate described in EP 0 815 836 and U.S. Pat. No. 5,849,318;

iii) polymers or copolymers resulting from polymerization or copolymerization of an ethylenic monomer comprising one or more ethylenic bonds, preferably conjugated (or dienes). Polymers or copolymers resulting from polymerization or copolymerization of an ethylenic monomer which may be used include vinyl, acrylic and methacrylic copolymers.

In one implementation, the film-forming polymer is a block copolymer comprising at least one block constituted by styrene moieties or styrene derivatives (for example methylstyrene, chlorostyrene or chloromethylstyrene). The copolymer comprising at least one styrene block may be a two- or three-block copolymer, or even a multi-block copolymer, or a star or radial copolymer. The copolymer comprising at least one styrene block may further comprise, for example, an alkyl styrene block (AS), an ethylene/butylene block (EB), an ethylene/propylene block (EP), a butadiene block (B), an isoprene block (I), an acrylate block (A), a methacrylate block (MA) or an association of these blocks. The copolymer comprising at least one block constituted by styrene moieties or styrene derivatives may be a two- or three-block copolymer, in particular of the polystyrene/ polyisoprene or polystyrene/poly butadiene type, such as those sold or manufactured under the trade name "LUVITOL HSB" by BASF and those of the polystyrene/copoly (ethylene-propylene) type or, alternatively, of the polystyrene/copoly(ethylene/butylene) type, such as those sold or manufactured under the trade name "KRATON" by SHELL CHEMICAL CO. or GELLED PERMETHYL 99A by PENRECO, may be used.

The following may, for example, be mentioned: KRATON G1650 (SEES), KRATON G1651 (SEBS), KRATON G1652 (SEBS), KRATON G1657X (SEBS), KRATON G1701X (SEP), KRATON G1702X (SEP), KRATON G1726X (SEB), KRATON D-1101 (SBS), KRATON D-1102 (SBS), KRATON D-1107 (SIS), GELLED PERMETHYL 99A-750, GELLED PERMETHYL 99A-753-58 (mixture of star block copolymer and three-block polymer), GELLED PERMETHYL 99A-753-59 (mixture of star block copolymer and three-block polymer), VERSAGEL 5970 and VERSAGEL 5960 from PENRECO (mixture of star block copolymer and three-block polymer in isododecane).

Styrene-methacrylate copolymers may also be used, such as polymers sold under the trade name OS 129880, OS 129881 and OS 84383 from LUBRIZOL (styrene-methacrylate copolymer).

In one implementation, the film-forming polymer is selected from copolymers of a vinyl ester (the vinyl group being directly bonded to the oxygen atom of the ester group and the vinyl ester having a saturated, linear or branched hydrocarbon radical containing 1 to 19 carbon atoms, bonded to the carbonyl of the ester group) and at least one other monomer which may be a vinyl ester (different from the vinyl ester already present), an α-olefin (containing 8 to 28 carbon atoms), an alkyl vinyl ether (the alkyl group of which contains 2 to 18 carbon atoms), or an allyl or methallyl ester (having a saturated, linear or branched hydrocarbon radical containing 1 to 19 carbon atoms bonded to the carbonyl of the ester group).

Said copolymers may be partially cross-linked using cross-linking agents which may be either vinyl in type or allyl or methallyl in type, such as tetra-allylocyethane, divinylbenzene, divinyloctanedioate, divinyldodecanedioate and divinyloctadecanedioate.

Examples of said copolymers that may be mentioned are as follows: vinyl acetate/allyl stearate, vinyl acetate/vinyl laurate, vinyl acetate/vinyl stearate, vinyl acetate/octadecene, vinyl acetate/octadecylvinylether, vinyl propionate/allyl laurate, vinyl propionate/vinyl laurate, vinyl stearate/octadecene-1, vinyl acetate/dodecene-1, vinyl stearate/ethylvinylther, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate cross-linked with 0.2% of divinyl benzene, vinyl dimethyl propionate/vinyl laurate cross-linked with 0.2% of divinyl benzene, vinyl acetate/octadecyl vinyl ether cross-linked with 0.2% of tetraallyloxyethane, vinyl acetate/allyl stearate, cross-linked with 0.2% of divinyl benzene, vinyl acetate/octadecene-1 cross-linked with 0.2% of divinyl benzene and allyl propionate/allyl stearate cross-linked with 0.2% of divinyl benzene.

Further liposoluble film-forming polymers that may be mentioned are liposoluble copolymers, in particular those resulting from copolymerizing vinyl esters containing 9 to 22 carbon atoms or alkyl acrylates or methacrylates, the alkyl radicals containing 10 to 20 carbon atoms.

Said liposoluble copolymers may be selected from copolymers of vinyl polysuccinate, vinyl polystearate cross-linked with divinyl benzene, diallyl ether or diallyl phthalate, copolymers of stearyl poly(meth)acrylate, vinyl polylaurate, lauryl poly(meth)acrylate, said poly(meth)acrylates possibly being cross-linked using ethylene glycol dimethacrylate or tetraethylene glycol.

The liposoluble copolymers defined above are known and have been described in FR-A-2 232 303; they may have a mass average molecular mass of 2000 to 500000, in particular 4000 to 200000.

Examples of liposoluble polymers which may be used in the context of the invention and that may be mentioned are polyalkylenes, copolymers of $C_2$-$C_{20}$ alkenes, in particular polybutene.

Examples of liposoluble polymers which may be used in the context of the invention that may be mentioned are poly alkylenes, copolymers of $C_2$-$C_{20}$ alkenes, in particular polybutene.

b) Amorphous and liposoluble polycondensates, in particular containing no hydrogen interaction donor groups, in particular aliphatic polyesters containing $C_4$-$C_{50}$ alkyl side chains or polyesters resulting from the condensation of fatty acid dimers, or even polyesters comprising a silicone segment in the form of a sequence, graft or terminal group, as defined in patent FR 0 113 920; and c) Amorphous and liposoluble polysaccharides comprising alkyl side chains (ether or ester), in particular alkyl celluloses containing a saturated or unsaturated, linear or branched $C_1$ to $C_8$ alkyl radical such as ethyl cellulose or propyl cellulose.

The film-forming polymer may in particular be selected from cellulose polymers such as nitro cellulose, cellulose acetate, cellulose acetobutyrate, cellulose acetopropionate, ethyl cellulose, or from polyurethanes, acrylic polymers, vinyl polymers, polyvinylbutyrals, alkyd resins, resins derived from the condensation products of aldehydes such as arylsulfonamide formaldehyde resins, such as the toluene sulfonamide formaldehyde resin, and aryl-sulfonamide epoxy resins.

The film-forming polymer used may in particular be nitrocellulose RS ⅛ sec; RS¼ sec.; ½ sec.; RS 5 sec.; RS 15 sec.; RS 35 sec.; RS 75 sec.; RS 150 sec; AS ¼ sec.; AS ½ sec.; SS ¼ sec.; SS 5 sec.; SS 5 sec., especially those sold by HERCULES; "KETJENTFLEX MS80" toluene sulfonamide formaldehyde resin from AKZO or "SANTOLITE MHP", "SANTOLITE MS 80" from FACONNIER or "RESIMPOL 80" from PAN AMERICANA, the alkyd resin "BECKOSOL ODE 230-70-E" from DAINIPPON, the acrylic resin "ACRYLOID B66", from ROHM & HAAS, and the polyurethane resin "TRIXENE PR 4127" from BAXENDEN.

d) Silicone resins, generally soluble or swellable in silicone oils. These resins are cross-linked polyorganosiloxane polymers.

The term "resin" means a three-dimensional structure.

In one implementation, the silicone resin is selected from silsesquioxanes and siloxysilicates.

In one implementation, the silicone resin is selected from siloxysilicates such as trimethylsiloxysilicates represented by the following formula:

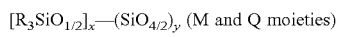

$[R_3SiO_{1/2}]_x$—$(SiO_{4/2})_y$ (M and Q moieties)

in which x and y may have values of 50 to 80, and R represents an alkyl, such as a methyl or an alkyl with two or more carbon atoms.

The ratio of moieties M to moieties Q may, for example, be about 0.7:1. The film-forming silicone resin may, for example, be selected from WACKER 803 and 804 resins available from WACKER SILICONE CORPORATION, and G.E. 1 170-002, available from GENERAL ELECTRIC.

In a further implementation, the silicone resin is selected from silsesquioxanes comprising T moieties:

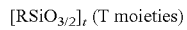 (T moieties)

in which t has a value which may be up to several thousand and R represents an alkyl, such as a methyl or an alkyl with two or more carbon atoms. In one implementation, the silsesquioxane is selected from polymethyl silsesquioxanes which are silsesquioxanes in which R is a methyl group.

The polymethyl silsesquioxanes may, for example, comprise less than about 500 T moieties, preferably from about 50 to about 500 T moieties.

Not all polymethylsilsesquioxanes are film-forming. As an example, polymethylsilsesquioxanes such as TOSPEARL™ from TOSHIBA or KMP590 from SHIN-ETSU are highly insoluble in oils and thus are ineffective film-forming agents. The molecular mass of those polymethylsilsesquioxanes is difficult to determine as they generally contain a thousand or more T moieties.

One example of a polymethylsilsesquioxane which may be used in the invention is BELSIL PMS MK (also known as MK resin), available from WACKER CHEMIE. The polymethylsilsesquioxane is a polymer principally constituted by $CH_3SiO_{3/2}$ (T moieties) repeat moieties and may also contain up to about 1% (by weight or in moles) of $(CH_3)_2SiO_{2/2}$ (D moieties).

Suitable polymethylsilsesquioxanes for use in the present invention include KR-220L available from SHIN-ETSU. The structure of KR-220L is essentially constituted by T silicone moieties ($CH_3SiO_{3/2}$) with terminal Si—OH or silanol moieties; both are available from SHIN-ETSU.

The polymethylsilsesquioxane KR-242A has a structure having about 98% T methyl moieties and about 2% dimethyl D moieties, with Si—OH or silanol terminal moieties, and KR-251, which has a structure having about 88% T methyl moieties and about 12% dimethyl D moieties, with SiOH or silanol terminal moieties; both are available from SHIN-ETSU.

In one implementation of the invention, the silicone resin is soluble or dispersible in silicone oils or volatile organic liquids. In one implementation, the silicone resin is solid at 25° C.

In one implementation, the silicone resin may have a molecular mass of 1000 grams/mole to 10000 grams/mol. In another implementation, the resin is present in the composition in a quantity of 0.5% to 20% by weight relative to the total composition weight, preferably in a quantity of 1% to 10%.

In one implementation of the invention, the silicone resin is selected from combinations of M, D, T and Q moieties containing at least two moieties selected from M, D, T and Q satisfying the relationship $R_nSiO_{(4-n)}$, in which n has a value of 1.0 to 1.50. Certain resins of that type are described in U.S. Pat. No. 6,074,654.

In a further implementation, the film-forming silicone resin is a copolymer in which at least one moiety of the copolymer is selected from the silicone moieties M, D, T and Q, and in which at least one additional moiety of the copolymer is selected from esters. The film-forming silicone resin may, for example, be selected from diisostearoyltrimethylolpropane siloxysilicates such as SF 1 318 available from GE SILICONES.

e) Polyamide-silicone copolymers of the polyorganosiloxane type, such as those described in documents U.S. Pat. No. 5,874,069, U.S. Pat. No. 5,919,441, U.S. Pat. No. 6,051,216 and U.S. Pat. No. 5,981,680.

In accordance with the invention, said silicone polymers may belong to the following two categories:

1) polyorganosiloxanes comprising at least two groups capable of establishing hydrogen interactions, said two groups being located in the chain of the polymer; and/or 2) polyorganosiloxanes comprising at least two groups capable of establishing hydrogen interactions, said two groups being located on the grafts or branches.

The polymers comprising two groups capable of establishing hydrogen interactions in the chain of the polymer may be polymers comprising at least one moiety having formula (XXII):

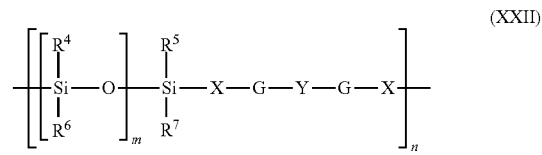 (XXII)

in which:

1) $R^4$, $R^5$, $R^6$ and $R^7$, which may be identical or different, represent a group selected from:

linear, branched or cyclic, saturated or unsaturated $C_1$ to $C_{40}$ hydrocarbon groups which may contain one or more atoms of oxygen, sulfur and/or nitrogen in their chain, and which may be partially or completely substituted with fluorine atoms;

$C_6$ to $C_{10}$ aryl groups, optionally substituted with one or more $C_1$ to $C_4$ alkyl groups;

polyorganosiloxane chains containing or not containing one or more oxygen, sulfur and/or nitrogen atoms;

2) the Xs, which may be identical or different, represent a linear or branched $C_1$ to $C_H$ alkylene diyl group which may contain one or more oxygen and/or nitrogen atoms in its chain;

3) Y is a saturated or unsaturated $C_1$-$C_{50}$ divalent linear or branched alkylene, arylene, cycloalkylene, alkylarylene group, which may comprise one or more oxygen, sulfur and/or nitrogen atoms and/or carry one of the following atoms or groups of atoms as a substituent: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl or $C_1$ to $C_6$ aminoalkyl; or 4) Y represents a group with formula (XXIII):

 (XXIII)

in which:

T represents a trivalent or tetravalent, linear or branched, saturated or unsaturated $C_3$ to $C_{24}$ hydrocarbon group optionally substituted with a polyorganosiloxane chain, and which may contain one or more atoms selected from O, N and S, or T represents a trivalent atom selected from N, P and Al; and $R^8$ represents a linear or branched $C_1$ to $C_{50}$ alkyl group or a polyorganosiloxane chain which may comprise one or more ester, amide, urethane, thiocarbamate, urea, thiourea and/or sulfonamide groups which may optionally be bonded to another chain of the polymer 5) the Gs, which may be identical or different, represent divalent groups selected from:

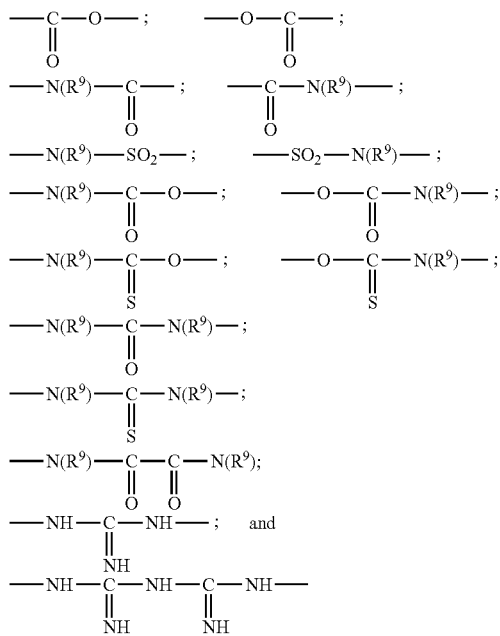

where $R^9$ represents a hydrogen atom or a linear or branched $C_1$ to $C_{20}$ alkyl group, provided that at least 50% of the radicals $R^9$ of the polymer represents a hydrogen atom and at least two of the G groups of the polymer are a group other than:

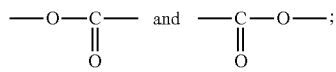

6) n is a whole number from 2 to 500, in particular 2 to 200, and m is a whole number from 1 to 1000, in particular 1 to 700 and more preferably 6 to 200.

In accordance with the invention, 80% of the $R^4$, $R^5$, $R^6$ and $R^7$ groups of the polymer are preferably selected from methyl, ethyl, phenyl and 3,3,3-trifluoropropyl groups.

In accordance with the invention, Y may represent various divalent groups, optionally further comprising one or more free valencies in order to establish bonds with other moieties of the polymer or copolymer. In particular, Y represents a group selected from:

a) linear $C_1$ to $C_{20}$ alkylene groups, preferably $C_1$ to $C_{10}$;

b) branched $C_{30}$ to $C_{56}$ alkylene groups which may include cycles and non conjugated unsaturated bonds;

c) $C_5$-$C_6$ cycloalkylene groups;

d) phenylene groups, optionally substituted with one or more $C_1$ to $C_{40}$ alkyl groups;

e) $C_1$ to $C_{20}$ alkylene groups comprising 1 to 5 amide groups;

f) $C_1$ to $C_{20}$ alkylene groups comprising one or more substituents selected from hydroxyl, $C_3$ to $C_8$ cycloalkane groups, $C_1$ to $C_3$ hydroxyalkyl and C1 to C6 alkylamines;

g) Polyorganosiloxane chains with formula (XXIV):

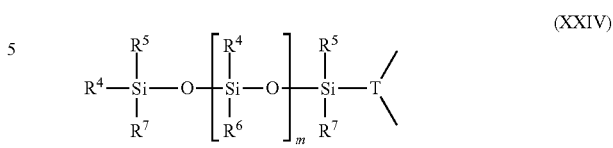

in which $R^4$, $R^5$, $R^6$, $R^7$, T and m are as defined above; and h) polyorganosiloxane chains with formula (XXV):

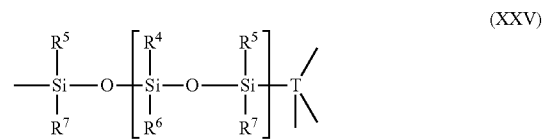

The polyorganosiloxanes of the second category may be polymers comprising at least one moiety having formula (XXVI):

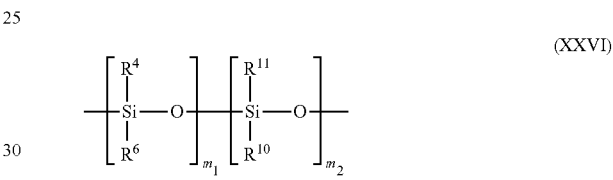

in which:

$R^4$ and $R^6$, which may be identical or different, are as defined above for formula (XXII);

$R^{10}$ represents a group as defined above for $R^4$ and $R^6$, or represents the group with formula —X-G-$R^{12}$ in which X and G are as defined above for formula (XXII) and $R^{12}$ represents a hydrogen atom or a linear, branched or cyclic, saturated or unsaturated $C_1$ to $C_{50}$ hydrocarbon group optionally comprising one or more atoms selected from O, S and N in its chain, optionally substituted with one or more fluorine atoms and/or one or more hydroxyl groups, or a phenyl group optionally substituted with one or more $C_1$ to $C_4$ alkyl groups;

$R^{11}$ represents the group with formula —X-G-$R^9$ in which X, G and $R^{12}$ are as defined above;

$m_1$ is a whole number from 1 to 998; and $m_2$ is a whole number from 2 to 500.

According to the invention, the polymer used may be a homopolymer, i.e. a polymer comprising several identical moieties, in particular moieties with formula (XXII) or formula (XXVI).

According to the invention, it is also possible to use a polymer constituted by a copolymer comprising several different moieties with formula (XXII), i.e. a polymer in which at least one of $R^4$, $R^5$, $R^6$, $R^7$, X, G, Y, m and n is different in one of the moieties. The copolymer may also be formed by several moieties with formula (XXVI) in which at least one of $R^4$, $R^6$, $R^{10}$, $R^{11}$, $m_1$ and $m_2$ is different in at least one of the moieties.

It is also possible to use a copolymer comprising at least one moiety with formula (XXII) and at least one moiety with formula (XXVI), the moieties with formula (XXII) and moieties with formula (XXVI) possibly being identical or different from each other.

In a variation, it is also possible to use a copolymer comprising, in addition, at least one hydrocarbon moiety comprising two groups capable of establishing hydrogen bonds, selected from ester, amide, sulfonamide, carbamate, thiocarbamate, urea, urethane, thiourea, oxamido, guanidine and biguanidino groups and combinations thereof.

Said copolymers may be block copolymers, sequenced copolymers or graft copolymers.

f) Linear Ethylenic Sequenced Polymers

The composition of the invention may contain, as a film-forming agent, a linear sequenced ethylenic polymer below termed a "sequenced polymer" with a particular structure that is described below.

The term "sequenced" polymer means a polymer comprising at least 2 distinct sequences, preferably at least 3 distinct sequences.

The polymer is a polymer with a linear structure. In contrast, an example of a non-linear structured polymer is a polymer with a branched, star, graft or other structure.

Advantageously, the sequenced polymer is free of styrene. The term "polymer free of styrene" means a polymer containing less than 10% by weight, relative to the total polymer weight, preferably less than 5% by weight, more preferably less than 2% by weight and still more preferably less than 1% by weight or contains no styrene-like monomer such as styrene, styrene derivatives such as methylstyrene, chlorostyrene or chloromethylstyrene.

In particular, the sequenced polymer comprises at least one first sequence and at least one second sequence having different glass transition temperatures (Tg), said first and second sequences being connected together by an intermediate sequence comprising at least one constituent monomer of the first sequence and at least one constituent monomer of the second sequence.

The term "at least" one sequence means one or more sequences.

The intermediate sequence is a sequence comprising at least one constituent monomer of the first sequence and at least one constituent monomer of the second sequence of the polymer in order to "compatibilize" these sequences.

More precisely, in the above and below, the terms "first" and "second" sequences do not in any way dictate the order of said sequences (or blocks) in the structure of the sequenced polymer.

Advantageously, the first and second sequences and the sequenced polymer are incompatible with each other.

The term "sequences which are incompatible with each other" means that the mixture formed by the polymer corresponding to the first sequence and the polymer corresponding to the second sequence is not miscible in the organic liquid which is in the mass majority of the liquid oily phase at ambient temperature (25° C.) and at atmospheric pressure ($10^5$ Pa [Pascal]), for an amount of the polymer mixture of 5% by weight or more relative to the total weight of the mixture (polymers and solvent), it being understood that:

i) said polymers are present in the mixture in an amount such that the respective weight ratio is from 10/90 to 90/10; and ii) each of the polymers corresponding to the first and second sequences has a (mass or number) average molecular mass equal to that of the sequenced polymer +−15%.

When the composition comprises a liquid oily phase comprising a mixture of organic liquids, assuming that two or more organic liquids are present in identical proportions by weight, said mixture of polymers is not miscible in at least one of them.

Clearly, when the liquid oily phase comprises a single organic liquid, the organic liquid is the major organic liquid.

In particular, the sequenced polymer does not include silicon atoms in its backbone. The term "backbone" means the principal chain of the polymer, in contrast to the pendant side chains.

In particular, the sequenced polymer is not soluble in water or in a mixture of water and linear or branched lower mono-alcohols containing 2 to 5 carbon atoms such as ethanol, isopropanol or n-propanol, without modifying the pH, at an active material content of at least 1% by weight, at ambient temperature (25° C.).

In particular, the sequenced polymer is not an elastomer.

The term "non-elastomeric polymer" means a polymer which, when it is subjected to a force intended to extend it (for example by 30% relative to its initial length), does not return to a length substantially identical to its initial length when the force ceases.

More specifically, the term "non-elastomeric polymer" means a polymer with an instantaneous recovery, $R_i$, of <50% and a delayed recovery, $R_{2h}$, of <70% after undergoing an extension of 30%. Preferably, $R_i$ is <30% and $R_{2h}$ is <50%.

i) Recovery Test

More precisely, the non-elastomeric character of the polymer is determined using the following protocol:

A film of polymer is prepared by pouring a solution of polymer into a Teflon lined matrix then drying for 7 days under a controlled atmosphere at 23±5° C. and 50±10% relative humidity.

A film about 100 μm [micrometer] thick is obtained from which rectangular specimens are cut (for example using a punch) with a width of 15 mm [millimeter] and a length of 80 mm.

A tension is applied to said specimen using a Zwick apparatus, applying the temperature and humidity conditions used for drying.

The specimens are drawn at a rate of 50 mm/min and the distance between the jaws is 50 mm, corresponding to the initial length (I0) of the specimen.

The instantaneous recovery $R_i$ is determined as follows:

the specimen is extended by 30% $\epsilon_{max}$), i.e. about 0.3 times its initial length ($I_0$);

the force is relaxed, imposing a return rate equal to the draw rate, i.e. 50 mm/min, and the residual extension of the sample is measured as a percentage after returning to the zero stress ($\epsilon_1$).

The instantaneous recovery, as a % ($R_i$), is given by the following formula:

$$R_i = (\epsilon_{max} - \epsilon_1)/\epsilon_{max} * 100$$

To determine the delayed recovery, the residual lengthening of the specimen is measured as a percentage ($\epsilon_{2h}$), 2 hours after returning to zero stress.

The delayed recovery, as a % ($R_{2h}$), is given by the following formula:

$$R_{2h} = (\epsilon_{max} - \epsilon_{2h})/\epsilon_{max} * 100$$

Purely by way of indication, a polymer in one implementation of the invention has an instantaneous recovery $R_i$ of 10% and a delayed recovery $R_{2h}$ of 30%.

Advantageously, the sequenced polymer has a polydispersity I of more than 2, for example 2 to 9, in particular 2.5 or more, for example from 2.5 to 8, and more particularly 2.8 or more, especially 2.8 to 6.

The polydispersity index I of the sequenced polymer is equal to the ratio of the mass average molecular mass Mw to the number average molecular mass Mn.

The mass average molecular mass (Mw) and number average molecular mass (Mn) are determined by gel permeation liquid chromatography (THF solvent, calibration curve established with linear polystyrene specimens, refractometric detector).

The mass average molecular weight (Mw) of the sequenced polymer is in particular 300000 or less, for example 35000 to 200000, more particularly 45000 to 150000.

The mass average molecular mass (Mn) of the sequenced polymer is, in particular, 70000 or less, for example 10000 to 60000, more particularly 12000 to 50000.

Each sequence or block of the sequenced polymer is derived from a type of monomer or several different types of monomers.

This means that each sequence may be constituted by a homopolymer or a copolymer; said copolymer constituting the sequence which may in turn be random or alternating.

Advantageously, the intermediate sequence comprising at least one constituent monomer of the first sequence and at least one constituent monomer of the second sequence of the sequenced polymer is a random polymer.

In particular, the intermediate sequence is essentially derived from the constituent monomers of the first sequence and the second sequence.

The term "essentially" means at least 85%, in particular at least 90%, more particularly 95% and more particularly 100%.

Advantageously, the intermediate sequence has a glass transition temperature Tg in the range between the glass transition temperatures of the first and second sequences.

The glass transition temperatures indicated for the first and second sequences may be the theoretical Tgs determined from the theoretical Tgs of the constituents monomers of each of the sequences, which can be found in $3^{rd}$ a reference manual such as the Polymer Handbook, edition, John Wiley, using the following relationship known as Fox's Law:

$$1/Tg = \sum_i (\acute{\omega}_i/Tg_i)$$

$\acute{\omega}_i$ being the mass fraction of monomer i in the sequence under consideration and $Tg_i$ being the glass transition temperature of the homopolymer of monomer i.

Unless otherwise indicated, the Tgs indicated for the first and second sequences in the present application are theoretical Tgs.

The difference between the glass transition temperatures of the first and second sequences is generally more than 10° C., in particular more than 20° C., and more particularly more than 30° C.

ii) Polymer Sequences

In particular, the first sequence of the sequenced polymer may be selected from:
a) a sequence having a Tg of 40° C. or more;
b) a sequence having a Tg of 20° C. or less;
c) a sequence having a Tg between 20° C. and 40° C.; and the second sequence is selected from a category a), b) or c) which is different from that of the first sequence.

The term "between . . . and . . . " as used in the present invention means a range of values from which the limits mentioned are excluded, and " . . . to . . . " and "from . . . to . . . " means a range of values the limits of which are included.

a) Sequence Having a Tg of 40° C. or More

The sequence with a Tg of 40° C. or more has, for example, a Tg of 40° C. to 150° C., in particular 50° C. or more, for example from 50° C. to 120° C., in particular 60° C. or more, for example from 60° C. to 120° C.

The sequence with a Tg of 40° C. or more may be a homopolymer or a copolymer.

When said sequence is a homopolymer, it is derived from monomers that are such that the homopolymers prepared from said monomers have glass transition temperatures or 40° C. or more. This first sequence may be a homopolymer constituted by a single type of monomer (where the Tg of the corresponding homopolymer is 40° C. or more).

When the first sequence is a copolymer, it may be completely or partially derived from one or more monomers, the nature of which and the concentration of which are selected so that the Tg of the resulting copolymer is 40° C. or more. As an example, the copolymer may comprise:

monomers that are such that homopolymers prepared from said monomers have a Tg of 40° C. or more, for example a Tg of 40° C. to 150° C., in particular 50° C. or more, for example from 50° C. to 120° C., in particular 60° C. or more, for example from 60° C. to 120° C.; and monomers that are such that homopolymers prepared from said monomers have a Tg of 40° C. or less, selected from monomers having a Tg between 20° C. and 40° C. and/or monomers having a Tg of 20° C. or less, for example a Tg of –100° C. to 20° C., in particular less than 15° C., especially from –80° C. to 15° C. and in particular less than 10° C., for example –50° C. to 0° C. as described below.

Monomers the homopolymers of which have a glass transition temperature of 40° C. or more are preferably selected from the following monomers, also termed principal monomers:

methacrylates with formula (XII):

$$CH_2—C(CH_3)—COOR_1 \qquad (XII)$$

in which $R_1$ represents an unsubstituted linear or branched alkyl group containing 1 to 4 carbon atoms, such as a methyl, ethyl, propyl or isobutyl group or $R_1$ represents a $C_4$ to $C_{12}$ cycloalkyl group;

acrylates with formula (XIII):

$$CH_2—CH—COOR_2 \qquad (XIII)$$

in which $R_2$ represents a $C_8$ to $C_{12}$ cycloalkyl group such as isobornyl acrylate or a tertiobutyl group;

(meth)acrylamides with formula (XIV):

(XIV)

where:

$R_7$ and $R_8$, which may be identical or different, each represent a hydrogen atom or a linear or branched $C_1$ to $C_{12}$ alkyl group such as a n-butyl, t-butyl, isopropyl, isohexyl, isooctyl, or isononyl group; or $R_7$ represents H and $R_8$ represents a 1,1-dimethyl-3-oxobutyl group; and R' designates H or methyl; and mixtures thereof.

Examples of monomers that may be mentioned are N-butylacrylamide, N-t-butylacrylamide, N-isopropylacrylamide, N,N-dimethylacrylamide and N,N-dibutylacrylamide.

Particularly advantageous principal monomers are methyl methacrylate, isobutyl(meth)acrylate, isobornyl(meth)acrylate and mixtures thereof.

b) Sequence Having a Tg of 20° C. or Less

The sequence having a Tg of 20° C. or less has, for example, a Tg of −100° C. to 20° C., preferably 15° C. or less, especially from −80° C. to 15° C. and more preferably 10° C. or less, for example from −50° C. to 0° C.

The sequence with a Tg of 20° C. or less may be a homopolymer or a copolymer.

When said sequence is a homopolymer, it is derived from monomers, which are such that homopolymers prepared from said monomers have glass transition temperatures of 20° C. or less. Said second sequence may be a homopolymer constituted by a single type of monomer (wherein the Tg of the corresponding homopolymer is 20° C. or less).

When the sequence with a Tg of 20° C. or less is a copolymer, it may be wholly or partially derived from one or more monomers, the nature and concentration of which are selected so that the Tg of the resulting copolymer is 20° C. or less.

As an example, it may comprise:
one or more monomers wherein the corresponding homopolymer has a Tg of 20° C. or less, for example a Tg of −100° C. to 200° C., in particular less than 15° C., especially −80° C. to 15° C. and in particular less than 10° C., for example from −50° C. to 0° C.; and
one or more monomers wherein the corresponding homopolymer has a Tg of more than 20° C., such as monomers having a Tg of 40° C. or more, for example a Tg of 40° C. to 150° C., in particular 50° C. or more, for example from 50° C. to 120° C., and in particular 60° C. or more, for example from 60° C. to 120° C. and/or monomers having a Tg between 20° C. and 40° C., as described above.

In particular, the sequence with a Tg of 20° C. or less is a homopolymer.

Monomers the homopolymer of which has a Tg of 20° C. or less are preferably selected from the following monomers or principal monomers:

acrylates with formula (XV):

$CH_2$—$CHCOOR_3$ (XV)

$R_3$ representing an unsubstituted linear or branched $C_1$ to $C_{12}$ alkyl group in which one or more heteroatoms selected from O, N and S are interposed;

methacrylates with formula (XVI):

$CH_2$—$C(CH_3)$—$COOR_4$ (XVI)

$R_4$ represents an unsubstituted linear or branched alkyl $C_6$ to $C_{12}$ group in which one or more heteroatoms selected from O, N and S are optionally interposed;

vinyl esters with formula (XVII):

$R_5$—CO—O—CH—$CH_2$ (XVII)

where $R_5$ represents a linear or branched $C_4$ to $C_{12}$ alkyl group;

ethers of vinyl alcohol and $C_4$ to $C_{12}$ alcohol;

$C_4$ to $C_{12}$ alkyl N-alkylated acrylamides, such as N-octylacrylamide; and mixtures thereof.

Particularly preferred principal monomers for the sequence with a Tg of 20° C. or less are alkyl acrylates the alkyl chain of which contains 1 to 10 carbon atoms, such as methyl acrylate, isobutyl acrylate, 2-ethylhexyl acrylate and mixtures thereof.

c) Sequence Having a Tg Between 20° C. and 40° C.

The sequence with a Tg between 20° C. and 40° C. may be a homopolymer or a copolymer.

When said sequence is a homopolymer, it is derived from monomers (or principal monomers) which are such that homopolymers prepared from said monomers have glass transition temperatures between 20° C. and 40° C. Said first sequence may be a homopolymer, constituted by a single type of monomer (wherein the Tg of the corresponding homopolymer is from 20° C. to 40° C.).

Monomers with a homopolymer with a glass transition temperature between 20° C. and 40° C. are preferably selected from n-butyl methacrylate, cyclodecyl acrylate, neopentyl acrylate, isodecylacrylamide and mixtures thereof.

Then the sequence with a Tg between 20° C. and 40° C. is a copolymer, it is completely or partially derived from one or more monomers (or a principal monomer) the nature and concentration of which are selected so that the Tg of the resulting copolymer is between 20° C. and 40° C.

Advantageously, the sequence with a Tg between 20° C. and 40° C. is a copolymer wholly or partially derived from:
principal monomers the corresponding homopolymer of which has a Tg of 40° C. or more, for example a Tg of 40° C. to 150° C., in particular 50° C. or more, for example 50° C. to 120° C., and preferably 60° C. or more, for example 60° C. to 120° C., as described above; and/or
principal monomers the corresponding homopolymer of which has a Tg of 20° C. or less, for example a Tg from −100° C. to 20° C., in pa 15° C. or less, especially −80° C. to 15° C. and in particular 10° C. or less, for example −50° C. to 0° C., as described above;

said monomers being selected so that the Tg of the copolymer forming the first sequence is between 20° C. and 40° C.

Said principal monomers are, for example, selected from methyl methacrylate, isobornyl acrylate and methacrylate, butyl acrylate, 2-ethylhexyl acrylate and mixtures thereof.

More particularly, the proportion of the second sequence with a Tg of 20° C. or less is from 10% to 85% by weight of polymer, preferably 20% to 70% and more preferably 20% to 50%.

Each sequence may nevertheless contain a minor proportion of at least one constituent monomer of the other sequence.

Hence, the first sequence may contain at least one constituent monomer of the second sequence, and conversely.

In addition to the monomers indicated above, each of the first and/or second sequences of the sequenced polymer may comprise one or more monomers termed additional monomers, which differ from the principal monomers mentioned above.

The nature and quantity of these additional monomer or monomers are selected so that the sequence in which they are formed has the desired glass transition temperature.

iii) Additional Monomer

This additional monomer is, for example, selected from:
hydrophilic monomers such as:
monomers with an ethylenically unsaturated bond comprising at least one carboxylic or sulfonic acid function, such as:
acrylic acid, methacrylic acid, crotonic acid, maleic anhydride, itaconic acid, fumaric acid, maleic acid, acrylamidopropanesulfonic acid, vinylbenzoic acid, vinylphosphoric acid and salts thereof;

monomers with an ethylenically unsaturated bond comprising at least one tertiary amine function such as:
2-vinylpyridine, 4-vinylpyridine, dimethylaminoethyl methacrylate, diethylaminoethyl methacrylate, dimethylaminopropyl methacrylamide and salts thereof;
methacrylates with formula (XVIII):

$$CH_2\!-\!C(CH_3)\!-\!COOR_6 \qquad\qquad (XVIII)$$

in which $R_6$ represents a linear or branched alkyl group containing 1 to 4 carbon atoms, such as a methyl, ethyl, propyl or isobutyl group, said alkyl group being substituted with one or more substituents selected from hydroxyl groups (such as 2-hydroxypropyl methacrylate, 2-hydroxyethyl methacrylate) and halogen atoms (Cl, Br, I, F), such as trifluoroethyl methacrylate;
methacrylates with formula (XIX):

$$CH_2\!-\!C(CH_3)\!-\!COOR_9 \qquad\qquad (XIX)$$

in which $R_9$ represents a linear or branched $C_6$ to $C_{12}$ alkyl group, in which one or more heteroatoms selected from O, N and S are optionally interposed, said alkyl group being substituted with one or more substituents selected from hydroxyl groups and halogen atoms (Cl, Br, I, F);
acrylates with formula (XX):

$$CH_2\!-\!CHCOOR_{10} \qquad\qquad (XX)$$

in which $R_{10}$ represents a linear or branched $C_1$ to $C_{12}$ alkyl group substituted with one or more substituents selected from hydroxyl groups and halogen atoms (Cl, Br, I and F), such as 2-hydroxypropyl acrylate and 2-hydroxyethyl acrylate, or $R_{10}$ represents a $C_1$ to $C_{12}$—O—POE (polyoxyethylene) with 5 to 30 repetitions of the oxyethylene moiety, for example methoxy-POE, or $R_8$ represents a polyoxyethylene group containing 5 to 30 ethylene oxide moieties;
monomers with an ethylenically unsaturated bond comprising one or more silicon atoms, such as methacryloxypropyl trimethoxy silane, methacryloxypropyl tris(trimethylsiloxy) silane; and
mixtures thereof.

Particularly preferred additional monomers are acrylic acid, methacrylic acid, trifluoroethyl methacrylate and mixtures thereof.

In a particular implementation, the sequenced polymer is a non-silicone polymer, i.e. a polymer free of silicon atoms.

Said additional monomers generally represent a quantity of 30% by weight or less, for example 1% to 30% by weight, preferably 5% to 20% by weight, more preferably 7% to 15% by weight of the total weight of the first and/or second sequences.

In particular, each of the first and second sequences comprises at least one monomer selected from (meth)acrylic acid esters, and optionally at least one monomer selected from (meth)acrylic acid and mixtures thereof.

Advantageously, each of the first and second sequences of the sequenced polymer is wholly derived from at least one monomer selected from acrylic acid, (meth)acrylate acid esters, and possibly at least one monomer selected from (meth)acrylate acid, and mixtures thereof.

iv) Production Method

The sequenced polymer may be obtained by radical polymerization in solution using the following preparation method:
introducing a portion of the polymerization solvent into a suitable reactor heated to a suitable temperature for polymerization (typically 60° C. to 120° C.);
once said temperature has been reached, introducing the constituent monomers of the first sequence in the presence of a portion of the polymerization initiator;
at the end of a time T corresponding to a maximum degree of conversion of 90%, introducing the constituent monomers of the second sequence and the other portion of the initiator;
reacting the mixture for a time T' (from 3 to 6 h), at the end of which the mixture is returned to ambient temperature;
obtaining the polymer in solution in the polymerization solvent.

The term "polymerization solvent" means a solvent or a mixture of solvents. In particular, the polymerization solvent may be selected from ethyl acetate, butyl acetate, alcohols such as isopropanol or ethanol, aliphatic alkanes such as isododecane, and mixtures thereof. In particular, the polymerization solvent is a mixture of butyl acetate and isopropanol or isododecane.

In a particular implementation, the sequenced polymer comprises a first sequence with a Tg of 40° C. as described above in a) and a second sequence with a Tg of 20° C. or less, as described above at b).

In particular, the first sequence with a Tg of 40° C. or more is a copolymer derived from monomers which are such that the homopolymer prepared from said monomers has a glass transition temperature of 40° C. or more, such as the monomers described above.

Advantageously, the second sequence with a Tg of 20° C. or less is a homopolymer derived from monomers which are such that the homopolymer prepared from said monomers has a glass transition temperature of 20° C. or less, such as the monomers described above.

In particular, the proportion of the sequence with a Tg of 40° C. or more is from 20% to 90% by weight of polymer, preferably 30% to 80% and more preferably 50% to 70%.

In particular, the proportion of the sequence with a Tg of 20° C. or less is from 5% to 75% by weight of polymer, preferably 15% to 50%, and more preferably 25% to 45%.

Advantageously, the sequenced polymer may comprise:
a first sequence with a Tg of 40° C. or more, for example 85° C. to 115° C., which is an isobornyl acrylate/isobutyl methacrylate copolymer;
a second sequence with a Tg of 20° C. or less, for example −85° C. to −55° C., which is a 2-ethylhexyl acrylate homopolymer; and
an intermediate sequence which is a random isobornyl acrylate/isobutyl methacrylate/2-ethylhexyl acrylate copolymer.

In a further implementation, the sequenced polymer comprises a first sequence having a glass transition temperature (Tg) between 20° C. and 40° C., as described in c), and a second sequence with a glass transition temperature of 20° C. or less, as described above in b) or a glass transition temperature of 40° C. or more, as described above.

In particular, the proportion of the first sequence with a Tg between 20° C. and 40° C. is from 10% to 85% by weight of polymer, in particular 30% to 80% by weight and more preferably 50% to 70%.

When the second sequence is a sequence having a Tg of 40° C. or more, in particular it is present in a proportion of 10% to 85% by weight of polymer, in particular 20% to 70% and more particularly 30% to 70%.

When the second sequence is a sequence with a Tg of 20° C. or less, in particular it is present in a proportion of 10% to 85% by weight of polymer, in particular 20% to 70% and more particularly 20% to 50%.

In particular, the first sequence with a Tg between 20° C. and 40° C. is a copolymer derived from monomers which are such that the corresponding homopolymer has a Tg of 40° C. or more, and monomers which are such that the corresponding homopolymer has a Tg of 20° C. or less.

Advantageously, the second sequence with a Tg of 20° C. or less or with a Tg of 40° C. or more is a homopolymer.

In a first variation, the sequenced polymer comprises:
a first sequence with a Tg between 20° C. and 40° C., for example with a Tg of 21° C. to 39° C., which is a copolymer comprising isobornyl acrylate/isobutyl methacrylate/2-ethylhexyl acrylate;
a second sequence with a Tg of 20° C. or less, for example −65° C. to −35° C., which is a methyl methacrylate homopolymer; and
an intermediate sequence which is a random isobornyl acrylate/isobutyl methacrylate/2-ethylhexyl acrylate copolymer.

In another variation, the sequenced polymer may comprise:
a first sequence with a Tg of 40° C. or more, for example from 85° C. to 115° C., which is an isobornyl acrylate/isobutyl methacrylate copolymer;
a second sequence with a Tg of 20° C. or less, for example −35° C. to −5° C., which is an isobutyl acrylate homopolymer; and
an intermediate sequence which is a random isobornyl methacrylate/isobutyl methacrylate/isobutyl acrylate random copolymer.

In a still further variation, the sequenced polymer may comprise:
a first sequence with a Tg of 40° C. or more, for example 60° C. to 90° C., which is an isobornyl acrylate/isobutyl methacrylate copolymer;
a second sequence with a Tg of 20° C. or more, for example from −35° C. to −5° C., which is an isobutyl acrylate homopolymer; and
an intermediate sequence which is a random isobornyl acrylate/isobutyl methacrylate/isobutyl acrylate copolymer.

g) Products of reaction between a silica derivative and a polyorganosiloxane carrying terminal silanol groups, such as those described in U.S. Pat. No. 5,162,410, U.S. Pat. No. 0,330,747 and U.S. Pat. No. 5,451,610, the contents of shoulder are hereby incorporated by reference. Products of that type are sold under the trade name Bio-PSA by Dow Corning, for example the product of that range with reference number 7-4405.

In accordance with the invention, the film-forming polymer may be a solid which is insoluble in the oily phase of the composition at ambient temperature, for example about 25° C. The polymer is also insoluble in the oily phase at its softening temperature, in contrast to a wax of polymeric origin which is soluble in the liquid organic phase (or oily phase) at its melting temperature. In this respect, the polymer is not a wax.

1) Polymers

The composition of the invention advantageously comprises at least one stable dispersion of essentially spherical polymer particles of one or more polymers in a physiologically acceptable oily phase.

Said dispersions may in particular be in the form of nano particles of polymers in stable dispersion in said liquid organic phase. The nano particles preferably have a mean size in the range 5 nm to 800 nm, and preferably in the range 50 on to 500 nm. However, it is possible to obtain polymer particle sizes of up to 1 µm.

In particular, the polymer particles in dispersion are insoluble in hydrosoluble alcohols such as ethanol.

The polymers in dispersion which can be used in the composition of the invention preferably have a molecular weight of the order of 2000 to 10000000 g/mol, and a Tg of −100° C. to 300° C., preferably −50° C. to 100° C., more preferably −10° C. to 50° C.

It is possible to use polymers which can form films, preferably with a low Tg equal to or lower than the temperature of skin, and in particular 40° C. or less.

Examples of film-forming polymers that may be mentioned are acrylic or vinyl radical copolymers or homopolymers, preferably with a Tg of 40° C. or less and in particular from −10° C. to 30° C., used alone or as a mixture.

The term "radical type polymer" means a polymer obtained by polymerizing unsaturated monomers, in particular with ethylenically unsaturated bonds, each monomer being capable of self-polymerizing (in contrast to polycondensates). The radical type polymers may in particular be polymers or copolymers, vinyl, in particular acrylic polymers.

The acrylic polymers may result from polymerizing monomers with an ethylenically unsaturated bond containing at least one acid group and/or esters of said acid monomers and/or amides of said acids.

Monomers carrying an acid group which may be used include α,β-ethylenically unsaturated carboxylic acids such as acrylic acid, methacrylic acid, crotonic acid, maleic acid, and itaconic acid. In particular, (meth)acrylic acid, and crotonic acid may be used, more particularly (meth)acrylic acid.

The esters of acid monomers are advantageously selected from esters of (meth)acrylic acid (also known as (meth) acrylates), such as alkyl(meth)acrylates, in particular of $C_1$-$C_{20}$ alkyl, preferably $C_1$-$C_8$, aryl(meth)acrylates, in particular of $C_6$-$C_{10}$ aryl, and hydroxyalkyl(meth)acrylates, in particular $C_2$-$C_6$ hydroxyalkyl. Alkyl(meth)acrylates which may be mentioned include methyl, ethyl, butyl, isobutyl, 2-ethylhexyl, and lauryl methacrylate. Hydroxyalkyl(meth) acrylates which may be mentioned include hydroxyethyl (meth)acrylate, and 2-hydroxypropyl(meth)acrylate. Aryl (meth)acrylates which may be mentioned include benzyl acrylate and phenyl acrylate.

(Meth)acrylic acid esters that are particularly suited to cosmetic compositions of the invention are alkyl(meth) acrylates.

Particular radical polymers which may be used are (meth) acrylate acid and alkyl(meth)acrylate copolymers, in particular $C_1$-$C_4$ alkyl(meth)acrylate. More particularly, methyl acrylates optionally copolymerized with acrylic acid may be used.

Amides of acid monomers which may be mentioned are (meth)acrylamides, especially N-alkyl(meth)acrylamides, in particular $C_2$-$C_{12}$ alkyl(meth)acrylamides such as N-ethyl acrylamide, N-t-butyl acrylamide and N-t-octyl acrylamide; N-dialkyl $C_1$-$C_4$ alkyl(meth)acrylamides.

The acrylic polymers may also result from polymerizing monomers with an ethylenically unsaturated bond containing at least one amine group in free or partially or totally neutralized form, or indeed partially or totally quaternized. By way of example, such monomers may be dimethylaminoethyl(meth)acrylate, dimethylaminoethyl methacrylamide, vinylamine, vinylpyridine, and/or diallyldimethylammonium chloride.

The vinyl polymers may also result from homopolymerizing or copolymerizing at least one monomer selected from vinyl esters and styrene monomers. In particular, said monomers may be polymerized with acid monomers and/or their esters and/or their amides, such as those mentioned above.

Examples of vinyl esters which may be mentioned are vinyl acetate, vinyl propionate, vinyl neodecanoate, vinyl pivalate, vinyl benzoate, and vinyl t-butyl benzoate. An example of a styrene monomer which may be mentioned is alpha-methyl styrene.

The list of monomers given above is not limiting and it is possible to use any monomer which is known to the skilled person which falls into the categories of acrylic and vinyl monomers (including monomers modified by a silicone chain).

As other vinyl monomers that can used, mention can be made of:

N-vinylpyrrolidone, vinylcaprolactam, vinyl N-alkyl($C_1$-$C_6$) pyrroles, vinyl-oxazoles, vinyl-thiazoles, vinylpyrimidines, vinylimidazoles;

olefins such ethylene, propylene, butylenes, isoprene, butadiene.

The vinyl polymer may be cross-linked using one or more di-functional monomers, in particular having at least two ethylenically unsaturated bonds, such as ethylene glycol dimethacrylate or diallyl phthalate.

In non-limiting manner, the polymers in dispersion of the invention may be selected from the following polymers or copolymers: polyurethanes, acrylic polyurethanes, polyureas, polyurea-polyurethanes, polyester-polyurethanes, polyether-polyurethanes, polyesters, polyester amides, alkyds; acrylic and/or vinyl polymers or copolymers; acrylic-silicone copolymers; polyacrylamides; silicone polymers such as polyurethanes or silicone acrylics, fluorinated polymers, and mixtures thereof.

The polymer(s) in dispersion in the oily phase may represent 5% to 40% by weight of the dry matter of the composition, preferably 5% to 35%, better 8% to 30%.

2) Stabilizer

In one implementation, the polymer particles in dispersion are surface stabilized by a stabilizer which is solid at ambient temperature. The dry matter content in the dispersion then represents the total quantity of polymer+stabilizer, given that the quantity of polymer cannot be less than 5%.

In particular, the polymer particles are surface stabilized using a stabilizer which may be a sequenced polymer, a graft polymer and/or a random polymer, used alone or as a mixture. Stabilization may be achieved by any known means, in particular by direct addition of stabilizing polymer during polymerization.

The stabilizer may also be present in the mixture before polymerizing the polymer. However, it is also possible to add it continuously, especially when the monomers are also added continuously.

2-30% by weight of stabilizer relative to the initial mixture of monomers, preferably 5-20% by weight, may be used.

When a graft and/or sequenced polymer is used as the stabilizer, the processing solvent is selected so that at least a portion of the grafts or sequences of said polymer-stabilizer is soluble in said solvent, the other portion of the grafts or sequences not being soluble therein. The polymer-stabilizer used during polymerization must be soluble or dispersible in the processing solvent. Further, it is preferable to select a stabilizer the insoluble sequences or grafts of which have a certain affinity for the polymer formed during polymerization.

Graft polymers that may be mentioned include silicone polymers grafted with a hydrocarbon chain; hydrocarbon polymers grafted with a silicone chain.

Thus, graft or sequenced block copolymers including at least one block of the polyorganosiloxane type and at least one block of a radical polymer may be used, such as graft copolymers of the acrylic/silicone type which may be used when the non aqueous medium is a silicone.

It is also possible to use graft or sequenced block copolymers comprising at least one block of the polyorganosiloxane type and at least one polyether. The polyorganosiloxane block may in particular be a polydimethylsiloxane or a polyalkyl($C_2$-$C_{18}$)methylsiloxane; the polyether block may be a $C_2$-$C_{18}$ polyalkylene, in particular polyoxyethylene and/or polyoxypropylene. In particular, it is possible to use copolyol dimethicones or ($C_2$-$C_{18}$)alkyl dimethicone copolyols such as those sold under the trade name "DOW CORNING 3225C" by DOW CORNING, or lauryl methicones such as those sold by "DOW CORNING Q2-5200 by "DOW CORNING".

Graft or sequenced block copolymers that may be mentioned include those comprising at least one block resulting from polymerizing at least one ethylenic monomer with one or more ethylenically unsaturated bonds which may be conjugated, such as ethylene or dienes such as butadiene or isoprene, and at least one block of a vinyl polymer and preferably styrene. When the ethylenic monomer comprises several ethylenically unsaturated bonds which may be conjugated, the residual ethylenically unsaturated bonds after polymerization are generally hydrogenated. In known manner, then, polymerization of the isoprene results in the formation of the ethylene-propylene block following hydrogenation, and butadiene polymerization results in the formation of the ethylene-butylene block after hydrogenation. Such polymers that may be mentioned include sequenced copolymers in particular of the two-block or three-block polystyrene/polyisoprene (SI), polystyrene/polybutadiene (SB) such as those sold under the trade name 'LUVITOL HSB' by BASF, of the polystyrene/copoly(ethylene-propylene) (SEP) type, such as those sold under the trade name "KRATON" by SHELL CHEMICAL Co or of the polystyrene/copoly(ethylene-butylene) (SEB) type. In particular, it is possible to use KRATON G1650 (SEBS), KRATON G1651 (SEBS), KRATON G1652 (SEBS), KRATON G1657X (SEBS), KRATON G1701X (SEP), KRATON G1702X (SEP), KRATON G1726X (SEB), KRATON D-1101 (SBS), KRATON D-1102 (SBS), or KRATON D-1107 (SIS). The polymers are generally termed copolymers of hydrogenated or non hydrogenated dienes.

It is also possible to use GELLED PERMETHYL 99A-750, 99A-753-59 and 99A-753-58 (mixture of three block and star polymer), VERSAGEL 5960 from PENRECO (three-block+star polymer); or OS129880, OS129881 and OS84383 from LUBRIZOL (styrene/methacrylate copolymer).

Graft or sequenced block copolymers comprising at least one block resulting from polymerizing at least one ethylenic monomer with one or more ethylenically unsaturated bonds and at least one block of an acrylic polymer that may be mentioned are two- or three-block poly(methyl methacrylate)/polyisobutene copolymers or graft copolymers with a poly(methyl methacrylate) backbone with polyisobutylene grafts.

Graft or sequenced block copolymers comprising at least one block resulting from polymerizing at least one ethylenic monomer with one or more ethylenically unsaturated bonds and at least one block of a polyether such as a $C_2$-$C_{18}$ polyalkylene (in particular polyethylene and/or polyoxypropylene) that may be mentioned are two- or three-block polyoxyethylene/polybutadiene or polyoxyethylene/polyisobutylene copolymers.

When a random polymer is used as the stabilizer, it is selected so that it has a sufficient quantity of groups to render it soluble in the envisaged processing solvent.

Thus, it is possible to use copolymers based on alkyl acrylates or methacrylates derived from $C_1$-$C_4$ alcohols, and alkyl acrylates or methacrylates derived from $C_8$-$C_{30}$ alcohols. In particular, stearyl methacrylate/methyl methacrylate copolymer may be mentioned.

When the polymer processing solvent is apolar, it is advantageous to select as the stabilizer a polymer which coats the particles in as complete a manner as possible, several polymer-stabilizer chains then becoming adsorbed on a particle of polymer obtained by polymerization.

It is then preferable to use as the stabilizer either a graft polymer or a sequenced polymer in order to have a better interfacial activity.

Sequences or grafts which are insoluble in the processing solvent produce a more voluminous coating on the particle surface.

When the processing solvent comprises at least one silicone oil, the stabilizing agent is preferably selected from the group constituted by graft or sequenced block copolymers comprising at least one polyorganosiloxane type block and at least one radical polymer block or polyether or polyester block, such as polyoxypropylene and/or oxyethylene blocks.

When the processing solvent includes silicone oil, the stabilizer agent is preferably selected from the group constituted by:
a) graft or sequenced block copolymers comprising at least one polyorganosiloxane type block and at least one block of a radical polymer or a polyether or a polyester;
b) copolymers of alkyl acrylates or methacrylates derived from $C_1$-$C_4$ alcohols, and alkyl acrylates or methacrylates derived from $C_8$-$C_{30}$ alcohols;
c) graft or sequenced block copolymers comprising at least one block resulting from polymerizing at least one ethylenically unsaturated monomer with conjugated ethylenically unsaturated bonds; and at least one block of a vinyl or acrylic polymer or a polyether or a polyester, or mixtures thereof.

Preferably, two block polymers are used as the stabilizer agent.

The film-forming polymer which is liposoluble or dispersed in an oily phase may also be used in a quantity of 0.01% to 20% (active substance) relative to the total composition weight, such as 1% to 10%, as appropriate.

I. Film-Forming Agent Dispersible in an Aqueous Phase of the Composition

In a further implementation, the film-forming polymer may be selected from aqueous dispersions of polymer particles when the composition of the invention comprises an aqueous phase.

The aqueous dispersion comprising one or more film-forming polymers may be prepared by the skilled person on the basis of general knowledge, in particular by emulsion polymerization or by dispersing the polymer formed.

Film-forming polymers which may be used in the composition of the present invention that may be mentioned include synthetic polymers of the polycondensate or radical type, polymers of natural origin, and mixtures thereof.

1) Polycondensates

Polycondensates that may also be mentioned are anionic, cationic, non ionic or amphoteric polyurethanes, polyurethane-acrylics, polyurethane-polyvinylpyrrolidones, polyester-polyurethanes, polyether-polyurethanes, polyureas, polyurea/polyurethanes, and mixtures thereof.

The polyurethanes may, for example, be a polyurethane copolymer, which may be aliphatic, cycloaliphatic or aromatic, a polyurea/polyurethane copolymer, or a polyurea copolymer, comprising used alone or as a mixture:
- at least one aliphatic and/or cycloaliphatic and/or aromatic sequence of linear or branched polyester origin; and/or
- at least one aliphatic and/or cycloaliphatic and/or aromatic sequence of polyether origin; and/or
- at least one silicone sequence, which may or may not be substituted and which may or may not be branched, for example polydimethylsiloxane or polymethylphenylsiloxane; and/or
- at least one sequence comprising fluorinated groups.

The polyurethanes as defined in the invention may also be obtained from polyesters, which may or may not be branched, or from alkyds comprising mobile hydrogens which are modified by means of a polyaddition with a diisocyanate and an organic bifunctional co-reagent compound (for example dihydro, diamino or hydroxy-amino), comprising in addition either a carboxylate group or carboxylic acid, or a sulfonate group or sulfonic acid, or even a neutralizable tertiary amine group or a quaternary ammonium group.

The polyesters may be obtained in known manner by means of polycondensation of aliphatic or aromatic dibasic acids avec aliphatic or aromatic diols or with polyols. Succinic acid, glutaric acid, adipic acid, pimelic acid, suberic acid, or sebacic acid may be used as aliphatic dibasic acids. Terephthalic acid or isophthalic acid, or even a derivative such as phthalic anhydride, may be used as aromatic dibasic acids. Glycol ethylene, glycol propylene, glycol diethylene, glycol neopentyl, cyclohexanedimethanol, and 4,4-N-(1-methylpropylidene)bisphenol, may be used as aliphatic diols. Glycerol, pentaerythritol, sorbitol, and trimethylolpropane may be used as polyols.

The polyesteramides may be obtained in a manner which is analogous to that used for polyesters, by means of polycondensation of dibasic acids with diamines or amino-alcohols. Ethylenediamine, hexamethylnediamine and meta- or para-phenylenediamine may be used as diamine. Monoethanolamine may be used as an aminoalcohol.

Examples of monomers carrying an anionic group which may be used during polycondensation that may be mentioned are dimethylolpropionic acid, trimellitic acid or a derivative such as trimellitic anhydride, the sodium salt of 3-sulfopentanediol and the sodium salt of 5-sulfo-1,3-benzenedicarboxylic acid. Polyesters with a fatty chain may be obtained using diols with a fatty chain during polycondensation. Epoxy ester resins may be obtained by polycondensating fatty acids with a condensate at the $\alpha$, $\omega$-diepoxy ends.

In particular, the radical polymers may be acrylic and/or vinyl polymers or copolymers. Polymers with an anionic radical are preferred. Examples of monomers carrying an anionic group which may be used during radical polymerization that may be mentioned are acrylic acid, methacrylic acid, crotonic acid, maleic anhydride and 2-acrylamido-2-methylpropanesulfonic acid.

The acrylic polymers may result from copolymerizing monomers selected from esters and/or amides of acrylic acid or methacrylic acid. Examples of ester type monomers that may be mentioned are methyl methacrylate, ethyl methacrylate, butyl methacrylate, isobutyl methacrylate, 2-ethylhexyl methacrylate and lauryl methacrylate. Examples of amide type monomers that may be mentioned are N-t-butylacrylamide and N-t-octylacrylamide.

In particular, acrylic polymers obtained by copolymerizing monomers with an ethylenically unsaturated bond containing hydrophilic groups, preferably non-ionic in nature are used, such as hydroxyethyl acrylate, 2-hydroxypropyl acrylate, hydroxyethyl methacrylate and 2-hydroxypropyl methacrylate.

Vinyl polymers may result from homo polymerization or copolymerization of monomers selected from vinyl esters, styrene or butadiene. Examples of vinyl esters that may be mentioned are vinyl acetate, vinyl neodecanoate, vinyl pivalate, vinyl benzoate and vinyl t-butylbenzoate.

It is also possible to use acrylic/silicone copolymers or even nitrocellulose/acrylic copolymers.

2) Polymer Type Radical

It is also possible to mention polymers resulting from radical polymerization of one or more radical monomers, within and/or partially on the surface of pre-existing particles of at least one polymer selected from the group constituted by polyurethanes, polyureas, polyesters, polyester amides and/or alkyds. Said polymers are generally termed "hybrid polymers".

When an aqueous dispersion of polymer particles is used, the dry matter content of said aqueous dispersion may be of the order of 3% to 60% by weight, preferably 10% to 50%.

The particle size of the polymers in aqueous dispersion may be in the range 10 nm to 500 nm, and it is preferably in the range 20 nm to 150 nm, allowing a film with a substantial gloss to be obtained. However, it is possible to employ particle sizes of up to one micron.

Examples of aqueous dispersions of film-forming polymers which may be used are acrylic dispersions sold under the trade names "NEOCRYL XK-90®", "NEOCRYL A-1070®, NEOCRYL A-1090®", "NEOCRYL HT-62®", "NEOCRYL A-1079®" and "NEOCRYL A-523®" from AVECIA-NEORESINS, "DOW LATEX 432®" from DOW CHEMICALS, "DAITOSOL 5000 AD®" or "DAITOSOL 5000 SJ" from DAITO KASEY KOGYO; "SYNTRAN 5760" from INTERPOLYMER or aqueous dispersions of polyurethane sold under the trade name "NEOREZ R-981®" and "NEOREZ R-974® from AVECIA-NEORESINS, "AVALURE UR-405®", "AVALURE UR-410®", "AVALURE UR-425®", "AVALURE UR-45®", SANCURE 875®", "SANCURE 861®", "SANCURE 878®" and "SANCURE 2060" from GOODRICH, "IMPRANIL 85®" from BAYER, "AQUAMERE H-1511®" from HYDROMER; sulfopolyesters sold under the trade name "EASTMAN AQ®" from EASTMAN CHEMICAL PRODUCTS, vinyl dispersions such as "MEXOMERE PAM", aqueous dispersions of polyvinylacetate such as "VINYBRAN®" from NISSHIN CHEMICAL or those sold by UNION CARBIDE, aqueous dispersions of vinyl pyrrolidone terpolymer, dimethylaminopropyl methacrylamide and lauryldimethylpropylmethacrylamidoammonium chloride, such as STYLEZE W from ISP, aqueous dispersions of polyurethane/polyacrylic polymers such as those sold under the trade name "HYBRIDUR®" by AIR PRODUCTS or "DUROMER" from NATIONAL STARCH, core/shell type dispersions: for example those sold by ATOFINA with reference number KYNAR (core: fluoride; shell: acrylic) or those described in U.S. Pat. No. 5,188,899 (core: silica; shell: silicone) and mixtures thereof.

When the composition includes an aqueous phase, the film-forming polymer may be a hydrosoluble polymer. The hydrosoluble polymer is thus dissolved in the aqueous phase of the composition.

Examples of hydrosoluble film-forming polymers that may be mentioned include the following cationic polymers:

1) Acrylic polymers or copolymers, such as poly acrylates or poly methacrylates; copolymers of category (1) may further contain one or more moieties deriving from co-monomers which may be selected from the acrylamide, methacrylamide, diacetoneacrylamides, acrylamides and methacrylamides substituted on the nitrogen by lower alkyls, acrylic or methacrylic acids or esters thereof, vinyllactames such as vinylpyrrolidone or vinylcaprolactame, and vinyl esters.

Thus, copolymers of family (1) that may be mentioned include:

copolymers of acrylamide and dimethylaminoethyl methacrylate quaternized by dimethyl sulfate, or by a dimethyl halide such as that sold under the trade name HERCOFLOC by HERCULES;

the copolymer of acrylamide and methacryloyloxyethyltrimethylammonium chloride described, for example, in patent application EP-A-0 809 76 and sold under the trade name BINA QUAT P 100 by CIBA GEIGY;

the copolymer of acrylamide and methacryloyloxyethyltrimethylammonium methosulfate sold under the trade name RETEN by HERCULES;

vinylpyrrolidone/dialkylaminoalkyl acrylate or methacrylate, quaternized or not quaternized, such as the products sold under the trade name "GAFQUAT" by ISP, such as "GAFQUAT 734" or "GAFQUAT 755", or products denoted as "COPOLYMER 845, 958 and 937". Those polymers are described in detail in French patents FR-A-2 077 143 and 2 393 573;

terpolymers of dimethylaminoethyl methacrylate/vinylcaprolactame/vinylpyrrolidone such as the product sold under the trade name GAFFIX VC 713 by ISP; and the vinylpyrrolidone/quaternized dimethylaminopropylmethacrylamide copolymer, such as the product sold under the trade name "GAFQUAT HS100" by ISP.

2) quaternized polysaccharides, described more particularly in U.S. Pat. No. 3,589,578 and U.S. Pat. No. 4,031,307, such as guar gums containing cationic trialkylammonium groups. Such products are in particular sold under the trade names JAGUAR C13 S, JAGUAR C 15 and JAGUAR C 17 by MEYHALL.

3) copolymers of quaternary vinylpyrrolidone and vinylimidazole;

4) chitosans or salts thereof;

5) cationic cellulose derivatives, such as copolymers of cellulose or cellulose derivatives grafted with a hydrosoluble monomer comprising a quaternary ammonium, described in particular in U.S. Pat. No. 4,131,576 such as hydroalkyl celluloses, such as hydroxymethyl, hydroxyethyl or hydroxypropyl celluloses, in particular grafted with a methacryloyloxyethyltrimethylammonium, methacrylamidopropyltrimethylammonium or dimethyldiallylammonium salt. Particular commercial products corresponding to that definition are products sold under the trade name "CELQUAT L 200" and "CELQUAT H 100" by NATIONAL STARCH COMPANY.

Hydrosoluble film-forming polymers that may be mentioned include the following amphoteric polymers:

1) polymers resulting from copolymerization of a monomer derived from a vinyl compound carrying a carboxylic group, more particularly acrylic acid, methacrylic acid, maleic acid, alpha-chloroacrylic acid and a basic monomer derived from a substituted vinyl compound containing at least one base atom, more particularly a dialkylaminoalkyl methacrylate or acrylate and a dialkylaminoalkylmethacrylamide and acrylamide. Said compounds are described in U.S. Pat. No. 3,836,537;

2) polymers comprising the moieties deriving:
a) from at least one monomer selected from acrylamides or methacrylamides substituted on the nitrogen by an alkyl radical;
b) from at least one acid co-monomer containing one or more carboxylic reactive groups; and
c) from at least one basic co-monomer such as esters, containing primary, secondary, tertiary and quaternary amine substituents or acrylic and methacrylic acids, and the product of quaternizing dimethylaminoethyl methacrylate with dimethyl or diethyl sulfate;
d) cross-linked alkoylpolyaminoamides completely or partially derived from polyaminoamide;
3) polymers comprising zwitterionic moieties;
4) the polymer derived from chitosan;
5) polymers derived from N-carboxyalkylation of chitosan, such as N-carboxymethyl chitosan or N-carboxybutyl chitosan sold under the trade name "EVALSAN" by JAN DEKKER;
6) ($C_1$-$C_5$)alkylvinylether/maleic anhydride copolymers partially modified by semi-amidification by a N,N-dialkylaminoalkylamine such as N,N-dimethylaminopropylamine or by semi-esterification by a N,N-dialkanolamine. Said copolymers may also comprise other vinyl co-monomers such as vinylcaprolactame.

The hydrosoluble film-forming polymers are preferably selected from the group constituted by:
proteins, such as proteins of vegetable origin, such as wheat or soya proteins; proteins of animal origin such as keratin, for example keratin hydrolysates or sulfonic keratins;
anionic, cationic, amphoteric or non-ionic polymers of chitin or chitosan;
cellulose polymers such as hydroxyethyl cellulose, hydroxypropyl cellulose, methylcellulose, ethylhydroxyethyl cellulose, carboxymethyl cellulose, and quaternized derivatives of cellulose;
acrylic polymers or copolymers such as polyacrylates or polymethacrylates;
vinyl polymers such as polyvinylpyrrolidones, copolymers of methylvinylether and maleic anhydride, the copolymer of vinyl acetate and crotonic acid, copolymers of vinylpyrrolidone and vinyl acetate;
copolymers of vinylpyrrolidone and caprolactame; polyvinyl alcohols;
optionally modified polymers of natural origin, such as:
gum arabic, guar gum, xanthan derivatives, karaya gum;
alginates and carragheens;
glycoaminoglycans, hyaluronic acid and its derivatives;
shellac, sanderac gum, dammar gums, gum elemi, copals;
deoxyribonucleic acid;
mucopolysaccharides such as hyaluronic acid, chondroitin sulfate, and mixtures thereof.

These polymers are used in particular if the film is to be largely eliminated with water.

To improve the film-forming nature of an oily or aqueous polymer, it is possible to add a coalescence agent to the polymer system, which agent is selected from known coalescence agents.

II. Silicone Film-Forming Agent
1) Polymer with a Grafted Non-Silicone Organic Backbone
Said polymers may be liposoluble, lipodispersible, hydrosoluble or dispersible in an aqueous medium, if appropriate.

Polymers with a non-silicone organic backbone grafted with monomers containing a polysiloxane are constituted by a principal organic chain formed by organic monomers comprising no silicone, onto which we graft, inside said chain and optionally on at least one of the ends thereof, at least one polysiloxane macromer.

In the following, it should be understood that the expression "polysiloxane macromer" designates, as is generally accepted, means any monomer containing a polymer chain of the polysiloxane type in its structure.

The non-silicone organic monomers constituting the principal chain of the graft silicone polymer may be selected from monomers with an ethylenically unsaturated bond which may be polymerized by the radical method, monomers polymerizable by polycondensation such as those forming polyamides, polyesters, polyurethanes, monomers with an opening cycle such as those of the oxazoline or caprolactone type.

Polymers having a non-silicone organic backbone grafted by monomers containing a polysiloxane of the present invention may be obtained using any method which is known to the skilled person, in particular by reaction between (i) a starting polysiloxane macromer correctly functionalized on the polysiloxane chain and (ii) one or more non-silicone organic compounds, themselves correctly functionalized by a function which is capable of reacting with the functional group or groups carried by said silicone, forming a covalent bond; a classic example of such a reaction is the radical reaction between a vinyl group carried at one end of the silicone with a double bond of a monomer with an ethylenically unsaturated bond of the principal chain.

Polymers having a non-silicone organic backbone grafted with monomers containing a polysiloxane of the invention are preferably selected from those described in U.S. Pat. No. 4,693,935, U.S. Pat. No. 4,728,571 and U.S. Pat. No. 4,972,037 and patent applications EP-A-0 412 704, EP-A-0 412 707, EP-A-0 640 105 and WO 95/00578. It concerns copolymers obtained by radical polymerization starting from monomers with an ethyleneically unsaturated bond and monomers having a terminal vinyl group, or copolymers obtained by reacting a polyolefin containing functionalized groups and a polysiloxane macromer having a terminal function which reacts with said functionalized groups.

A particular family of graft silicone polymers which is suitable for carrying out the present invention is constituted by graft silicone polymers containing:
a) 0 to 98% by weight of at least one lipophilic monomer (A) with a low lipophilic polarity with an ethylenically unsaturated bond, polymerizable by a radical method;
b) 0 to 98% by weight of at least one polar hydrophilic monomer (B) with an ethylenically unsaturated bond, copolymerizable with the monomer or monomers of type (A);
c) 0.01 to 50% by weight of at least one polysiloxane macromer (C) with general formula (XXVII):

$$X(Y)_n Si(R)_{3-m} Z_m \qquad (XXVII)$$

in which:
X designates a vinyl group copolymerizable with monomers (A) and (B);
Y designates a group having a divalent bond;
R designates hydrogen, alkyl or $C_1$-$C_6$ alkoxy, $C_6$-$C_{12}$ aryl;
Z designates a monovalent polysiloxane having a number average molecular mass of at least 500;

n is 0 or 1 and m is a whole number from 1 to 3; the percentages are calculated relative to the total weight of monomers (A), (B), and (C).

Said polymers have a number average molecular mass from 10000 to 2000000 and preferably a glass transition temperature Tg or a crystal melting temperature Tm of at least −20° C.

Examples of lipophilic monomers (A) that may be mentioned are esters of $C_1$-$C_{18}$ alcohol and acrylic or methacrylic acid; esters of $C_{12}$-$C_{30}$ alcohol and methacrylic acid; styrene; polystyrene macromers; vinyl acetate; vinyl propionate; alpha-methylstyrene; tertio-butylstyrene; butadiene; cyclohexadiene; ethylene; propylene; vinyltoluene, esters of acrylic or methacrylic acid and 1,1-dihydroperfluoroalkanols or homologues thereof; esters of acrylic or methacrylic acid and omega-hydrofluoroalkanols; esters of acrylic or methacrylic acid and fluoroalkylsulfonamidoalcohols; esters of acrylic or methacrylic acid and fluoroalkylalcohols; esters of acrylic or methacrylic acid and alcohol-fluoroethers; or mixtures thereof. Preferred monomers (A) are selected from the group constituted by n-butyl methacrylate, isobutyl methacrylate, tertio-butyl acrylate, tertio-butyl methacrylate, 2-ethylhexyl methacrylate, methyl methacrylate, 2-(N-methylperfluorooctanesulfonamido) ethyl acrylate, 2-(N-butylperfluorooctanesulfonamido)ethyl acrylate, or mixtures thereof.

Examples of polar monomers (B) that may be mentioned are acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and hemi-esters thereof, hydroxyalkyl(meth)acrylates, diallyldimethylammonium chloride, vinylpyrrolidone, vinyl ethers, maleimides, vinylpyridine, vinylimidazole, polar vinyl and heterocyclic compounds, styrene sultanate, allyl alcohol, vinyl alcohol, vinylcaprolactame or mixtures thereof. Preferably, monomers (B) are selected from the group constituted by acrylic acid, N,N-dimethylacrylamide, dimethylaminoethyl methacrylate, quaternized dimethylaminoethyl methacrylate, vinylpyrrolidone, and mixtures thereof.

In particular, the product KP 561 or KP 562 sold by SHIN ETSU may be mentioned in which monomer (A) is selected from esters of $C_{18}$-$C_{22}$ alcohol and methacrylic acid.

The polysiloxane macromers (C) with formula (XXVII) are preferably selected from those corresponding to the following general formula (XXVIII):

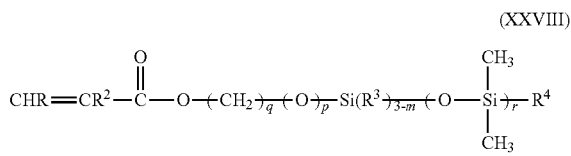

in which:

R$^1$ is hydrogen or —COOH (preferably hydrogen);

R$^2$ is hydrogen, methyl or —CH$_2$COOH (preferably methyl);

R$^3$ is alkyl, alkoxy or $C_1$-$C_6$ alkylamino, $C_6$-$C_{12}$ aryl or hydroxyl (preferably methyl);

R$^4$ is alkyl, alkoxy or $C_1$-$C_6$ alkylamino, $C_6$-$C_{12}$ aryl or hydroxyl (preferably methyl);

q is a whole number from 2 to 6 (preferably 3);

p is 0 or 1;

r is a whole number from 5 to 700;

m is a whole number from 1 to 3 (preferably 1).

Preferably, macromers of polysiloxane with formula (XXIX) are used:

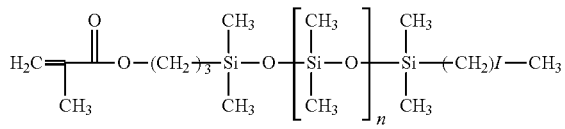

n being a number from 5 to 700 and I being a whole number in the range 0 to 3.

One implementation of the invention consists of using a copolymer which is capable of being obtained by radical polymerization starting from a mixture of monomers constituted by:

a) 60% by weight of tertio-butylacrylate;

b) 20% by weight of acrylic acid;

c) 20% by weight of silicone macromer with formula (XXX):

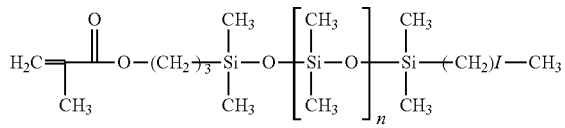

n being a number from 5 to 700 and I being a whole number in the range 0 to 3, the percentages by weight being calculated relative to the total weight of monomers.

A further particular implementation of the invention consists of using a copolymer which is capable of being obtained by radical polymerization from a mixture of monomers constituted by:

a) 80% by weight of tertio-butyl acrylate;

b) 20% by weight of silicone macromer with formula (XXXI):

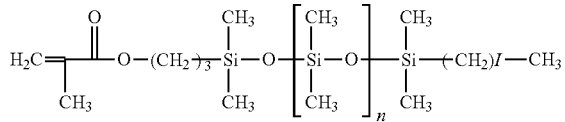

n being a number from 5 to 700 and I being a whole number in the range 0 to 3, the percentages by weight being calculated relative to the total monomer weight.

A further particular family of graft silicone polymers with an organic non-silicone backbone suitable for the present invention is constituted by graft silicone copolymers capable of being obtained by reactive extrusion of a polysiloxane macromer with a reactive terminal function on a polymer of the polyolefin type comprising reactive groups which are capable of reacting with the terminal function of a polysiloxane macromer to form a covalent bond to allow the silicone to graft onto the principal chain of the polyolefin. Said polymers, and their preparation process, have been described in International patent application WO-A-95/00578.

The reactive polyolefins are preferably selected from polyethylenes or polymers of monomers derived from ethylene, such as propylene, styrene, alkylstyrene, butylene, butadiene, (meth)acrylates, vinyl esters or the like, comprising reactive functions which are capable of reacting with the terminal function of the polysiloxane macromer. More particularly, they are selected from copolymers of ethylene or ethylene derivatives and monomers selected from those comprising a carboxylic function such as (meth)acrylic acid; those comprising an acid anhydride function such as maleic acid anhydride; those comprising an acid chloride function such as (meth)acrylic acid chloride; those comprising an ester function such as esters of (meth)acrylic acid; and those comprising an isocyanate function.

The silicone macromers are preferably selected from polysiloxanes comprising a functionalized group, at the end of the polysiloxane chain or close to the end of said chain, selected from the group constituted by alcohols, thiols, epoxies, primary and secondary amines, and more particularly from those corresponding to general formula (XXXII):

$$T\text{-}(CH_2)_6\text{--}Si\text{--}[\text{--}(OSiR^5R^6)_t\text{--}R^7]_y \quad (XXXII)$$

in which T is selected from the group constituted by $NH_2$, NHRN, an epoxy function, OH, SH; $R^5$, $R^6$, $R^7$ and RN independently designate $C_1$-$C_6$ alkyl, phenyl, benzyl or $C_6$-$C_{12}$ alkylphenyl, hydrogen; s is a number from 2 to 00, t is a number from 0 to 1000 and y is a number from 1 to 3. They preferably have a number average molecular mass from 5000 to 300000, more preferably from 8000 to 200000, and more particularly from 9000 to 40000.

In a particular implementation, the film-forming polymer may be obtained from the MINNESOTA MINING AND MANUFACTURING COMPANY under the polymer trade names "SILICONE PLUS". As an example, poly(isobutyl-co-FOSEA methyl methacrylate)-g-poly(dimethylsiloxane) is sold under the trade name SA 70-5 IBMMF.

2) Polymer with Silicone Backbone

Said graft silicone polymer or polymers has a polysiloxane backbone grafted with organic non-silicone monomers containing a principal silicone chain (or polysiloxane $(/SiO\text{--})_n$) on which is grafted, within said chain and optionally at one of its ends, at least one organic group comprising no silicone.

Polymers with a polysiloxane backbone grafted with organic non-silicone monomers of the invention may be existing commercially available products, or they may be obtained by any means known to the skilled person, in particular by a reaction between (i) a starting silicone correctly functionalized on one or more of its silicon atoms and (ii) an organic non-silicone compound itself correctly functionalized by a function which is capable of reacting with the functional group or groups carried by said silicone to form a coavalent bond; a classic example of said reaction is the hydrosilylation reaction between —Si—H groups and vinyl groups, $CH_2=CH—$, or the reaction between thiofunctional groups —SH and the same vinyl groups.

Examples of polymers having a polysiloxane backbone grafted with organic non-silicone monomers suitable for use in the present invention and their specific preparation methods are described in particular in patent applications EP-A-0 582 152, WO-A-93/23009 and WO-A-95/03776, the disclosures of which are included in their entirety in the present description by way of non-limiting reference.

In a particularly preferred implementation of the present invention, the silicone polymer with a polysiloxane backbone grafted with non-silicone organic monomers which is employed is constituted by the result of radical copolymerization between at least one non-silicone anionic organic monomer with an ethylenically unsaturated bond and/or a hydrophobic non-silicone organic monomer with an ethylenically unsaturated bond and a silicone having at least one functional group in its chain, and more preferably, capable of reacting with said ethylenically unsaturated bonds of said non-silicone monomers to form a covalent bond, in particular thiofunctional groups.

In accordance with the present invention, said anionic monomers with an ethylenically unsaturated bond are preferably selected, alone or as mixtures, from unsaturated linear or branched carboxylic acids which are optionally partially or completely neutralized into the salt form, said unsaturated carboxylic acid(s) more particularly possibly being acrylic acid, methacrylic acid, maleic acid, itaconic acid, fumaric acid or crotonic acid. Particular suitable salts are alkali, alkaline-earth and ammonium salts. It should be noted that, similarly, in the final graft silicone polymer, the organic group with an anionic nature which is constituted by the result of radical (homo)polymerization of at least one unsaturated carboxylic acid type anionic monomer may, after reaction, be post-neutralized with a base (sodium hydroxide, ammonia, etc) to put it into its salt form.

In the present invention, the hydrophobic monomers with an ethylenically unsaturated bond are preferably selected, alone or as a mixture, from esters of acrylic acid and alkanols and/or esters of methacrylic acid and alkanols. The alkanols are preferably $C_1$ to $C_{30}$, more particularly $C_1$ to $C_{22}$. Preferred monomers are selected from the group constituted by isooctyl(meth)acrylate, isononyl(meth)acrylate, 2-ethylhexyl(meth)acrylate, lauryl(meth)acrylate, isopentyl (meth)acrylate, n-butyl(meth)acrylate, isobutyl(meth)acrylate, methyl(meth)acrylate, tertio-butyl(meth)acrylate, tridecyl(meth)acrylate and stearyl(meth)acrylate, or mixtures thereof.

One family of silicone polymers having a polysiloxane backbone grafted with organic non-silicone monomers which is particularly suitable to carrying out the present invention is constituted by silicone polymers comprising the moiety with the following formula (XXXIII) in their structure:

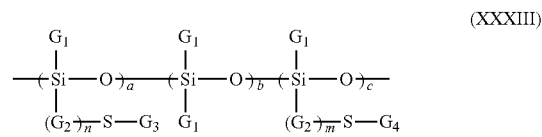

(XXXIII)

in which radicals G1, which may be identical or different, represent hydrogen or a $C_1$-$C_{10}$ alkyl radical, or a phenyl radical; radicals G2, which may be identical or different, represent a $C_1$-$C_{10}$ alkylene group; G3 represents a polymer residue resulting from (homo)polymerization of at least one anionic monomer having an ethylenically unsaturated bond; G4 represents a polymer residue resulting from (homo) polymerization of at least one monomer of at least one hydrophobic [sic] monomer with an ethylenically unsaturated bond; m and in equal 0 or 1; a is a whole number from 0 to 50; b is a whole number which may be in the range 10 to 350, c is a whole number from 0 to 50; provided that one of parameters a and c is other than 0.

The moiety with formula (XXXIII) above preferably has at least one and more preferably all of the following characteristics:

radicals $G_1$ designate an alkyl radical, preferably a methyl radical;

n is not zero, and radicals $G_2$ represent a divalent $C_1$-$C_3$ radical, preferably a propylene radical;

$G_3$ represents a polymer radical resulting from (homo) polymerization of at least one monomer of the carboxylic acid type with an ethylenically unsaturated bond, preferably acrylic acid and/or methacrylic acid;

$G_4$ represents a polymer radical resulting from (homo) polymerization of at least one monomer of the $C_1$-$C_{10}$ alkyl(meth)acrylate type, preferably isobutyl or methyl (meth)acrylate.

Particular examples of silicone polymers corresponding to formula (XXXIII) are polydimethylsiloxanes (PDMS) onto which are grafted, via a secondary thiopropylene type bond, mixed polymer moieties of the poly(meth)acrylic acid type and of the alkyl poly(meth)acrylic type.

Other particular examples of silicone polymers corresponding to formula (XXXIII) are polydimethylsiloxanes (PDMS) onto which are grafted, via a secondary thiopropylene type bond, polymer moieties mixed of the isobutyl poly(meth)acrylate type.

Such polymers comprise polymers comprising at least one group with formula (XXXIV):

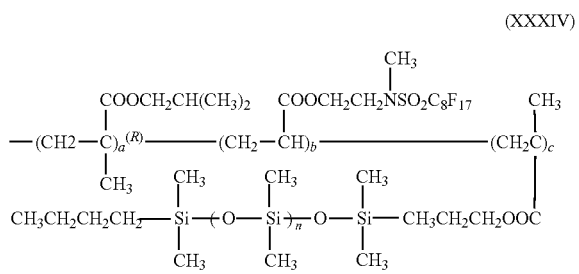

(XXXIV)

in which:

a, b and c, which may be identical or different, are each a number from 1 to 100000; and the terminal groups, which may be identical or different, are each selected from linear $C_1$ to $C_{20}$ alkyl groups, $C_3$ to $C_{20}$ alkyl groups with a branched chain, $C_3$ to $C_{20}$ aryl groups, linear $C_1$ to $C_{20}$ alkoxy groups and branched $C_3$ to $C_{20}$ alkoxy groups.

Such polymers are disclosed in the following patents: U.S. Pat. No. 4,972,037, U.S. Pat. No. 5,061,481, U.S. Pat. No. 5,209,924, U.S. Pat. No. 5,849,275 and U.S. Pat. No. 6,033,650, and WO 93/23446 and WO 95/06078.

Another family of silicone polymers having a polysiloxane backbone grafted by non-silicone organic monomers which is particularly suitable for implementation of the present invention is constituted by silicone polymers comprising the following moiety with formula (XXXV) in their structure:

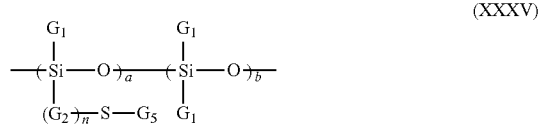

(XXXV)

in which radicals $G_1$ and $G_2$ have the meanings given above; $G_5$ represents a polymer residue resulting from (homo) polymerization of at least one hydrophobic monomer with an ethylenically unsaturated bond or from copolymerization of at least one anionic monomer with an ethylenically unsaturated bond and at least one hydrophobic monomer with an ethylenically unsaturated bond; n is equal to 0 or 1; a is a whole number from 0 to 50; b is a whole number which may be in the range 10 to 350; provided that a is other than 0.

The moiety with formula (XXXV) above preferably has at least one and more preferably all of the following characteristics:

radicals $G_1$ designate an alkyl radical, preferably a methyl radical;

n is not zero, and radicals $G_2$ represent a divalent $C_1$-$C_3$ radical, preferably a propylene radical.

The number average molecular mass of the silicone polymers having a polysiloxane backbone grafted by organic non-silicone monomers of the invention preferably varies from about 10000 to 1000000, more preferably from about 10000 to 100000.

In a particular implementation, a silicone film-forming polymer which is particularly suitable for the present invention may be a copolymer comprising carboxylate groups and polydimethylsiloxane groups.

The term "copolymer comprising carboxylate groups and polydimethylsiloxane groups" as used in the present invention means a copolymer obtained from a) one or more carboxylic monomers (acid or ester) and b) one or more polydimethylsiloxane chains (PDMS).

The term "carboxylic monomer" as used in the present application means both carboxylic acid monomers and carboxylic acid ester monomers. Thus, monomer a) may, for example, be selected from acrylic acid, methacrylic acid, maleic acid, fumaric acid, itaconic acid, crotonic acid, their esters and mixtures of said monomers. Ester monomers that may be mentioned: acrylate, methacrylate, maleate, fumarate, itaconoate and/or crotonoate. More particularly, monomers in the form of esters are selected from linear or branched alkyl acrylates and methacrylates, preferably $C_1$-$C_{24}$ and more preferably $C_1$-$C_{22}$, the alkyl radical preferably being selected from methyl, ethyl, stearyl, butyl, 2-ethylhexyl radicals, and mixtures thereof.

The copolymer may also comprise, as carboxylate groups, at least one group selected from acrylic acid, methacrylic acid, methyl, ethyl, stearyl, butyl, 2-ethylhexyl acrylates or methacrylates, and mixtures thereof.

The term "polydimethylsiloxanes" (also known as organopolysiloxanes, abbreviated to PDMS) as used here and conventionally, means any organosilicated oligomer or polymer with a linear structure, with various molecular weights, obtained by polymerization and/or polycondensation of appropriately functionalized silanes and essentially constituted by repeating the principal moieties in which the silicon atoms are connected together by oxygen atoms (siloxane bond ≡Si—O—Si≡), comprising trimethyl radicals directly connected via a carbon atom to said silicon atoms. The PDMS chains may be used to obtain the copolymer comprising at least one polymerizable radical group, preferably located on at least one of the chain ends, i.e. the PDMS may, for example, have a polymerizable radical on both ends of the chain or a polymerizable radical group on one end of the chain and a terminal trimethylsilyl group on the other end of the chain. The polymerizable radical group may in particular be an acrylic or methacrylic group, in particular a $CH_2=CR_1—CO—O—R_2$ group, in which $R_1$ represents a hydrogen or a methyl group, and $R_2$ represents —$CH_2$—, —$(CH_2)_n$—, in which n=3, 5, 8 or 10, —$CH_2$—$CH(CH_3)$—$CH_2$—, —$CH_2$—$CH_2$—O—$CH_2$—$CH_2$—, —$CH_2$—$CH_2$—O—$CH_2$—$CH(CH_3)$—$CH_2$—, or —$CH_2$—$CH_2$—O—$CH_2$ $CH_2$—O—$CH_2$—$CH_2$—$CH_2$—.

The copolymers used are generally obtained using the usual polymerization and grafting methods, for example by radical polymerization (A) of a PDMS comprising at least one polymerizable radical (for example on one end of the chain or on both ends) and (B) of at least one carboxylic monomer as described, for example, in U.S. Pat. No. 5,061,481 and U.S. Pat. No. 5,219,560.

The copolymers obtained generally have a molecular weight from about 3000 to 200000 and preferably from about 5000 to 100000.

The copolymer may be as is, or in the dispersed form in a solvent such as lower alcohols containing 2 to 8 carbon atoms, such as isopropyl alcohol, or oils such as volatile silicone oils (for example cyclopentasiloxane).

Examples of copolymers which may be used that may be mentioned are copolymers of acrylic acid and stearyl acrylate with polydimethylsiloxane grafts, copolymers of stearyl methacrylate with polydimethylsiloxane grafts, copolymers of acrylic acid and stearyl methacrylate with polydimethylsiloxane grafts, copolymers of methyl methacrylate, butyl methacrylate, 2-ethylhexyl acrylate and stearyl methacrylate with polydimethylsiloxane grafts. Particular suitable copolymers that may be mentioned are copolymers sold by SHIN-ETSU under the trade names KP-561 (CTFA: acrylates/dimethicone), KP-541 where the copolymer is dispersed at 60% by weight in isopropyl alcohol (CTFA name: acrylates/dimethicone and isopropyl alcohol), KP-545 where the copolymer is 30% dispersed in cyclopentasiloxane (CTFA name: acrylates/dimethicone and cyclopentasiloxane). In a preferred implementation of the invention, KP561 is used; that copolymer is not dispersed in a solvent, but is in a waxy form, its melting point being about 30° C.

More generally, the total quantity of polymer must be in a quantity sufficient to form a cohesive film on the skin and/or lips capable of following the movements of the skin and/or the lips without detaching or cracking.

When the polymer has too high a glass transition temperature for the desired use, a plasticizer may be associated with it to reduce that mixing temperature. The plasticizer may be selected from plasticizers which are normally used in the field of application, and especially from compounds which may be solvents for the polymer.

Active Ingredients

The first composition may include at least one cosmetically or dermatologically active ingredient. Suitable cosmetically, dermatologically, hygienically, or pharmaceutically active ingredients for use in the compositions of the invention that may be mentioned are moisturizing agents (polyols such as glycerine), vitamins (C, A, E, F, B, or PP), essential fatty acids, essential oils, ceramides, sphingolipids, liposoluble or nanoparticle sun screens, and specific skin treatment active ingredients (protective agents, antibacterials, anti-wrinkle agents, etc), self-tanning agents. Said active ingredients may be used in concentrations in the range 0 to 20%, for example, in particular in the range 0.001% to 15% relative to the total weight of the composition.

The first composition may also contain ingredients that are routinely used in cosmetics, such as thickeners, surfactants, oligo-elements, moisturizing agents, softeners, sequestrating agents, fragrances, alkalinizing or acidifying agents, preservatives, antioxidants, UV filters, colorants, or mixtures thereof.

Depending on the envisaged application, the first composition of the invention may include constituents which are conventionally used in the fields under consideration, and which are present in quantities appropriate to the desired dosage form.

Dosage Forms

The first and second composition(s), if any, may be, independently from each other, in a variety of forms, depending on its purpose. The first and second composition(s) may thus be in any dosage form that is normally used for topical application, in particular in the anhydrous form, in the form of an oily or aqueous solution, an oily or aqueous gel, an oil-in-water or a water-in-oil emulsion, a wax-in-water or a water-in-wax emulsion, a multiple emulsion or a dispersion of oil in water due to vesicles located on the oil/water interface.

The first and second composition(s), if any, may be, independently from each other, in the form of a powder, or even a gel.

Second Cosmetic Composition

The second composition may be transparent, possibly colorless, and may be for applying to the lips, the nails, or the skin, for example. It may comprise at least one of the components described above for the first composition.

The second composition may include at least one coloring agent, e.g. one of those listed above.

Where appropriate, the second composition may present magnetic properties, but in many implementations of the invention, only the first composition presents magnetic properties.

The second composition may be for covering the first composition or for being covered by the first composition.

When the second composition is colored, its color may optionally contrast with the color of the first composition.

The second composition may have the same dosage form as the first, and the above description concerning the composition medium and the possible active ingredients also applies to the second composition.

Magnetic Devices

The magnetic device may comprise a permanent magnet or an electromagnet powered by at least one optionally-rechargeable battery, for example. For a battery, the magnetic device may include a switch enabling the electromagnet to be powered selectively with electricity.

The magnetic device may be arranged so as to create a magnetic field of orientation that varies over time. When the magnetic device comprises a magnet, the device may, for example, include a motor enabling the magnet to be rotated. In a variant, the magnetic device may comprise a plurality of solenoids disposed so as to generate a rotating magnetic field when powered sequentially with electricity.

By way of example, a rotating magnetic field may make it possible to obtain a pattern presenting circular symmetry, e.g. a pattern giving the impression of a sphere in relief.

The electromagnet(s) may be powered continuously or intermittently, as desired by the user. In particular, the magnetic device may be arranged so that the electromagnets(s) need not be powered while the magnetic device is not correctly positioned close to the surface coated with the first composition.

The magnetic field is, for example, at least 50 milli teslas (mT), preferably at least 66 mT, or even at least 0.2 T or 1 T.

In order to make it easier to apply the magnetic field, the magnetic device may include a member enabling it to be positioned relative to the surface on which the first composition has been deposited. This makes it possible to prevent the magnetic device from accidentally coming into contact with the composition and/or makes it possible to center the pattern formed on the region under consideration.

In an implementation of the invention, the magnetic device is secured to an applicator that is used to apply the first cosmetic composition. This makes it possible to reduce the number of objects that need to be manipulated by the user and makes it easier to apply makeup.

In another implementation of the invention, the magnetic device comprises a magnet mounted at a first end of a rod having a second end that is connected to a handle/grip member of an applicator that is used to apply the first cosmetic composition.

The magnetic field may also be exerted by means of a magnetic structure, in particular a flexible structure, including alternate N and S poles. By way of example, such a structure may make it possible to form repeated patterns, e.g. stripes and recurring lines, on the first composition.

Kits for Implementing the Method

In another of its aspects, the invention also provides, a kit for implementing the method as defined above, said kit comprising:
a magnetic device enabling a magnetic field to be generated; and
a cosmetic composition including magnetic particles that are movable under the effect of a magnetic field.

The magnetic device may be capable of creating a magnetic field that is capable, when the keratinous material covered in a deposit of the composition is inserted in the magnetic field, of modifying the orientation and/or the position of the magnetic bodies inside the deposit.

The magnetic device may be arranged so as to generate a magnetic field that is sufficiently strong to be able to modify the orientation and/or the position of the magnetic particles within the first composition after it has been applied to a surface such as the skin, the lips, the nails, or hair, in order to change their appearance.

The invention provides, in another one of its aspects, a kit for implementing the method described above comprising:
a first makeup composition comprising:
i) at least one volatile solvent, especially a volatile oil; and
ii) magnetic particles; and
a magnetic device.

By way of example, when the first composition contains a volatile solvent, the magnetic field may be exerted shortly after it has been deposited, so as to change the appearance of said first composition before it has dried.

Advantageously, the first composition further comprises at least one film-forming polymer.

In a further one of its aspects, the invention provides, a kit for implementing the method as defined above, said kit comprising:
a magnetic device enabling a magnetic field to be generated; and
a first cosmetic composition including:
at least one magnetic particle; and
at least one coloring agent having optical properties that are sensitive to an external stimulus; the magnetic device being capable of creating a magnetic field that is capable, when the surface covered in a deposit of said composition is inserted in said magnetic field, of modifying the orientation and/or the position of the magnetic particles inside the deposit.

In yet a further one of its aspects, the invention provides, a kit for implementing the method as defined above, said kit comprising:
a magnetic device enabling a magnetic field to be generated; and
a first cosmetic composition including:
magnetic particles; and
at least one diffractive pigment; the magnetic device being capable of creating a magnetic field that is capable, when the surface covered in a deposit of said composition is inserted in said magnetic field, of modifying the orientation and/or the position of the magnetic particles inside the deposit.

In yet another one of its aspects, the invention provides, a kit for implementing the method as defined above, said kit comprising:
a magnetic device enabling a magnetic field to be generated; and
a first cosmetic composition including:
at least one magnetic particle; and
at least one coloring agent producing a color by absorbing at least a fraction of the visible spectrum; the magnetic device being capable of creating a magnetic field that is capable, when the surface covered in a deposit of said composition is inserted in said magnetic field, of modifying the orientation and/or the position of the magnetic particles inside the deposit.

By way of example, the first composition may be a nail varnish, a foundation, or a lipstick, and may present the characteristics as defined above.

The magnetic device may be as defined above.

In particular, the magnetic device may comprise at least one permanent magnet or an electromagnet powered, for example, by a battery, in which case the magnetic device may include a switch so that the electromagnet can be powered selectively with electricity.

The magnetic device of the kit may be arranged to create a magnetic field of orientation that varies with time. When the magnetic device comprises a magnet, the device may, for example, include a motor to rotate the magnet. In a variation, the magnetic device may include a plurality of solenoids disposed so that, when sequentially powered with electricity, a rotating magnetic field is generated.

A rotary magnetic field may, for example, produce a pattern with symmetry of revolution, for example a pattern giving the impression of a sphere in relief.

The electromagnet or electromagnets may be powered permanently or intermittently, as dictated by the user. In particular, the magnetic device of the kit may be arranged so that the electromagnet or electromagnets are not powered while the magnetic device is not correctly positioned close to the surface coated with composition.

The magnetic field is, for example, at least 50 mT [megaTorr], or even at least 0.2 T or 1 T.

In order to render application of the magnetic field easier, the magnetic device of the kit may include a member that allows it to be positioned relative to the surface on which the composition has been deposited. This may, for example, prevent the magnetic device from accidentally coming into contact with the composition and/or to allow the pattern produced to be centered on the region concerned.

The magnetic device of the kit may be attached to an applicator allowing the cosmetic composition to be applied. This reduces the number of articles that are manipulated by the user and facilitates making up.

The magnetic device of the kit may include a magnet mounted at one end of a rod having its other end connected to a grip member of an applicator serving to apply the cosmetic composition.

The magnetic field may also be exerted by means of a magnetic structure, especially a flexible structure, comprising alternating N and S poles. Such a structure may, for example, produce repeating patterns on the composition, for example stripes.

The kit may comprise a casing, such as a compact case, housing the first cosmetic composition and the magnetic device. In this event, the casing may, for example, include a plurality of magnets of various shapes in order to produce different patterns.

The kit may also comprise a second cosmetic composition for applying to the first, or to the surface before the first composition is applied.

A Second Cosmetic Composition for Applying to the First, or to be Covered by the First According to yet another one of its aspects, the invention provides a kit for applying makeup to a surface (S) such as the skin, the nails, hair or the lips, said kit comprising:
  a first cosmetic composition (CO including metallic iron particles, in particular soft iron; and
  a second cosmetic composition ($C_2$) for covering or for being covered by the first composition (C1).

According to another of its aspects, the invention provides a kit for applying makeup to a surface such as the skin, the nails, hair, the lips, or even false nails, said kit comprising:
  a first cosmetic composition including magnetic particles that are movable under the effect of a magnetic field;
  a second cosmetic composition for covering or for being covered by the first composition, said kit may also comprise:
  a magnetic device for generating the magnetic field that makes it possible to displace and/or modify the orientation of all or some of the magnetic particles when the first composition is applied in the form of at least one layer to the surface.

According to these aspects, the first cosmetic composition, the second cosmetic composition, the magnetic device and the magnetic particles may be as defined further above for the method of applying makeup.

The term "movable" means that the orientation and/or the position of the particles can be modified.

The appearance of the first composition deposited on the surface depends on the orientation and/or the position of the magnetic particles. The invention makes it possible to create novel makeup effects, enabling patterns in relief to be produced, for example, or imparting an impression of relief or various other possibly geometrical patterns.

The second composition may be transparent. When the second cosmetic composition is applied to the first, it makes it possible to obtain a depth, gloss, smoothness, or other effect.

The second composition may include a coloring agent, e.g. pigments. When the second composition is colored, it possible to create a colored background/base, for example, the second composition thus being covered by the first, for example.

In particular, the kit of the invention may be used to apply makeup to the lips or to the nails.

The kit of the invention may include a magnetic device for generating a magnetic field that makes it possible to modify the appearance of the first composition, at least immediately after it has been applied to the surface.

Promotion Method

The invention also provides a method of promoting the sale of a composition presenting magnetic properties, the method comprising the step consisting in demonstrating the possibility of creating a pattern or a portion in relief by applying a magnetic field and/or the possibility of changing appearance by exposure to an external stimulus such as a variation in temperature, or exposure to UV radiation, for example.

BRIEF DESCRIPTION OF THE DRAWINGS

Examples

The invention will be better understood on reading the following detailed description of non-limiting implementations thereof, and on examining the accompanying drawings, in which:

FIG. 1 is a diagram showing an example of a kit of the invention;

FIG. 2 is a diagrammatic and fragmentary axial section view showing the magnetic device of FIG. 1;

FIGS. 3 and 4 are diagrams showing the kit being used;

FIG. 5 shows an example of a pattern that can be obtained by means of the invention;

FIG. 6 is a diagram showing a receptacle containing a second composition that is suitable for being applied to the surface;

FIG. 7 is a diagram showing, in isolation, another example of a magnetic device that can be used;

FIG. 8 is a diagram showing the FIG. 7 magnetic device provided with a positioning member for positioning the magnet facing the made-up surface;

FIGS. 9 and 10 are diagrams of other examples of kits of the invention;

FIG. 11 shows the FIG. 10 kit being used;

FIG. 12 is a diagram showing, in elevation and in isolation, an example of an applicator secured to a magnetic device;

FIG. 13 is an axial and diagrammatic section of another example of a kit of the invention;

FIG. 14 is a diagram showing another example of a kit of the invention;

FIG. 15 shows another example of a packaging device for the first composition;

FIG. 16 shows a perforated mask that is suitable for being used during implementation of the method of the invention;

FIG. 17 shows a magnetic sheet that is suitable for being used during implementation of the method of the invention;

DETAILED DESCRIPTION OF THE INVENTION

Figure 18:
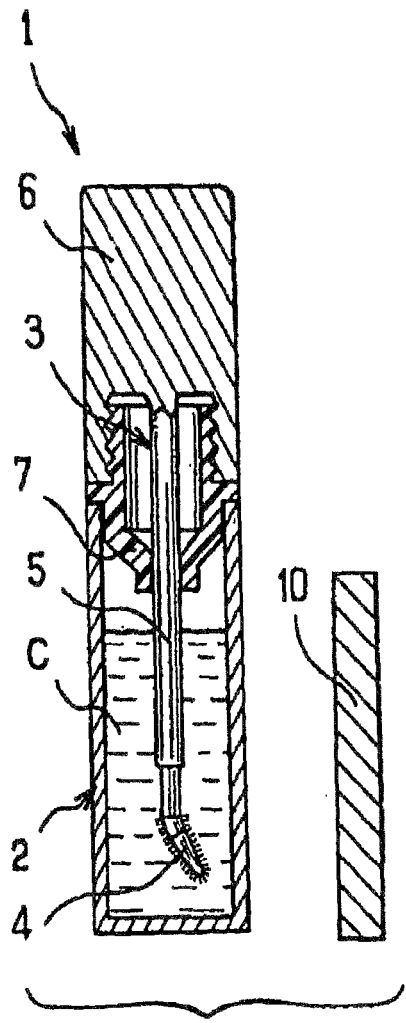
FIG. 18 diagrammatically shows an example of a kit for carrying out the method.

In the figures, magnetic particles are shown in the form of dots in order to make the drawings easy to understand, but in reality the individual particles need not be visible to the naked eye.

FIG. 1 shows a kit 1 comprising a first cosmetic composition $C_1$ containing magnetic particles P having orientation and/or position that affects the appearance of the composition after it has been deposited on a surface such as the skin, the lips, the nails, hair, or even false nails.

In the embodiment shown, the composition $C_1$ is a nail varnish contained in a receptacle 2 that is closed by a cap 3. The cap supports a non-magnetic cosmetics applicator 4 including an applicator member 5 constituted by a brush enabling the varnish to be applied to the nails.

The kit 1 further comprises a magnetic device 10 that makes it possible to generate a magnetic field that is useful for changing the appearance of the first composition $C_1$ without making contact therewith.

In the embodiment under consideration, the magnetic device 10 comprises a permanent magnet 12 supported by a support member 13 of longitudinal axis X, the polar axis of the magnet 12 being substantially perpendicular to the axis X.

In the embodiment under consideration, the magnetic device 10 is arranged to generate a rotating magnetic field, and includes a motor (not shown), housed in a casing 15, so as to rotate the support member 13 about it axis X.

A switch 16 is present on the casing 15 so as to enable the user to switch on the motor, thereby rotating the support member 13 together with the magnet 12.

In a variant not shown, the rotating magnetic field is generated by a plurality of solenoids that are powered sequentially so as to generate a rotating field.

In order to use the kit 1, the user can begin, as shown in FIG. 3, by applying the first composition $C_1$ by means of an applicator 4 to the surface S to be made up, specifically a fingernail.

In the subsequent step shown in FIG. 4, the user brings the magnetic device 10 over a central region R of the surface S and actuates the switch 16 so as to make the magnet 12 turn.

The magnetic particles contained in the first composition $C_1$ tend to come into alignment with the field lines of the magnet 12 and change orientation, thereby leading to a change in the appearance of the composition $C_1$.

The user can choose the length of time the magnetic field is to be applied as a function of the desired result.

By way of example, the pattern obtained can give the impression of a sphere in relief, as shown in FIG. 5.

If necessary, the user can apply a second composition $C_2$, e.g. a transparent varnish, contained in a receptacle shown in FIG. 6, once the first composition $C_1$ has dried.

Applying the second composition $C_2$ makes it possible to create an effect of additional depth, for example.

In the nail varnish embodiment in FIGS. 1 to 5, the first composition $C_1$ may have the following formulations, with quantities being expressed in percentages by weight in all of the examples below.

Example A-1

| | |
|---|---|
| Nitrocellulose | 11 |
| N-ethyl o,p-toluenesulfonamide | 5 |
| Alkyde resin | 10 |
| Isopropanol | 4 |
| Magnetic pigments* | 0.5 |
| Butyl acetate/ethyl acetate 50/50 | Qsp 100 |

*Nacres containing at least 14% of $Fe_3O_4$, referenced COLORONA PATINA GOLD (117288), and sold by MERCK.

Example A-2 Nail Varnish Incorporating a Photochromic Agent

| | |
|---|---|
| Nitrocellulose | 11 |
| N-ethyl o,p-toluenesulfonamide | 5 |
| Alkyde resin | 10 |
| Isopropanol | 4 |
| Magnetic pigment* | 0.5 |
| Photochromic coloring agent** | 3 |
| Butyl acetate/ethyl acetate 50/50 | Qsp 100 |

*STAPA WM IRON VP 041040 by ECKART
**Reversacol from James ROBINSON

Once the composition has dried, the pattern generated by magnetic induction is frozen. Its color depends on the photochromic coloring agent. Depending on the magnetic excitation, the pigment presents a dull or lively color, thus optionally enhancing the decorative effect obtained by the magnetic pigment.

Example A-3 Nail Varnish Incorporating a Diffractive Pigment

| | |
|---|---|
| Nitrocellulose | 11 |
| N-ethyl o,p-toluenesulfonamide | 5 |
| Alkyde resin | 10 |
| Isopropanol | 4 |
| Magnetic pigment* | 0.5 |
| Diffractive pigment** | 3 |
| Butyl acetate/ethyl acetate 50/50 | Qsp 100 |

*Nacres containing at least 14% of $Fe_3O_4$, referenced COLORONA PATINA GOLD (117288), and sold by MERCK.
**SPECTRAFLAIR pigment from FLEX PRODUCTS.

Example A-4 Nail Varnish Incorporating an Absorbent Coloring Agent

| | |
|---|---|
| Nitrocellulose | 11 |
| N-ethyl o,p-toluenesulfonamide | 5 |
| Alkyde resin | 10 |
| Isopropanol | 4 |
| Magnetic pigment* | 0.5 |
| Butyl acetate/ethyl acetate 50/50 | Qsp 100 |

*Prussian blue CI 74160 - Such a pigment produces a color by an absorption phenomenon.

The appearance of such nail varnishes A-1 to A-4 can be changed by applying a magnetic field before the varnish has had time to dry.

By way of example, when a second composition $C_2$ is applied to the first, said second composition has the following formulation, for example, and may be applied to the first, after the first has dried.

Example B

| | |
|---|---|
| Nitrocellulose | 11 |
| N-ethyl o,p-toluenesulfonamide | 5 |
| Alkyde resin | 10 |
| Isopropanol | 4 |
| Butyl acetate/ethyl acetate 50/50 | Qsp 100 |

Such a composition makes it possible to create an effect of additional depth.

In a variant embodiment of the invention, the second composition $C_2$ may be applied before the first composition $C_1$, so as to create a colored background/base, for example.

The first composition $C_1$ can thus be less covering.

The following examples are examples of a second composition for creating a colored background/base, the first composition having the formulation of above-mentioned example A-1, for example.

Examples C-1 and C-2

|  | C-1 | C-2 |
|---|---|---|
| Nitrocellulose | 11 | 11 |
| N-ethyl o,p-toluenesulfonamide | 4 | 5 |
| Alkyde resin | 6 | 10 |
| Isopropanol | 4 | 4 |
| DC RED7 CI 15850 pigment | 2 | 2 |
| Butyl acetate/ethyl acetate 50/50 | Qsp 100 | Qsp 100 |

The composition in example A-1 contains only one type of magnetic pigment.

The following example shows the possibility of having, within the composition, magnetic pigments and another coloring substance, e.g. pigments having a variable optical effect, in this event goniochromatic pigments.

Example D

| Nitrocellulose | 11 |
|---|---|
| N-ethyl o,p-toluenesulfonamide | 5 |
| Alkyde resin | 10 |
| Isopropanol | 4 |
| COLORONA BLACKSTAR GOLD, MERCK ® (magnetic pigments) | 2.5 |
| SICOPEARL FANTASTICO ROSE, BASF ® (goniochromatic pigments) | 2.5 |
| Butyl acetate/ethyl acetate 50/50 | Qsp 100 |

In this example, the magnetic pigment is gold in color, said color being present on the color path of the goniochromatic pigment.

Without magnetic excitation, the mixture presents a goniochromatic effect without any visible pattern, the color of the magnetic pigment not masking the goniochromatic effect. It is possible to see a surface having a base color varying from gold to pink.

In contrast, after applying a magnetic field, the magnetic pigments coming into alignment with the field lines create a pattern that becomes superimposed on the color changes that result from the goniochromatic pigment. A gold-colored pattern obtained by means of the particles of oriented magnetic pigment can thus appear on a pink base for some orientation conditions concerning the observer and/or the made-up surface.

A second composition having, for example, the same formulation as that of Example B, may be applied to the first, after the first has dried.

Example E Nail Varnish Incorporating a Thermochromic Agent

| Nitrocellulose | 11 |
|---|---|
| N-ethyl o,p-toluenesulfonamide | 5 |
| Alkyde resin | 10 |
| Isopropanol | 4 |
| Magnetic pigment* | 0.5 |
| Thermochromic coloring agent** | 3 |
| Butyl acetate/ethyl acetate 50/50 | Qsp 100 |

*Colorona Blackstar Red from Merck
**Thermostar ® from CHROMAZONE

Once the composition has dried, the pattern generated by magnetic induction is frozen. Its color depends on the thermochromic coloring agent. Depending on the magnetic excitation, the thermochromic pigment presents a dull or lively color as a function of the temperature, thus optionally enhancing the decorative effect obtained by the magnetic pigment.

Naturally, whatever the nature of said composition, the magnetic field applied thereto need not rotate. By way of example, FIG. 7 shows a magnetic device which, at its end, includes a permanent magnet 12 in the form of a bar.

When the magnetic field does not rotate, the user can, for example, move the magnet into the vicinity of the first composition as a function of the desired result.

Whatever its nature, the magnetic device may include a member enabling it to be positioned relative to the surface S.

By way of example, the positioning member serves to prevent the magnetic device from touching the composition while the magnetic field is being exerted.

The positioning member can also serve to center the pattern that is produced relative to the surface S, e.g. the nail.

Depending on the nature of the surface, the positioning member could take various forms, e.g. that of an extension 17 offering an abutment surface for engaging the end of the finger, as shown in FIG. 8.

FIG. 9 shows another embodiment of a kit 1 of the invention, including a first composition $C_1$ constituted in this embodiment by a liquid lipstick or a lip gloss.

In this embodiment, the applicator 4 comprises a flocked endpiece 20 supported by the cap 3 of the receptacle 2.

By way of example, the magnetic device 10 is in the form of a flexible structure, e.g. made of plastics material filled with magnetized particles, creating alternate N and S poles, thereby making it possible to form repeated patterns, e.g. stripes, on the surface coated with the first composition.

By way of example, for lipstick, the composition $C_1$ presents the following formulation.

Example F-1

| Octyl-2 dodecanol | 10 |
|---|---|
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |

-continued

| | |
|---|---|
| Tridecyle trimellitate | 13 |
| 2-decyl tetradecanoic acid triglyceride (GUERBET C24) | 15 |
| Magnetic pigments* | 0.2 |

*Nacres containing at least 14% of $Fe_3O_4$, sold under the reference CLOISONNE NU ANTIQUE GREEN 828 CB by ENGELHARD.

By way of example, a second composition may be applied to the composition above and has the following formulation.

Second Composition

| | |
|---|---|
| Degussa Aerosil R972 | 5 |
| Hydrogenated polyisobutylene (Parleam oil) | 2.1 |
| Octyldodecanol | 0.9 |
| Phenylated silicone oil (Dow Corning 556C) | 2.1 |
| Polyvinyl pyrrolidone and Eicosene copolymer (ISP Anatron V220) | 1.2 |
| Isododecane | Qsp 100 |

The second composition may be applied to the first and makes it possible to create an effect of depth.

Example F-2 Lipstick Incorporating a Solvatochromic Agent

| | |
|---|---|
| Octyl-2 dodecanol | 10 |
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |
| Tridecyle trimellitate | 13 |
| 2-decyl tetradecanoic acid triglyceride (GUERBET C24) | 14.8 |
| Magnetic pigment* | 0.2 |
| Solvatochromic coloring agent** | 0.2 |

*Colorona blackstar gold from Merck
**DCRED27

Once the composition has been applied, the pattern is generated by magnetic induction. Its color depends on the solvatochromic coloring agent. Depending on the magnetic excitation, the compound presents a color that is pink or not as a function of the hydration, thus optionally enhancing the decorative effect obtained by the magnetic pigment.

Example F-3 Lipstick Incorporating a Diffractive Pigment

| | |
|---|---|
| Octyl-2 dodecanol | 10 |
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |
| Tridecyle trimellitate | 13 |
| 2-decyl tetradecanoic acid triglyceride (GUERBET C24) | 15 |
| Magnetic pigment* | 0.2 |
| Diffractive pigment** | 3 |

*Nacres containing at least 14% of $Fe_3O_4$, sold under the reference CLOISONNE NU ANTIQUE GREEN 828 CB by ENGELHARD.
**SPECTRAFLAIR pigment from FLEX PRODUCTS.

Example F-4 Lipstick Incorporating an Absorbent Coloring Agent

| | |
|---|---|
| Octyl-2 dodecanol | 10 |
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |
| Tridecyle trimellitate | 13 |
| 2-decyl tetradecanoic acid triglyceride (GUERBET C24) | 15 |
| Magnetic pigment* | 0.2 |

*Prussian blue CI 74160 - Such a pigment produces a color by an absorption phenomenon.

Example F-5 Lipstick Incorporating an Absorbent Coloring Agent

| | |
|---|---|
| Octyl-2 dodecanol | 10 |
| Ditertiobutyl 4-hydroxytoluene | 0.07 |
| Polybutene (monoolefins/isoparaffins 95/5) (PM: 2060) | 50 |
| A mixture of isopropyl, isobutyl, and n-butyl p-hydroxybenzoates (40/30/30) | 0.4 |
| Pentaerythrityl tetraisostearate | 11.33 |
| Tridecyle trimellitate | 12 |
| 2-decyl tetradecanoic acid triglyceride (GUERBET C24) | 14 |
| Magnetic pigment* | 0.2 |
| Pigment CD RED7 CI 15850 | 2 |

*Prussian blue CI 74160.

Another kit 1 of the invention is shown in FIG. 10. In this embodiment, the kit 1 includes a compact 30 constituted by a base body 31 and a lid 32 hinged thereon.

The base body 31 includes a compartment 33 housing the composition $C_1$, which, in the embodiment shown, is constituted by a foundation in the form of a paste.

The base body 31 includes a housing 34 arranged to receive at least one magnet 12.

By way of example, the magnet 12 may present an adhesive face 25 or any other mounting means enabling the user to fix it to the end of a finger so as to bring it into the vicinity of the made-up zone, e.g. a region of the face as shown in FIG. 11.

After applying the first composition $C_1$ to the skin, the user can modify the clarity of said composition by exposing it to the magnetic field generated by the magnet 12.

By way of example, for a foundation, said foundation can have the following formulation.

Example G-1

| | |
|---|---|
| Magnesium sulfate | 1.5 |
| Sodium carboxymethylcellulose | 0.5 |
| Distearyldimethylammonium modified hectorite | 1 |
| Cyclopenta dimethylsiloxane | 16 |
| Glycerol | 5 |
| A mixture of oxyethylenated polymethylketyldimethyl methylsiloxane, polyglycerol isostearate (4 moles), hexyl laurate | 9 |

-continued

| | |
|---|---|
| Water | 31.6 |
| A mixture of ethylene glycol acetyl stearate, glyceryl tristearate | 0.3 |
| Brown iron oxide coated with aluminum stearoyl glutamate(97/3) | 1.58 |
| Anatase titanium oxide coated with stearoyl glutamate(97/3) | 18.17 |
| Yellow iron oxide coated with aluminum stearoyl glutamate (93/3) | 4.56 |
| Black iron oxide coated with aluminum stearoyl glutamate (97/3) | 0.69 |
| Polydimethylsiloxane (viscosity: 5 cSt) | 6 |
| Magnetic pigments* | 0.5 |
| 1,2-pentanediol | 3 |

*Nacres with at least 14% of $Fe_3O_4$, sold by Merck under the reference TIMICA NU ANTIQUE BRONZE 240 AB.

By way of example, for a composition for making up the skin, said composition can have the following formulations.

Example G-2 Foundation Incorporating a Photochromic Agent

| | |
|---|---|
| Magnesium sulfate | 1.5 |
| Sodium carboxymethylcellulose | 0.5 |
| Distearyldimethylammonium modified hectorite | 1 |
| Cyclopenta dimethylsiloxane | 15 |
| Glycerol | 5 |
| A mixture of oxyethylenated polymethylketyldimethyl methylsiloxane, polyglycerol isostearate (4 moles), hexyl laurate | 9 |
| Water | 30.6 |
| A mixture of ethylene glycol acetyl stearate, glyceryl tristearate | 0.3 |
| Brown iron oxide coated with aluminum stearoyl glutamate(97/3) | 1.58 |
| Anatase titanium oxide coated with stearoyl glutamate(97/3) | 17.17 |
| Yellow iron oxide coated with aluminum stearoyl glutamate (93/3) | 4.56 |
| Black iron oxide coated with aluminum stearoyl glutamate (97/3) | 0.69 |
| Polydimethylsiloxane (viscosity: 5 cSt) | 6 |
| Magnetic pigments* | 0.5 |
| Xchromic coloring agent** | 3 |
| 1,2-pentanediol | 3 |

*Nacres with at least 14% of $Fe_3O_4$, sold by Merck under the reference TIMICA NU ANTIQUE BRONZE 240 AB.
**Photogenica ® from CATALYST & CHEMICALS

Example G-3 Foundation Incorporating a Diffractive Pigment

| | |
|---|---|
| Magnesium sulfate | 1.5 |
| Sodium carboxymethylcellulose | 0.5 |
| Distearyldimethylammonium modified hectorite | 1 |
| Cyclopenta dimethylsiloxane | 15 |
| Glycerol | 5 |
| A mixture of oxyethylenated polymethylketyldimethyl methylsiloxane, polyglycerol isostearate (4 moles), hexyl laurate | 9 |
| Water | 30.6 |
| A mixture of ethylene glycol acetyl stearate, glyceryl tristearate | 0.3 |
| Brown iron oxide coated with aluminum stearoyl glutamate(97/3) | 1.58 |
| Anatase titanium oxide coated with stearoyl glutamate(97/3) | 17.17 |
| Yellow iron oxide coated with aluminum stearoyl glutamate (93/3) | 4.56 |
| Black iron oxide coated with aluminum stearoyl glutamate (97/3) | 0.69 |
| Polydimethylsiloxane (viscosity: 5 cSt) | 6 |
| Magnetic pigments* | 0.5 |
| Diffractive pigment** | 3.6 |
| 1,2-pentanediol | 3 |

*Nacres with at least 14% of $Fe_3O_4$, sold by Merck under the reference TIMICA NU ANTIQUE BRONZE 240 AB.
**SPECTRAFLAIR pigment from FLEX PRODUCTS.

Example G-4 Foundation Incorporating an Absorbent Coloring Agent

| | |
|---|---|
| Magnesium sulfate | 1.5 |
| Sodium carboxymethylcellulose | 0.5 |
| Distearyldimethylammonium modified hectorite | 1 |
| Cyclopenta dimethylsiloxane | 16 |
| Glycerol | 5 |
| A mixture of oxyethylenated polymethylketyldimethyl methylsiloxane, polyglycerol isostearate (4 moles), hexyl laurate | 9 |
| Water | 31.6 |
| A mixture of ethylene glycol acetyl stearate, glyceryl tristearate | 0.3 |
| Brown iron oxide coated with aluminum stearoyl glutamate(97/3) | 1.58 |
| Anatase titanium oxide coated with stearoyl glutamate(97/3) | 18.17 |
| Yellow iron oxide coated with aluminum stearoyl glutamate (93/3) | 4.56 |
| Black iron oxide coated with aluminum stearoyl glutamate (97/3) | 0.69 |
| Polydimethylsiloxane (viscosity: 5 cSt) | 6 |
| Magnetic pigment* | 0.5 |
| 1,2-pentanediol | 3 |

*Prussian blue CI 74160.
Iron and titanium oxides are coloring agents that produce a color by an absorption phenomenon.

Whatever the type of applicator, the magnet 12 may, where appropriate, be incorporated in the applicator.

In the embodiment in FIG. 12, the closure cap 3 is surmounted by the magnet 12 on the side remote from the applicator member 5.

In the embodiment in FIG. 13, the magnet 12 is supported by a support member 13 surmounted by a cap 51, and can, when not in use, be housed in a compartment 50 of the cap 3 for closing the receptacle 2 containing the first composition $C_1$. The cap 51 serves as a handle for the magnet 12, and also serves to close the compartment 50.

It is not beyond the ambit of the present invention for the magnetic field to be generated by an electromagnet instead of by a permanent magnet.

FIG. 14 shows a kit 1 comprising a receptacle 2 constituted by a pot containing the first composition $C_1$, and a magnetic device 10 comprising an electromagnet 40 at one end of a casing 44 housing the power supply.

A switch 45 enables the electromagnet 40 to be switched on selectively by the user.

Various devices other than those described above for packaging and/or dispensing or applying the composition $C_1$ and $C_2$, if any, can be used.

By way of example, at least one of the composition(s) $C_1$ and $C_2$, if any, can be deposited on the surface S without using an applicator, but in the form of a spray, e.g. by using a pump 60 as shown in FIG. 15. The spray can also be generated by means of an airbrush or by a pressurized receptacle, for example.

The devices for packaging and/or dispensing or applying the first and second compositions can differ from each other.

A perforated mask 70, as shown in FIG. 16 in which its perforation pattern 71 is in the shape of a star, can be interposed between the spray and the surface to be made up.

An optionally-perforated sheet 75 that is permeable to the magnetic field can be interposed between the magnet 12 or the electromagnet 40 and the surface S, so as to change the shape of the field lines and create novel effects.

The kit 1 shown in FIG. 18 comprises a receptacle 2 containing a fluid composition C for application to the lips, and an applicator 3 comprising an application member 4 mounted at one end of a rod 5 having its other end connected to a grip member 6 that also constitutes a closure for the receptacle 2.

The receptacle 2 is provided with a wiper member 7 for the rod 5 and the application member 4, in conventional manner.

The kit 1 also comprises a magnetic device 10 which is constituted by a permanent magnet, for example, but which in a variation (not shown) may comprise at least one electromagnet, or a magnet that is attached to a mechanical or electromechanical system causing it to move in a predetermined manner to create a pattern with the desired shape on the deposit of the composition to be produced.

Figure 19:
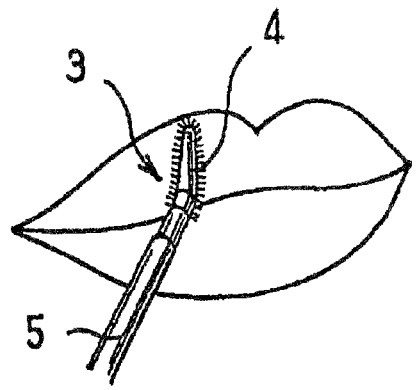
FIG. 19 shows the first composition being applied to the lips.
Figure 20:
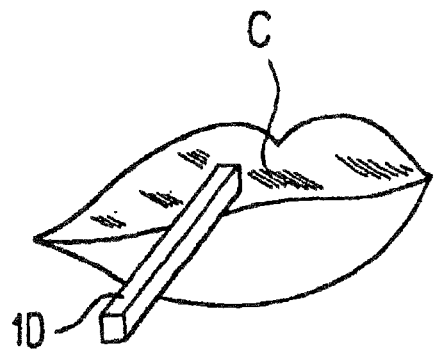
FIG. 20 shows exposure of the first composition to a magnetic field.

The kit 1 is used by firstly applying the composition C using the applicator 3, as shown in FIG. 19, for example in the form of one or more thin layers then, as shown in FIG. 20, by exposing the composition that has been deposited to a magnetic field before it dries, to enable the desired pattern to be formed.

By way of example, for a lip-gloss, said lip-gloss can have the following formulation.

The proportions indicated are given by weight unless otherwise specified.

Example H Lip-Gloss

| | |
|---|---|
| Film-forming polymer** | 65.24 |
| Sucrose acetate isobutyrate | 9.52 |
| Octyldodecanol | 6 |
| Isododecane | 14.1 |
| Magnetic pigment* | 4.76 |
| Fragrance | 0.38 |

*STAPA ® VM VP 041040 soft iron based pigment from ECKART.
**poly(isobornyl acrylate/isobornyl methacrylate/isobutyl acrylate) block polymer, obtained as follows: 100 g of isododecane were introduced into a 1 litre reactor then the temperature was increased to heat it from ambient temperature (25° C.) to 90° C. in 1 hour.

Next, at 90° C. over one hour, 105 g of isobornyl acrylate, 105 g of isobornyl methacrylate, 110 g of isododecane and 1.8 g of 2,5-bis(2-ethylhexanoylperoxy)-2,5-dimethylhexane (Trigonox® 141 d'Akzo Nobel) were added.

The mixture was kept at 1 h 30 at 90° C.

Next, 90 g of isobutyl acrylate, 90 g of isododecane and 1.2 g of 2,5-bis(2-ethylhexanoylperoxy)-2,5-dimethylhexane were introduced into the previous mixture, still at 90° C. and over 30 minutes.

The mixture was kept at 90° C. for 3 hours then cooled.

A solution was obtained with 50% of the active polymer substance in isododecane.

A polymer was obtained comprising a first sequence or poly(isobornyl acrylate/isobornyl methacrylate) block with a Tg of 110° C., a second isobutyl polyacrylate sequence with a Tg of −20° C. and an intermediate sequence which was a random isobornyl acrylate/isobornyl methacrylate/isobutyl acrylate polymer.

Said polymer had a mass average molecular mass of 100300 g/mol and a number average molecular mass of 22800 g/mol, i.e. a polydispersity index I of 4.40. The lip-gloss composition was prepared by heating the non volatile oils to 60° C., with magnetic stirring. The sequenced polymer was introduced into a beaker along with the isododecane, and the whole was stirred with a Rayneri stirrer. When a transparent liquid was observed, the magnetic pigment was introduced and stirring was continued for 20 minutes with Rayneri stirring.

Said composition could be applied using an applicator as shown in FIG. 19.

Drying of the composition was sufficiently slow to allow the formation of a pattern by exposure to the magnetic field such as shown in FIG. 20, which modified the orientation of the magnetic pigment particles. However, the composition set quickly enough for the pattern not to have time to be destroyed after the field was removed.

Naturally, the invention is not limited to the examples given above.

For example, the kit may include a plurality of magnets having various shapes, so as to create various patterns.

Throughout the description, including in the claims and unless specified to the contrary, the expression "comprising a" should be understood as being synonymous with "comprising at least one", and the expression "in the range" should be understood as including the limits of the range.

What is claimed is:

1. A method of applying makeup to a surface selected from the group consisting of the skin, the nails, hair, or the lips, said method comprising:
   manually depositing, using a non-magnetic cosmetic applicator, at least a first cosmetic composition in the fluid state on the surface, said first composition containing magnetic particles that are movable under the effect of a magnetic field; and
   manually exposing at least part of the first composition to a magnetic device producing a magnetic field, the magnetic device located above the first composition so as to orientate and/or displace at least a fraction of the magnetic particles so as to form at least one pattern according to magnetic field lines of the magnetic field without making contact with the first composition, wherein the magnetic particles within the pattern are oriented and/or displaced differently than the magnetic particles outside the pattern.

2. A method according to claim 1, wherein said method comprises:
   depositing at least said first and a second cosmetic composition in the fluid state on the surface, the first composition covering or being covered at least in part by the second.

3. A method according to claim 2, wherein the second composition is applied to the first.

4. A method according to claim 2, wherein the first composition is applied to the second.

5. A method according to claim 2, wherein the second composition is colorless or colored.

6. A method according to claim 2, wherein the second composition is transparent.

7. A method according to claim 1, wherein the first composition comprises at least one volatile solvent.

8. A method according to claim 7, in which the composition comprises at least one film-forming polymer.

9. A method according to claim 7, in which the magnetic particles comprise metallic iron.

10. A method according to claim 1, wherein the first composition comprises at least one coloring agent having optical properties that are sensitive to an external stimulus.

11. A method according to claim 10, in which the coloring agent having optical properties that are sensitive to an external stimulus comprises at least one agent selected from the group comprising thermochromic agent, photochromic agent, tribochromic or piezochromic agent, and solvatochromic agent.

12. A method according to claim 1, wherein the first composition comprises at least one diffractive pigment.

13. A method according to claim 1, wherein the first composition comprises at least one absorbent coloring agent producing a color by absorbing at least a fraction of the visible spectrum.

14. A method according to claim 1, wherein the first composition is a nail varnish.

15. A method according to claim 1, wherein the magnetic field is exerted by a permanent magnet or by an electromagnet.

16. A method according to claim 1, wherein the magnetic field is exerted successively on different regions of the surface that are coated with the first composition.

17. A method according to claim 1, wherein at least one region of the surface that is coated with the first composition is not exposed to the magnetic field.

18. A method according to claim 1, wherein the first composition is applied by means of a cosmetics applicator comprising a brush, a flocked endpiece, or a foam.

19. A method according to claim 1, wherein the magnetic particles comprise a pigment, fibers or chains of particles.

20. A method according to claim 1, wherein the first composition contains magnetic particles and non-magnetic particles.

21. A method according to claim 1, wherein, after a given drying time, the first composition takes on a state that prevents the magnetic particles from changing their orientation under the effect of a magnetic field.

22. A method according to claim 1, in which the deposited first composition is allowed to dry after application of the magnetic field.

23. A method according to claim 1, in which the first composition is deposited on the lips or on the nails.

24. A method according to claim 9, in which the magnetic particles comprise soft iron.

* * * * *